(12) United States Patent
Yokota et al.

(10) Patent No.: US 11,674,141 B2
(45) Date of Patent: *Jun. 13, 2023

(54) ISCHEMIC-LESION-SITE-SPECIFIC GENE THERAPY

(71) Applicant: NATIONAL UNIVERSITY CORPORATION TOKYO MEDICAL AND DENTAL UNIVERSITY, Tokyo (JP)

(72) Inventors: Takanori Yokota, Tokyo (JP); Satoru Ishibashi, Tokyo (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/975,441

(22) PCT Filed: Feb. 27, 2019

(86) PCT No.: PCT/JP2019/007458
§ 371 (c)(1),
(2) Date: Oct. 9, 2020

(87) PCT Pub. No.: WO2019/167995
PCT Pub. Date: Sep. 6, 2019

(65) Prior Publication Data
US 2021/0130825 A1    May 6, 2021

(30) Foreign Application Priority Data

Feb. 28, 2018 (JP) .............................. JP2018-035538
Jul. 20, 2018 (JP) .............................. JP2018-136625

(51) Int. Cl.
*A61K 48/00* (2006.01)
*C12N 15/113* (2010.01)
(Continued)

(52) U.S. Cl.
CPC .......... *C12N 15/113* (2013.01); *A61K 9/0019* (2013.01); *A61K 47/543* (2017.08);
(Continued)

(58) Field of Classification Search
CPC .............. C12N 15/111; C12N 2310/11; C12N 2310/315; C12N 2310/3231; C12N 2310/341; A61K 31/7088; A61K 47/551
See application file for complete search history.

(56) References Cited

U.S. PATENT DOCUMENTS 8,906,875 B2    12/2014  Feinberg
11,433,089 B2 *  9/2022  Yokota ................... C12N 15/111
(Continued)

FOREIGN PATENT DOCUMENTS

WO    WO-2011113015 A2 *  9/2011  .......... C12N 15/1138
WO    2013089283 A1       6/2013
(Continued)

OTHER PUBLICATIONS

Kuehbacher et al. (Circulation, Oct. 28, 2008, 118: S_550, Abstract 5443).*
(Continued)

*Primary Examiner* — Terra C Gibbs
(74) *Attorney, Agent, or Firm* — Lucas & Mercanti, LLP

(57) ABSTRACT

The present invention provides an antisense nucleic acid medicine that can modulate expression of a target transcriptional product in an ischemic site of a subject. The present invention also provides a composition for modulating expression of a target transcriptional product in an ischemic site of a subject, having a nucleic acid complex formed by
(Continued)

annealing together a first nucleic acid strand having an antisense oligonucleotide region with respect to the target transcriptional product, and a lipid-conjugated second nucleic acid strand having a complementary region that is complementary to at least part of the first nucleic acid strand.

17 Claims, 35 Drawing Sheets

Specification includes a Sequence Listing.

(51) Int. Cl.
    *A61K 47/54*     (2017.01)
    *A61P 9/10*     (2006.01)
    *A61K 9/00*     (2006.01)

(52) U.S. Cl.
    CPC .............. *A61K 47/549* (2017.08); *A61P 9/10* (2018.01); *C12N 2310/11* (2013.01); *C12N 2310/3231* (2013.01); *C12N 2310/341* (2013.01); *C12N 2310/3515* (2013.01); *C12N 2310/3519* (2013.01); *C12N 2320/32* (2013.01)

(56) References Cited

U.S. PATENT DOCUMENTS

| | | | |
|---|---|---|---|
| 2005/0107325 | A1 | 5/2005 | Manoharan et al. |
| 2011/0189300 | A1 | 8/2011 | Maclachlan et al. |
| 2012/0184595 | A1 | 7/2012 | Macdonald |
| 2019/0240352 | A1 | 8/2019 | Yokota et al. |
| 2019/0247414 | A1 | 8/2019 | Yokota et al. |

FOREIGN PATENT DOCUMENTS

| | | |
|---|---|---|
| WO | 2014132671 A1 | 9/2014 |
| WO | 2014192310 A1 | 12/2014 |
| WO | 2014203518 A1 | 12/2014 |
| WO | 2018056442 A1 | 3/2018 |
| WO | 2018062510 A1 | 4/2018 |

OTHER PUBLICATIONS

Cleveland Clinic. Heart Attack (Myocardial Infarction). Downloaded on May 24, 2022 from https://my.clevelandclinic.org/health/diseases/16818-heart-attack-myocardial-infarction#:~:text=A%20myocardial%20infarction%20(commonly%20called,more%20of%20your%20heart%27s%20arteries.*

Jürgen Soutschek et al. (Nature, 2004 vol. 432: 173-178).*
Silent Ischemia and Ischemic Heart Disease, https://www.heart.org/en/health-topics/heart-attack/about-heart-attacks/silent-ischemia-and-ischemic-heart-disease downloaded on Sep. 25, 2022.*
Ischemia, https://en.wikipedia.org/wiki/Ischemia downloaded on Sep. 25, 2022.*
How Ischemia Affects Different Parts of the Body, https://www.verywellhealth.com/what-is-ischemia-p2-1745825 downloaded on Sep. 25, 2022.*
Arteriosclerosis / atherosclerosis, https://www.mayoclinic.org/diseases-conditions/arteriosclerosis-atherosclerosis/symptoms-causes/syc-20350569#:~:text=Atherosclerosis%20is%20the%20buildup%20of,leading%20to%20a%20blood%20clot, downloaded on Sep. 25, 2022.*
What Is Ischemia? https://www.webmd.com/heart-disease/what-is-ischemia downloaded on Sep. 26, 2022.*
Scanlon KJ (Current Pharmaceutical Biotechnology, 2004 vol. 5:415-420) (hereinafter, "Scanlon").*
Suzuki et al. (Scientific Reports, 2021 vol. 11: 14237, pp. 1-13, plus Supplementary Information).*
Li et al. (Molecular Therapy, Jun. 2023, vol. 31:1-17).*
Nishina et al., "DNA/RNA heteroduplex oligonucleotide for highly efficient gene silencing", Nature Communications, 2015, vol. 6, No. 7969, pp. 1-13.
Asami et al.,"Drug delivery system of therapeutic oligonucleotides", Drug Discoveries & Therapeutics, 2016, vol. 10, No. 5, pp. 256-262.
Krutzfeldt et al., "Silencing of microRNAs in vivo with 'antagomirs'", Nature, 2005, vol. 438, pp. 685-689.
Kuehbacher et al., "MicroRNA 92a Controls Vessel Growth And Functional Recovery After Ischemia", Biosis, 2008, pp. 1-2.
Thum et al., "MicroRNA therapeutics in cardiovascular medicine", EMBO Mal Med, 2012, vol. 4, No. 1, pp. 3-14.
Caroli et al., "Potential therapeutic role of microRNAs in ischemic heart disease", Journal of Cardiology, 2013, vol. 61, No. 5, pp. 315-320.
Kuwahara et al., "Heteroduplex oligonucleotide as a platform technology to modulate blood-brain barrier function in vivo", Journal of Neurological Sciences, 2017, vol. 381, p. 141.
Soutschek et al., "Therapeutic silencing of an endogenous gene by systemic administration of modified siRNAs", Nature, 2004, vol. 432, No. 7014, pp. 173-178.
Nishina et al., "Chimeric Antisense Oligonucleotide Conjugated to [alpha]-Tocophero!", Molecular Therapy—Nucleic Acids, 2015, vol. 4, No. 1, 2015, pp. 1-10.
Supplementary European Search Report for Corresponding EP Application No. 19760346.7, 19 pages, Oct. 11, 2021.

* cited by examiner

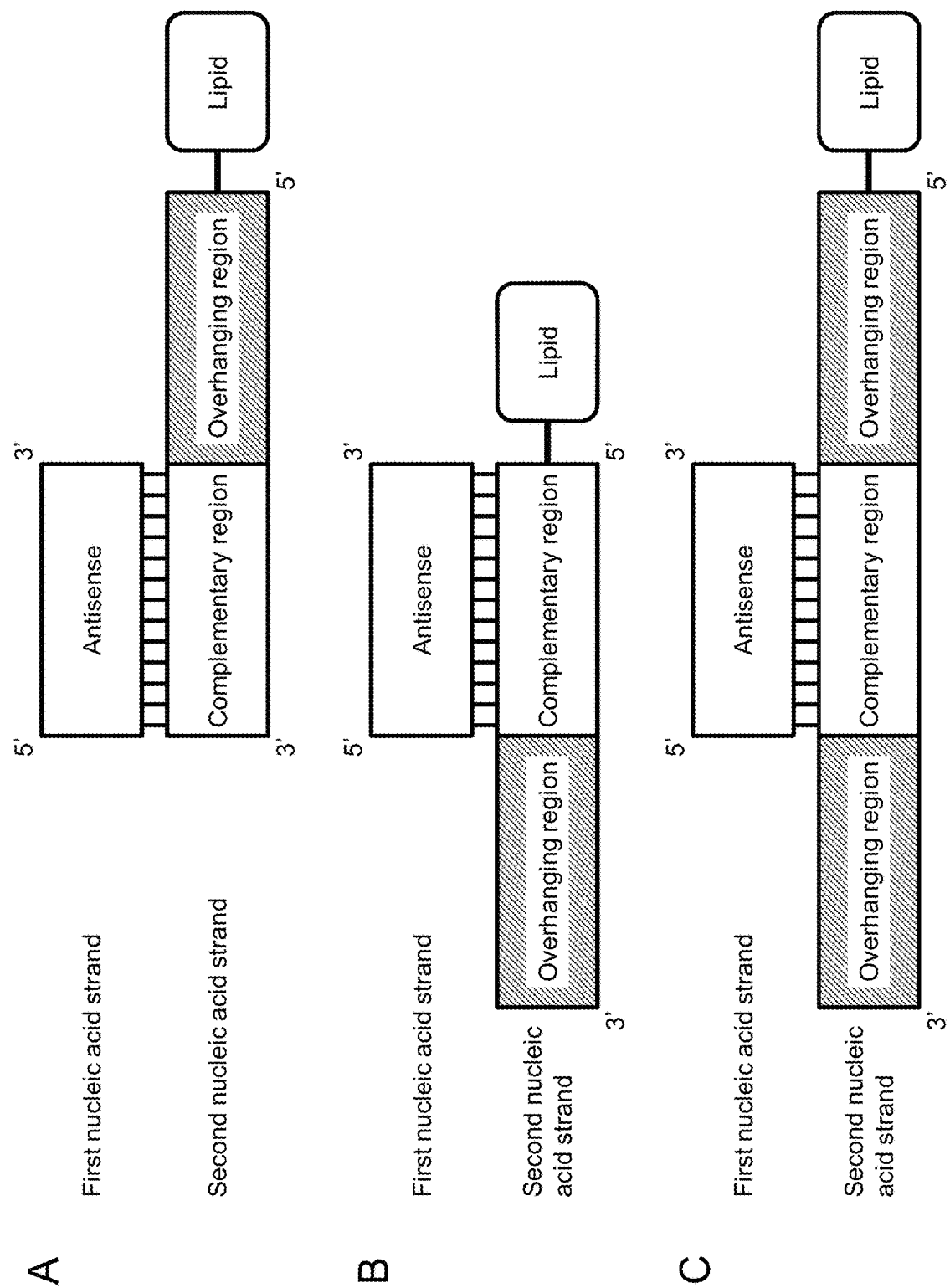

Fig. 21
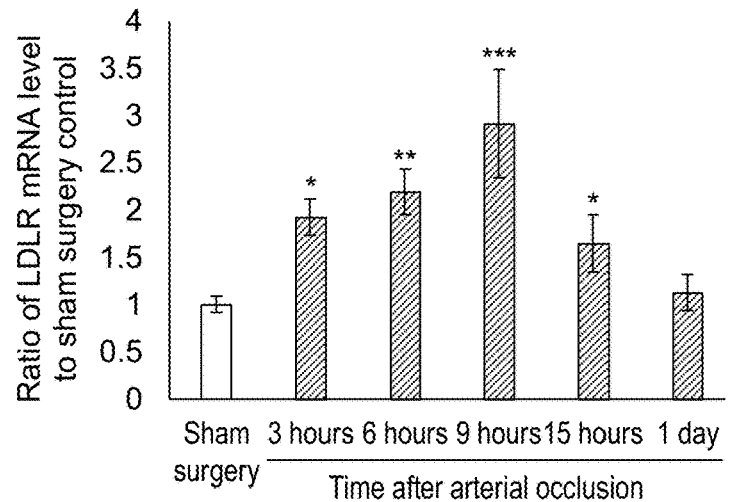
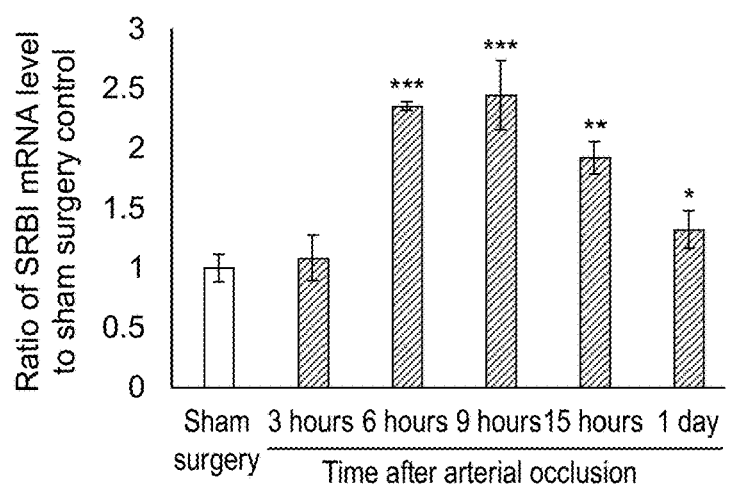
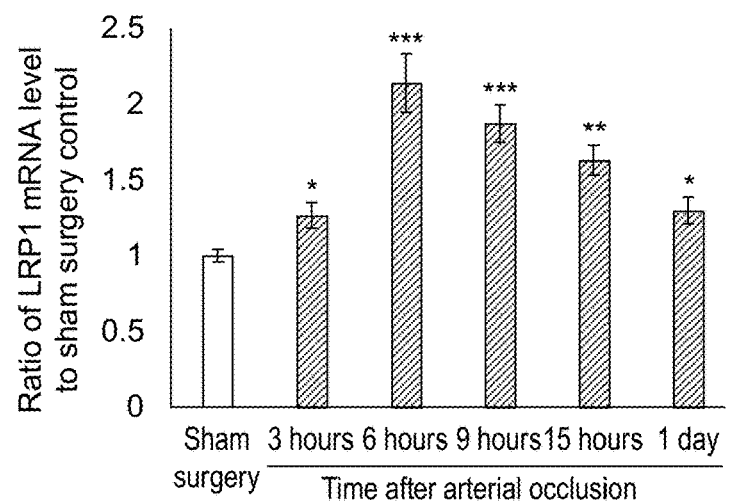

SEQUENCE LISTING

<160> NUMBER OF SEQ ID NOS: 6

<210> SEQ ID NO 1
<211> LENGTH: 6983
<212> TYPE: DNA
<213> ORGANISM: Mus musculus

<400> SEQUENCE: 1

| | | | | | |
|---|---|---|---|---|---|
| caggcattca | ggcagcgaga | gcagagcagc | gtagagcagc | acagctgagc | tcgtgaggca | 60 |
| ggagactcag | cccgaggaaa | tcgcagataa | gtttttaatt | aaaaagattg | agcagtaaaa | 120 |
| agaattagaa | ctctaaactt | aagctaatag | agtagcttat | cgaaatatta | cttagtctta | 180 |
| ataatctaag | aagatcttaa | gagataacat | gaaggcttat | ttaaacagtt | tgaaaaagga | 240 |
| aatgaggaga | aaagtatttg | tactgtataa | tggaggctga | ccagagcagt | ttaggagatt | 300 |
| gtaaagggag | gttttgtgaa | gttctaaaag | gttctagttt | gaaggtcggc | cttgtagatt | 360 |
| aaaacgaagg | ttacctaaat | agaatctaag | tggcatttaa | aacagtaaag | ttgtagagaa | 420 |
| tagtttgaaa | atgaggtgta | gttttaaaag | attgagaaaa | gtaggttaag | ttgacggccg | 480 |
| ttataaaaat | ccttcgactg | gcgcatgtac | gtttgaaggc | atgagttgga | aacagggaag | 540 |
| atggaagtgt | taggctagcc | gggcgatggt | ggcgcacgcc | tttaatccta | gcacttggga | 600 |
| ggcagaggca | ggcggatttc | tgagttcgag | gccagcctgg | tctacagagt | gagttccagg | 660 |
| acagccaggg | ctacacagag | aaaccctgtc | ttgaaaaaac | aaaaaggtta | ggctagtatt | 720 |
| tggagaaaga | agattagaaa | atggaagtga | aagacgaaga | agacatacag | gaaggtgaag | 780 |
| aaaaagctgt | tagagaagat | aggaaaatag | aagacaaagc | atctttagaa | gacagaaaag | 840 |
| gtacttaaag | gcacaggtag | taggaagccg | aagaatagaa | gatagaaaga | agcaagatag | 900 |
| aaaaacaaaa | tggaagttaa | gacaactttg | gatgccagca | ttcaagatag | gcaaagaaga | 960 |
| taagattgag | gccaaaaggt | tggataagat | ataaagtcag | aaggaaatta | tctttaaagc | 1020 |
| cataagttca | aatttctgat | ggagcgagca | gtttagaaga | gtctttagac | agccacatac | 1080 |
| aagattgaag | ctagcaatca | aagctactag | gactgaagta | aaaagttaag | gcagaatgcc | 1140 |
| tttgaagagt | tagaagaata | ttaaaagcct | taacttgtag | cttaattttg | cttgatgaca | 1200 |
| aaaggacttt | tgataacagt | ttcaagattg | tcagcatttt | gcattggact | tgagctgagg | 1260 |
| tgcttttaaa | atcctaacga | ctagcattgg | cagctgaccc | aggtctacac | agaagtgcat | 1320 |
| tcagtgaact | aggaagacag | gagcggcaga | caggagtccc | gaagccagtt | tggtgaagct | 1380 |
| aggaaggact | gaggagccag | cagcagcagt | gcatggtgaa | gatagcccag | gaaagagtgc | 1440 |
| ggttcggtgg | aggaagctag | gaagaaggag | ccatacggat | gtggtggtga | agctgggaaa | 1500 |
| gggttccagg | atggtggagc | gagagcgagt | tggtgatgaa | gctagctggc | ggcttggctt | 1560 |
| gtcaactgcg | cggaggaggc | gagcaggcat | tgtggagagg | atagatagcg | gctcctagac | 1620 |
| cagcatgcca | gtgtgcaaga | aaggctgcag | ggagagcatg | cggtgcggta | acattccttg | 1680 |
| aggtcggcaa | catggtggtg | gttttctgta | acttggatgg | taacttgttt | actttgtctt | 1740 |
| aatagttatg | ggggagttgt | aggcttctgt | gtaaagagat | atatctgggg | ctgtatgtag | 1800 |
| gcctttgcgg | gtgttgtagg | ttttttcttt | tcagggttat | gtcctcttgc | atcttgtcag | 1860 |
| aagcttttga | gggctgactg | ccaaggccca | gaaagaagaa | tggtagatgg | caagttgtct | 1920 |
| ttaaccgctc | agaggggaat | gaatggtaga | gccagcacaa | cctcccagtt | ttgtaagacg | 1980 |
| ttgtagtttg | aacagatgac | ctaccacaag | cctcactcct | gtgtagggga | ggtaattggg | 2040 |
| caaagtgctt | ttgggggaat | ggggggcaaaa | tatattttga | gttcttttcc | ccttaggtct | 2100 |

```
gtctagaatc ctaaaggcag atgactcaag ggaaccagaa aaaggaaat ccactctcag    2160 gataagcaga gctcgccagg tttacagttt gtaggaagta gaggatggat gctagctttc    2220
acactgagtg tggaggagct ggccatggcg gaattgctgg tagtttactc tttccccctc    2280
ccttaatgag atttgtaaaa tcctaaacac ttttacttga aatatttggg agtggtctta    2340
acagggagga gtgggtgggg gaaacgtttt ttttctaaga ttttccacag atgctatagt    2400
tgtgttgaca cactgggtta gagaaggcgt gtactgctat gctgttggca cgacaccttc    2460
agggactgga gctgcctttt gtccttggaa gagttttccc agttgccgct gaagtcagca    2520
cagtgcggct ttggttcaca gtcacctcag gagaacctca ggagcttggc taggccagag    2580
gttgaagtta agttttacag caccgtgatt taaaatattt cattaaaggg gaggggtaaa    2640
acttagttgg ctgtggcctt gtgtttgggt gggtgggggt gttaggtaat tgtttagttt    2700
atgatttcag ataatcatac cagagaactt aaatatttgg aaaaacagga aatctcagct    2760
ttcaagttgg caagtaactc ccaatccagt ttttgcttct ttttcctttt tctttttttt    2820
gaggcgggca gctaaggaag gttggttcct ctgccggtcc ctcgaaagcg tagggcttgg    2880
gggttggtct ggtccactgg gatgatgtga tgctacagtg gggactcttc tgaagctgtt    2940
ggatgaatat agattgtagt gtgtggttct cttttgaaat ttttttcagg tgacttaatg    3000
tatcttaata actactatag gaacaaagga agtggcttta atgaccctga aggaatttct    3060
tctggtgata gcttttatat tatcaagtaa gagatactat ctcagttttg tataagcaag    3120
tctttttcct agtgtaggag aaatgatttt ccttgtgact aaacaagatg taaaggtatg    3180
ctttttttct tcttgtgcat tgtatacttg tgtttatttg taacttataa tttaagaatt    3240
atgataattc agcctgaatg tcttttagag ggtgggcttt tgttgatgag ggaggggaaa    3300
cctttttttt tctgtagacc tttttcagat aacaccatct gagtcataac cagcctggca    3360
gtgtgatgac gtagatgcag agggagcagc tccttggtga atgagtgata agtaaaggca    3420 gaaaaataa tgtcatgtct ccatggggaa tgagcatgag ccagagattg ttcctactga    3480
tgaaaagctg catatgcaaa aatttaagca aatgaaagca accagtataa agttatggca    3540 ataccttta aagttatggc ttatctacca agctttatcc acaaaagtaa agaattgatg    3600
aaaaacagtg aagatcaaat gttcatctca aaactgcttt tacaaaagca gaatagaaat    3660
gaagtgaaaa tgctgcatta agcctggagt aaaaagaagc tgagcttgtt gagatgagtg    3720
ggatcgagcg gctgcgaggc ggtgcagtgt gccaatgttt cgtttgcctc agacaggttt    3780
ctcttcataa gcagaagagt tgcttcattc catctcggag caggaaacag cagactgctg    3840
ttgacagata agtgtaactt ggatctgcag tattgcatgt tagggataga taagtgcctt    3900
ttttctcttt ttccaaaaag acctgtagag ctgttgaatg tttgcagctg gcccctctta    3960
ggcagttcag aattttgagt agttttccca tccagcctct taaaaattcc taagccttgc    4020
accgatgggc tttcatgatg ggatagctaa taggcttttg catcgtaaac ttcaacacaa    4080
aagcctacat gattaatgcc tactttaatt acattgctta caagattaag gaatctttat    4140
cttgaagacc ccatgaaagg gatcattatg tgctgaaaat tagatgttca tattgctaaa    4200
atttaaatgt gctccaatgt acttgtgctt aaaatcatta aattatacaa attaataaaa    4260
tacttcacta gagaatgtat gtatttagaa ggctgtctcc ttatttaaat aaagtcttgt    4320
ttgttgtctg tagttagtgt gggcaatttt gggggatgt tcttctctaa tcttttcaga    4380
aacttgactt cgaacactta agtggaccag atcaggattt gagccagaag accgaaatta    4440
```

```
actttaaggc aggaaagaca aatttttattc tccatgcagt gatgagcatt taataattgc    4500
aggcctggca tagaggccgt ctaactaagg actaagtacc ttaggcaggt gggagatgat    4560
ggtcagagta aaaggtaact acatattttg tttccagaaa gtcagggggtc taatttgacc   4620 atggctaaac atctagggta agacactttt cccccacatt tccaaatatg catgttgagt    4680
ttaaatgctt acgatcatct catccacttt agccttttgt cacctcactt gagccacgag    4740
tggggtcagg catgtgggtt taaagagttt cctttgcag agcctcattt catccttcat     4800
ggagctgctc aggactttgc atataagcgc ttgcctctgt cttctgttct gctagtgagt    4860
gtgtgatgtg agaccttgca gtgagtttgt ttttcctgga atgtggaggg agggggggat    4920
ggggcttact tgttctagct ttttttttac agaccacaca gaatgcaggt gtcttgactt    4980
caggtcatgt ctgttctttg gcaagtaata tgtgcagtac tgttccaatc tgctgctatt    5040
agaatgcatt gtgacgcgac tggagtatga ttaaagaaag ttgtgttttcc ccaagtgttt   5100 ggagtagtgg ttgttggagg aaaagccatg agtaacaggc tgagtgttga ggaaatggct    5160
ctctgcagct ttaagtaacc cgtgtttgtg attggagccg agtcccttttg ctgtgctgcc   5220 ttaggtaaat gttttttgttc atttctggtg aggggggttg ggagcactga agcctttagt   5280
ctcttccaga ttcaacttaa aatctgacaa gaaataaatc agacaagcaa cattcttgaa    5340
gaaattttaa ctggcaagtg gaaatgtttt gaacagttcc gtggtcttta gtgcattatc    5400
tttgtgtagg tgttctctct cccctccctt ggtcttaatt cttacatgca ggaacattga    5460
caacagcaga catctatcta ttcaaggggc cagagaatcc agacccagta aggaaaaata    5520
gcccatttac tttaaatcga taagtgaagc agacatgcca ttttcagtgt ggggattggg    5580
aagccctagt tctttcagat gtacttcaga ctgtagaagg agcttccagt tgaattgaaa    5640
ttcaccagtg gacaaaatga ggacaacagg tgaacgagcc ttttcttgtt taagattagc    5700
tactggtaat ctagtgttga atcctctcca gcttcatgct ggagcagcta gcatgtgatg    5760
taatgttggc cttggggtgg aggggtgagg tgggcgctaa gccttttttt aagatttttc    5820
aggtacccct cactaaaggc actgaaggct taatgtagga cagcggagcc ttcctgtgtg    5880
gcaagaatca agcaagcagt attgtatcga gaccaaagtg gtatcatggt cggttttgat    5940
tagcagtggg gactacccta ccgtaacacc ttgttggaat tgaagcatcc aaagaaaata    6000
cttgagaggc cctgggcttg ttttaacatc tggaaaaaag gctgttttta tagcagcggt    6060
taccagccca aacctcaagt tgtgcttgca ggggagggaa aaggggggaaa gcgggcaacc   6120 agtttcccca gcttttccag aatcctgtta caaggtctcc ccacaagtga tttctctgcc    6180
acatcgccac catgggcctt tggcctaatc acagacccctt cacccctcac cttgatgcag   6240
ccagtagctg gatccttgag gtcacgttgc atatcggttt caaggtaacc atggtgccaa    6300
ggtcctgtgg gttgcaccag aaaaggccat caatttttccc cttgcctgta atttaacatt   6360
aaaaccatag ctaagatgtt ttatacatag cacctatgca gagtaaacaa accagtatgg    6420
gtatagtatg tttgataccca gtgctgggtg ggaatgtagg aagtcggatg aaaagcaagc   6480
ctttgtagga agttgttggg gtgggattgc aaaaattctc tgctaagact ttttcaggtg    6540
gacataacag acttggccaa gctagcatct tagtggaagc agattcgtca gtagggttgt    6600
aaaggttttt cttttcctga gaaaacaacc ttttgttttc tcaggtttttg cttttggcc    6660 tttccctagc tttaaaaaaa aaaagcaaa agacgctggt ggctggcact cctggtttcc    6720
aggacggggt tcaagtccct gcggtgtctt tgcttgactc ttatatcatg aggccattac    6780 attttttcttg gagggttcta aaggctctgg gtatggtagc tgatatcact ggaacactcc    6840
```

-continued

| | |
|---|---|
| ccagcctcag tgttgaactc ttgataatta actgcattgt ctttcaggtt atgcccaatt | 6900 |
| cgtcttatta cctctgagtc gacacacctc ctactattta ttgaatactt tgattttatg | 6960 |
| aaataaaaac taaatatctc tca | 6983 |

<210> SEQ ID NO 2
<211> LENGTH: 8779
<212> TYPE: DNA
<213> ORGANISM: Homo sapiens

<400> SEQUENCE: 2

| | |
|---|---|
| cgcagcctgc agcccgagac ttctgtaaag gactggggcc ccgcaactgg cctctcctgc | 60 |
| cctcttaagc gcagcgccat tttagcaacg cagaagcccg gcgccgggaa gcctcagctc | 120 |
| gcctgaaggc aggtcccctc tgacgcctcc gggagcccag gtttcccaga gtccttggga | 180 |
| cgcagcgacg agttgtgctg ctatcttagc tgtccttata ggctggccat tccaggtggt | 240 |
| ggtatttaga taaaaccact caaactctgc agtttggtct tggggtttgg aggaaagctt | 300 |
| ttatttttct tcctgctccg gttcagaagg tctgaagctc atacctaacc aggcataaca | 360 |
| cagaatctgc aaaacaaaaa cccctaaaaa agcagaccca gagcagtgta aacacttctg | 420 |
| ggtgtgtccc tgactggctg cccaaggtct ctgtgtcttc ggagacaaag ccattcgctt | 480 |
| agttggtcta ctttaaaagg ccacttgaac tcgcttttcca tggcgatttg ccttgtgagc | 540 |
| actttcagga gagcctggaa gctgaaaaac ggtagaaaaa tttccgtgcg ggccgtgggg | 600 |
| ggctggcggc aactgggggg ccgcagatca gagtgggcca ctggcagcca acggcccccg | 660 |
| gggctcaggc ggggagcagc tctgtggtgt gggattgagg cgttttccaa gagtgggttt | 720 |
| tcacgtttct aagatttccc aagcagacag cccgtgctgc tccgatttct cgaacaaaaa | 780 |
| agcaaaacgt gtggctgtct tgggagcaag tcgcaggact gcaagcagtt gggggagaaa | 840 |
| gtccgccatt ttgccacttc tcaaccgtcc ctgcaaggct ggggctcagt tgcgtaatgg | 900 |
| aaagtaaagc cctgaactat cacactttaa tcttccttca aaggtggta aactatacct | 960 |
| actgtccctc aagagaacac aagaagtgct ttaagaggta ttttaaaagt tccgggggtt | 1020 |
| ttgtgaggtg tttgatgacc cgtttaaaat atgatttcca tgtttctttt gtctaaagtt | 1080 |
| tgcagctcaa atctttccac acgctagtaa tttaagtatt tctgcatgtg tagtttgcat | 1140 |
| tcaagttcca taagctgtta agaaaatct agaaaagtaa aactagaacc tatttttaac | 1200 |
| cgaagaacta cttttttgcct ccctcacaaa ggcggcggaa ggtgatcgaa ttccggtgat | 1260 |
| gcgagttgtt ctccgtctat aaatacgcct cgcccgagct gtgcggtagg cattgaggca | 1320 |
| gccagcgcag gggcttctgc tgaggggcca ggcggagctt gaggaaaccg cagataagtt | 1380 |
| ttttttctctt tgaaagatag agattaatac aactacttaa aaaatatagt caataggtta | 1440 |
| ctaagatatt gcttagcgtt aagtttttaa cgtaatttta atagcttaag attttaagag | 1500 |
| aaaatatgaa gacttagaag agtagcatga ggaaggaaaa gataaaaggt ttctaaaaca | 1560 |
| tgacggaggt tgagatgaag cttcttcatg gagtaaaaaa tgtatttaaa agaaaattga | 1620 |
| gagaaaggac tacagagccc cgaattaata ccaatagaag ggcaatgctt ttagattaaa | 1680 |
| atgaaggtga cttaaacagc ttaaagttta gtttaaaagt tgtaggtgat taaaataatt | 1740 |
| tgaaggcgat cttttaaaaa gagattaaac cgaaggtgat taaagacct tgaaatccat | 1800 |
| gacgcaggga gaattgcgtc atttaaagcc tagttaacgc atttactaaa cgcagacgaa | 1860 |
| aatggaaaga ttaattggga gtggtaggat gaaacaattt ggagaagata gaagtttgaa | 1920 |

```
gtggaaaact ggaagacaga agtacgggaa ggcgaagaaa agaatagaga agatagggaa      1980
attagaagat aaaaacatac ttttagaaga aaaaagataa atttaaacct gaaaagtagg      2040
aagcagaaga aaaaagacaa gctaggaaac aaaaagctaa gggcaaaatg tacaaactta      2100
gaagaaaatt ggaagataga aacaagatag aaaatgaaaa tattgtcaag agtttcagat      2160
agaaaatgaa aaacaagcta agacaagtat tggagaagta tagaagatag aaaaatataa      2220
agccaaaaat tggataaaat agcactgaaa aaatgaggaa attattggta accaatttat      2280
tttaaaagcc catcaattta atttctggtg gtgcagaagt tagaaggtaa agcttgagaa      2340
gatgagggtg tttacgtaga ccagaaccaa tttagaagaa tacttgaagc tagaagggga      2400
agttggttaa aaatcacatc aaaaagctac taaaaggact ggtgtaattt aaaaaaaact      2460
aaggcagaag ctttttggaa gagttagaag aatttggaag gccttaaata tagtagctta      2520
gtttgaaaaa tgtgaaggac tttcgtaacg gaagtaattc aagatcaaga gtaattacca      2580
acttaatgtt tttgcattgg actttgagtt aagattattt tttaaatcct gaggactagc      2640
attaattgac agctgaccca ggtgctacac agaagtggat tcagtgaatc taggaagaca      2700
gcagcagaca ggattccagg aaccagtgtt tgatgaagct aggactgagg agcaagcgag      2760
caagcagcag ttcgtggtga agataggaaa agagtccagg agccagtgcg atttggtgaa      2820
ggaagctagg aagaaggaag gagcgctaac gatttggtgg tgaagctagg aaaaaggatt      2880
ccaggaagga gcgagtgcaa tttggtgatg aaggtagcag gcggcttggc ttggcaacca      2940
cacggaggag gcgagcaggc gttgtgcgta gaggatccta gaccagcatg ccagtgtgcc      3000
aaggccacag ggaaagcgag tggttggtaa aaatccgtga ggtcggcaat atgttgtttt      3060
tctggaactt acttatggta acctttttatt tattttctaa tataatgggg gagtttcgta      3120
ctgaggtgta aagggattta atggggacg taggccgatt tccgggtgtt gtaggttct       3180 ctttttcagg cttatactca tgaatcttgt ctgaagcttt tgagggcaga ctgccaagtc      3240
ctggagaaat agtagatggc aagtttgtgg gttttttttt tttacacgaa tttgaggaaa      3300
accaaatgaa tttgatagcc aaattgagac aatttcagca aatctgtaag cagtttgtat      3360
gtttagttgg ggtaatgaag tatttcagtt ttgtgaatag atgacctgtt tttacttcct      3420
caccctgaat tcgttttgta aatgtagagt ttggatgtgt aactgaggcg ggggggagtt      3480
ttcagtattt tttttttgtgg gggtggggc aaaatatgtt ttcagttctt tttccttag      3540 gtctgtctag aatcctaaag gcaaatgact caaggtgtaa cagaaaacaa gaaaatccaa      3600
tatcaggata atcagaccac cacaggttta cagtttatag aaactagagc agttctcacg      3660
ttgaggtctg tggaagagat gtccattgga gaaatggctg gtagttactc ttttttcccc      3720 ccacccccctt aatcagactt taaaagtgct taacccctta aacttgttat tttttacttg      3780
aagcattttg ggatggtctt aacagggaag agagagggtg ggggagaaaa tgttttttttc     3840 taagattttc cacagatgct atagtactat tgacaaactg ggttagagaa ggagtgtacc      3900
gctgtgctgt tggcacgaac accttcaggg actggagctg ctttttatcct tggaagagta     3960 ttcccagttg aagctgaaaa gtacagcaca gtgcagcttt ggttcatatt cagtcatctc      4020
aggagaactt cagaagagct tgagtaggcc aaatgttgaa gttaagtttt ccaataatgt      4080
gacttcttaa aagtttttatt aaaggggagg ggcaaatatt ggcaattagt tggcagtggc     4140
ctgttacggt tgggattggt ggggtgggtt taggtaattg tttagtttat gattgcagat      4200
aaactcatgc cagagaactt aaagtcttag aatggaaaaa gtaaagaaat atcaacttcc      4260
aagttggcaa gtaactccca atgatttagt tttttttcccc ccagtttgaa ttgggaagct      4320
```

```
gggggaagtt aaatatgagc cactgggtgt accagtgcat taatttgggc aaggaaagtg    4380
tcataatttg atactgtatc tgttttcctt caaagtatag agcttttggg gaaggaaagt    4440
attgaactgg gggttggtct ggcctactgg gctgacatta actacaatta tgggaaatgc    4500
aaaagttgtt tggatatggt agtgtgtggt tctcttttgg aatttttttc aggtgattta    4560
ataataattt aaaactacta tagaaactgc agagcaaagg aagtggctta atgatcctga    4620
agggatttct tctgatggta gcttttgtat tatcaagtaa gattctattt tcagttgtgt    4680
gtaagcaagt ttttttttag tgtaggagaa atacttttcc attgtttaac tgcaaaacaa    4740
gatgttaagg tatgcttcaa aaattttgta aattgtttat tttaaactta tctgtttgta    4800
aattgtaact gattaagaat tgtgatagtt cagcttgaat gtctcttaga gggtgggctt    4860
ttgttgatga gggaggggaa acttttttt tttctataga cttttttcag ataacatctt    4920
ctgagtcata accagcctgg cagtatgatg gcctagatgc agagaaaaca gctccttggt    4980
gaattgataa gtaaaggcag aaaagattat atgtcatacc tccattgggg aataagcata    5040
accctgagat tcttactact gatgagaaca ttatctgcat atgccaaaaa attttaagca    5100
aatgaaagct accaatttaa agttacggaa tctaccattt taaagttaat tgcttgtcaa    5160
gctataacca caaaaataat gaattgatga gaaatacaat gaagaggcaa tgtccatctc    5220
aaaatactgc ttttacaaaa gcagaataaa agcgaaaaga aatgaaaatg ttacactaca    5280
ttaatcctgg aataaaagaa gccgaaataa atgagagatg agttgggatc aagtggattg    5340
aggaggctgt gctgtgtgcc aatgtttcgt ttgcctcaga caggtatctc ttcgttatca    5400
gaagagttgc ttcatttcat ctgggagcag aaaacagcag gcagctgtta acagataagt    5460
ttaacttgca tctgcagtat tgcatgttag ggataagtgc ttatttttaa gagctgtgga    5520
gttcttaaat atcaaccatg gcactttctc ctgaccccctt ccctagggga tttcaggatt    5580
gagaaatttt tccatcgagc ctttttaaaa ttgtaggact tgttcctgtg ggcttcagtg    5640
atgggatagt acacttcact cagaggcatt tgcatcttta ataatttct taaaagcctc    5700 taaagtgatc agtgccttga tgccaactaa ggaaatttgt ttagcattga atctctgaag    5760
gctctatgaa aggaatagca tgatgtgctg ttagaatcag atgttactgc taaaatttac    5820
atgttgtgat gtaaattgtg tagaaaacca ttaaatcatt caaaataata aactatttt    5880 attagagaat gtatacttt agaaagctgt ctccttattt aaataaaata gtgtttgtct    5940
gtagttcagt gttggggcaa tcttgggggg gattcttctc taatctttca gaaactttgt    6000
ctgcgaacac tctttaatgg accagatcag gatttgagcg gaagaacgaa tgtaacttta    6060
aggcaggaaa gacaaatttt attcttcata aagtgatgag catataataa ttccaggcac    6120
atggcaatag aggccctcta aataaggaat aaataacctc ttagacaggt gggagattat    6180
gatcagagta aaaggtaatt acacatttta tttccagaaa gtcaggggtc tataaattga    6240
cagtgattag agtaatactt tttcacattt ccaaagtttg catgttaact ttaaatgctt    6300
acaatcttag agtggtaggc aatgttttac actattgacc ttatatatggg aagggagggg    6360 gtgcctgtgg ggttttaaag aattttcctt tgcagaggca tttcatcctt catgaagcca    6420
ttcaggattt tgaattgcat atgagtgctt ggctcttcct tctgttctag tgagtgtatg    6480
agaccttgca gtgagtttat cagcatactc aaaatttttt tcctggaatt tggagggatg    6540
ggaggagggg gtgggggctta cttgttgtag cttttttttt tttacagac ttcacagaga    6600 atgcagttgt cttgacttca ggtctgtctg ttctgttggc aagtaaatgc agtactgttc    6660
```

```
tgatcccgct gctattagaa tgcattgtga aacgactgga gtatgattaa aagttgtgtt    6720
ccccaatgct tggagtagtg attgttgaag gaaaaaatcc agctgagtga taaaggctga    6780
gtgttgagga aatttctgca gttttaagca gtcgtatttg tgattgaagc tgagtacatt    6840
ttgctggtgt atttttaggt aaaatgcttt ttgttcattt ctggtggtgg gaggggactg    6900
aagcctttag tcttttccag atgcaacctt aaaatcagtg acaagaaaca ttccaaacaa    6960
gcaacagtct tcaagaaatt aaactggcaa gtggaaatgt ttaaacagtt cagtgatctt    7020
tagtgcattg tttatgtgtg ggtttctctc tcccctccct tggtcttaat tcttacatgc    7080
aggaacactc agcagacaca cgtatgcgaa gggccagaga agccagaccc agtaagaaaa    7140
aatagcctat ttactttaaa taaaccaaac attccatttt aaatgtgggg attgggaacc    7200
actagttctt tcagatggta ttcttcagac tatagaagga gcttccagtt gaattcacca    7260
gtggacaaaa tgaggaaaac aggtgaacaa gcttttctg tatttacata caaagtcaga    7320
tcagttatgg gacaatagta ttgaatagat ttcagcttta tgctgagta actggcatgt    7380 gagcaaactg tgttggcgtg ggggtggagg ggtgaggtgg gcgctaagcc ttttttaag    7440 attttttcagg taccccctcac taaaggcacc gaaggcttaa agtaggacaa ccatggagcc    7500
ttcctgtggc aggagagaca acaaagcgct attatcctaa ggtcaagaga agtgtcagcc    7560
tcacctgatt tttattagta atgaggactt gcctcaactc cctctttctg gagtgaagca    7620
tccgaaggaa tgcttgaagt accccctgggc ttctcttaac atttaagcaa gctgttttta    7680
tagcagctct taataataaa gcccaaatct caagcggtgc ttgaagggga gggaaggggg    7740
gaaagcgggc aaccactttt ccctagcttt tccagaagcc tgttaaaagc aaggtctccc    7800
cacaagcaac ttctctgcca catcgccacc ccgtgccttt tgatctagca cagaccttc    7860 accctcacc tcgatgcagc cagtagcttg gatccttgtg ggcatgatcc ataatcggtt    7920
tcaaggtaac gatggtgtcg aggtctttgg tgggttgaac tatgttagaa aaggccatta    7980
atttgcctgc aaattgttaa cagaagggta ttaaaaccac agctaagtag ctctattata    8040
atacttatcc agtgactaaa accaacttaa accagtaagt ggagaaataa catgttcaag    8100
aactgtaatg ctgggtggga acatgtaact tgtagactgg agaagatagg catttgagtg    8160
gctgagaggg cttttgggtg ggaatgcaaa aattctctgc taagactttt tcaggtgaac    8220
ataacagact tggccaagct agcatcttag cggaagctga tctccaatgc tcttcagtag    8280
ggtcatgaag gtttttcttt tcctgagaaa acaacacgta ttgttttctc aggttttgct    8340
ttttggcctt tttctagctt aaaaaaaaaa aaagcaaaag atgctggtgg ttggcactcc    8400
tggtttccag gacggggttc aaatccctgc ggcgtctttg ctttgactac taatctgtct    8460
tcaggactct ttctgtattt ctccttttct ctgcaggtgc tagttcttgg agttttgggg    8520
aggtgggagg taacagcaca atatctttga actatataca tccttgatgt ataatttgtc    8580
aggagcttga cttgattgta tattcatatt tacacgagaa cctaatataa ctgccttgtc    8640
tttttcaggt aatagcctgc agctggtgtt ttgagaagcc ctactgctga aaacttaaca    8700
attttgtgta ataaaaatgg agaagctcta aattgttgtg gttcttttgt gaataaaaaa    8760
atcttgattg gggaaaaaa                                                 8779
```

<210> SEQ ID NO 3
<211> LENGTH: 16
<212> TYPE: DNA
<213> ORGANISM: Artificial
<220> FEATURE:
<223> OTHER INFORMATION: Synthetic

```
-continued

<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 3
ctagttcact gaatgc                                                   16

<210> SEQ ID NO 4
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-O-Me RNA
<220> FEATURE:
<221> NAME/KEY: misc_feature
<222> LOCATION: (14)..(16)
<223> OTHER INFORMATION: 2'-O-Me RNA

<400> SEQUENCE: 4
gcauucagug aacuag                                                   16

<210> SEQ ID NO 5
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 5
tacatatgcg ctactg                                                   16

<210> SEQ ID NO 6
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-O-Me RNA
<220> FEATURE:
<221> NAME/KEY: misc_feature
<222> LOCATION: (14)..(16)
<223> OTHER INFORMATION: 2'-O-Me RNA

<400> SEQUENCE: 6
caguagcgca uaugua                                                   16
```

US 11,674,141 B2

ISCHEMIC-LESION-SITE-SPECIFIC GENE THERAPY

CROSS-REFERENCE TO RELATED APPLICATIONS

This application is a 371 of PCT/JP2019/007458, filed Feb. 27, 2019, which claims the benefit of Japanese Patent Application No. 2018-035538, filed Feb. 28, 2018 and Japanese Patent Application No. 2018-136625, filed Jul. 20, 2018

TECHNICAL FIELD

The present invention relates to an antisense nucleic acid medicine that can modulate expression of a target transcriptional product in an ischemic site of a subject.

BACKGROUND ART

One-fourth of death causes of the Japanese is due to vascular disorder, including heart disease and cerebrovascular disorder. Particularly, ischemic stroke is one of the most common causes of death of the Japanese with about 1.5 million patients in Japan, and it is believed that about 500,000 cases of ischemic stroke occur each year. Further, the second most frequent cause of death of the Japanese is heart disease, which mostly is myocardial infarction, or a heart disease resulting from myocardial infarction. There is a need to develop a method to treat these ischemic diseases associated with vascular disorder.

In recent years, an oligonucleotide has been drawing attention in the ongoing development of pharmaceuticals called nucleic acid medicines, and particularly, development of a nucleic acid medicine utilizing the antisense method is actively pushed forward from the viewpoint of high selectivity on target genes, and low toxicity. The antisense method includes a method in which an oligonucleotide complementary to a partial sequence of mRNA (sense strand) of a target gene (e.g., antisense oligonucleotide, i.e., ASO) is introduced into a cell so as to selectively modify or inhibit expression of a protein encoded by the target gene. Similarly, an antisense method also targets miRNA and functions to modify the activity of such miRNA. However, modulation of genes in an ischemic site is not sufficient according to the current nucleic acid medicine such as an antisense nucleic acid or siRNA.

As a nucleic acid utilizing the antisense method, the present inventors have developed a double-stranded nucleic acid complex (heteroduplex oligonucleotide, HDO) formed by annealing an antisense oligonucleotide and a complementary strand thereto (Patent Literature 1, Non-Patent Literatures 1 and 2). The present inventors have also developed a double-stranded antisense nucleic acid having an exon skipping effect (Patent Literature 2), a short gapmer-antisense oligonucleotide in which an additional nucleotide is added to the 5' end, or the 3' end, or both the 5' end and the 3' end of a gapmer (antisense oligonucleotide) (Patent Literature 3), and a double-stranded agent (hetero-chimera-duplex oligonucleotide, HCDO) for delivering a therapeutic oligonucleotide (Patent Literature 4). However, these cited literatures do not disclose at all that expression of a target gene can be modulated in an ischemic site.

CITATION LIST

Patent Literature

Patent Literature 1: International Publication No. WO 2013/089283
Patent Literature 2: International Publication No. WO 2014/203518
Patent Literature 3: International Publication No. WO 2014/132671
Patent Literature 4: International Publication No. WO 2014/192310
Patent Literature 5: International Publication No. WO 2018/062510
Patent Literature 6: International Publication No. WO 2018/056442

Non-Patent Literature

Non-Patent Literature 1: Nishina K, et al., "DNA/RNA heteroduplex oligonucleotide for highly efficient gene silencing", Nature Communication, 2015, 6:7969.
Non-Patent Literature 2: Asami Y, et al., "Drug delivery system of therapeutic oligonucleotides", Drug Discoveries & Therapeutics, 2016; 10(5):256-262.

SUMMARY OF INVENTION

Technical Problem

An object of the present invention is to provide an antisense nucleic acid medicine that can modulate expression of a target transcriptional product in an ischemic site of a subject.

Solution to Problem

To solve the above problem, the present inventors found as a result of intensive studies that by administering an antisense oligonucleotide as a nucleic acid complex with a lipid-conjugated complementary strand to a subject, the nucleic acid complex can be more efficiently delivered to an ischemic site of a subject compared with to a non-ischemic site, so as to more effectively modulate expression of a target transcriptional product in an ischemic site compared with at a non-ischemic site, thereby completing the present invention.

The present invention encompasses the following:

[1] A composition for modulating expression of a target transcriptional product in an ischemic site of a subject, comprising a nucleic acid complex formed by annealing together a first nucleic acid strand comprising an antisense oligonucleotide region with respect to the target transcriptional product, and a lipid-conjugated second nucleic acid strand comprising a complementary region that is complementary to at least part of the first nucleic acid strand.

[2] The composition according to [1] above, wherein the first nucleic acid strand is from 9 to 50 in length.

[3] The composition according to [1] or [2] above, wherein said antisense oligonucleotide region in the first nucleic acid strand is from 9 to 20 base in length.

[4] The composition according to any one of [1] to [3] above, wherein the second nucleic acid strand is from 9 to 50 base in length.

[5] The composition according to any one of [1] to [4] above, wherein said complementary region in the second nucleic acid strand is complementary to at least part of said antisense oligonucleotide region in the first nucleic acid strand.

[6] The composition according to any one of [1] to [5] above, wherein the antisense oligonucleotide region is a gapmer type or mixmer type antisense oligonucleotide region.

[7] The composition according to any one of [1] to [6] above, wherein the lipid is tocopherol or an analog thereof, or cholesterol or an analog thereof.

[8] The composition according to [7] above, wherein the lipid is cholesterol or an analog thereof.

[9] The composition according to any one of [1] to [8] above, wherein the ischemic site is located in a brain, spinal cord, cardiac muscle, skeletal muscle (including upper limb skeletal muscle and lower limb skeletal muscle), blood vessel, lung, kidney, liver, enteric canal, spleen, eye, retina, skin, peripheral nerve, or extremity.

[10] The composition according to any one of [1] to [8] above, wherein the ischemic site is located in the brain, cardiac muscle, or lower limb skeletal muscle.

[11] The composition according to any one of [1] to [10] above for intravenous administration.

[12] The composition according to any one of [1] to [11] above, wherein the modulation of expression of a target transcriptional product is reduction of the amount of the target transcriptional product.

[13] The composition according to any one of [1] to [12] above for administration in an acute phase of ischemia.

[14] The composition according to any one of [1] to [13] above for treating an ischemic disease.

[15] The composition according to [14] above, wherein the ischemic disease is ischemic stroke, myocardial infarction, or arteriosclerosis obliterans.

This description encompasses the disclosures in Japanese Patent Applications No. 2018-051338, and No. 2018-136625, which are the basis for the priority of the present application.

Advantageous Effects of Invention

The present invention provides an antisense nucleic acid medicine that can modulate expression of a target transcriptional product in an ischemic site of a subject.

BRIEF DESCRIPTION OF DRAWINGS

FIG. 1 FIGS. 1A and 1B are each a schematic diagram showing a specific embodiment of the nucleic acid complex according to the present invention.

FIG. 2 FIGS. 2A to 2C are each a schematic diagram showing an example of a specific embodiment of the nucleic acid complex according to the present invention, where the second nucleic acid strand comprises a complementary region and an overhanging region.

FIG. 3 FIGS. 3A and 3B are each a schematic diagram showing an example of a specific embodiment of the nucleic acid complex according to the present invention, where the first nucleic acid strand comprises an antisense oligonucleotide region and a complementary RNA region.

FIG. 7A shows an image of the cerebral hemisphere with ischemic stroke in an ischemic stroke mouse model administered with a lipid-ligand-conjugated double-stranded oligonucleotide labeled with Alexa (Alexa-Toc-HDO). FIG. 7B shows an image of a non-ischemic cerebral hemisphere in an ischemic stroke mouse model administered with Alexa-Toc-HDO. FIG. 7C shows an image of the cerebral hemisphere with ischemic stroke in an ischemic stroke mouse model administered with an Alexa-labeled antisense oligonucleotide (Alexa-ASO).

FIGS. 8A to 8C show respectively an Alexa signal image, a DAPI signal image, and an overlaid image of the cerebral hemisphere with ischemic stroke in an ischemic stroke mouse model administered with Alexa-Toc-HDO. FIGS. 8D to 8F show respectively an Alexa signal image, a DAPI signal image, and an overlaid image of the cerebral hemisphere with ischemic stroke in an ischemic stroke mouse model administered with Alexa-ASO.

FIG. 9A shows the oligonucleotide amounts in the cerebral hemisphere with ischemic stroke, and the non-ischemic cerebral hemisphere. FIG. 9B shows the oligonucleotide amounts in the liver.

FIGS. 10A to 10C show respectively an Alexa signal image, a CD31 signal (vascular endothelial cell marker) image, and an overlaid image in the cerebral hemisphere with ischemic stroke of an ischemic stroke mouse model administered with Alexa-Toc-HDO. FIG. 10D to 1° F. show respectively an Alexa signal image, a NeuN signal (neuronal cell marker) image, and an overlaid image in the cerebral hemisphere with ischemic stroke of an ischemic stroke mouse model administered with Alexa-Toc-HDO.

FIG. 12A shows an ischemic stroke site in an ischemic stroke mouse model administered with PBS. FIG. 12B shows an ischemic stroke site in an ischemic stroke mouse model administered with Toc-HDO.

FIG. 13A shows ischemic stroke volume. FIG. 13B shows cerebral blood flow. FIG. 13C shows motor function.

FIG. 14A is an image of a myocardial infarction site in a myocardial infarction mouse model administered with Alexa-Toc-HDO. FIG. 14B is an image of a myocardial infarction site in a myocardial infarction mouse model administered with Alexa-ASO. FIG. 14C is an image of a normal cardiac muscle in a mouse administered with Alexa-Toc-HDO.

FIGS. 15A to 15C show respectively an Alexa signal image, a CD31 signal image, and an overlaid image of a non-infarcted site in a myocardial infarction mouse model administered with Alexa-Toc-HDO. FIGS. 15D to 15F show respectively an Alexa signal image, a CD31 signal image, and an overlaid image of a myocardial infarction site in a myocardial infarction mouse model administered with Alexa-Toc-HDO.

FIGS. 16A to 16C show respectively an Alexa signal image, a CD31 signal image, and an overlaid image of a myocardial infarction site in a myocardial infarction mouse model administered with Alexa-Toc-HDO. FIGS. 16D to 16F also show respectively an Alexa signal image, a CD31 signal image, and an overlaid image of a similar site.

FIG. 17A shows a healthy lower limb skeletal muscle. FIG. 17B shows an ischemic lower limb skeletal muscle.

FIG. 18A is an image of a lower limb ischemic site in an arteriosclerosis obliterans mouse model administered with Alexa-Toc-HDO. FIG. 18B is an image of a lower limb non-ischemic site in an arteriosclerosis obliterans mouse model administered with Alexa-Toc-HDO. FIG. 18C is an image of a lower limb ischemic site in an arteriosclerosis obliterans mouse model administered with Alexa-ASO.

FIGS. 19A to 19D show respectively an Alexa signal image, a CD31 signal image, a DAPI signal image, and an overlaid image of a lower limb ischemic site of an arteriosclerosis obliterans mouse model administered with Alexa-Toc-HDO.

FIG. 21 shows graphs showing the results of Example 10, in which upregulation of lipid receptors expression in an acute phase of ischemic stroke was examined at the mRNA level. FIG. 21A shows the results on LDLR (LDL receptor). FIG. 21B shows the results on SRBI. FIG. 21C shows the results on LRP1.

FIGS. 23A to 23C show respectively an LDLR signal image, a CD31 signal image, and an overlaid image in a sham-operated mouse. FIGS. 23D to 23F show respectively an LDLR signal image, a CD31 signal image, and an overlaid image at 6 hours after artery occlusion. The white bars indicate 50 μm.

FIGS. 24A to 24C show respectively an SRBI signal image, a CD31 signal image, and an overlaid image in a sham-operated mouse. FIGS. 24D to 24F show respectively an SRBI signal image, a CD31 signal image, and an overlaid image at 6 hours after artery occlusion. The white bars indicate 50 μm.

FIGS. 25A to 25C show respectively a LPR1 signal image, a NeuN signal image, and an overlaid image in a sham-operated mouse. FIGS. 25D to 25F show respectively a LPR1 signal image, a NeuN signal image, and an overlaid image at 6 hours after artery occlusion. The white bars indicate 50 μm.

FIG. 26A shows photographs of the brains of ischemic stroke model mice (wildtype and LDLR knockout) in which Evans Blue was administered intravenously. FIG. 26B is a graph showing the Evans Blue positive areas in the brain shown in FIG. 26A.

FIG. 30A shows the oligonucleotide amounts in an ischemic site, and a non-ischemic site in the cardiac muscle. FIG. 30B shows the oligonucleotide amounts in the liver.

FIG. 32A shows the results on LDLR (LDL receptor). FIG. 32B shows the results on LRP1. FIG. 32C shows the results on SRBI.

FIG. 34-1 shows fluorescence microscope images showing the results of Example 20, in which an increased expression of the lipid receptor LDLR in arteriosclerosis obliterans was confirmed by immunofluorescent staining. FIGS. 34-1A to 34-1C show respectively an LDLR signal image, a CD31 signal image, and an overlaid image of the lower limb gastrocnemial muscle (ischemic site) at 6 hours after ischemia. FIGS. 34-1D to 34-1F show respectively an LDLR signal image, a CD31 signal image, and an overlaid image of the lower limb gastrocnemial muscle (normal site).

FIG. 34-2 shows fluorescence microscope images showing the results of Example 20, in which an increased expression of the lipid receptor SRBI in arteriosclerosis obliterans was confirmed by immunofluorescent staining. FIGS. 34-2A to 34-2C show respectively an SRBI signal image, a CD31 signal image, and an overlaid image of the lower limb gastrocnemial muscle (ischemic site) at 6 hours after ischemia. FIGS. 34-2D to 34-2F show respectively an SRBI signal image, a CD31 signal image, and an overlaid image of the lower limb gastrocnemial muscle (normal site).

DESCRIPTION OF EMBODIMENTS

The present invention is described in detail below.
<Nucleic Acid Complex>

According to the present invention, a nucleic acid complex in which a first nucleic acid strand and a second nucleic acid strand comprising (or consisting of) a complementary region that is complementary to at least part of the first nucleic acid strand are annealed via hydrogen bonds of complementary base pairs. The nucleic acid complex has a double-stranded structure resulting from the annealing of a first nucleic acid strand with a second nucleic acid strand. It is not necessary that all of the first nucleic acid strand and all of the second nucleic acid strand are annealed: a part of the first nucleic acid strand and all of the second nucleic acid strand may be annealed, or all of the first nucleic acid strand and a part of the second nucleic acid strand may be annealed. Alternatively, a part of the first nucleic acid strand and a part of the second nucleic acid strand may be annealed.

The first nucleic acid strand is a nucleotide strand comprising or consisting of an antisense oligonucleotide region with respect to a target transcriptional product. An "antisense oligonucleotide" or an "antisense nucleic acid" means a single-stranded oligonucleotide which comprises a base sequence that is capable of hybridizing (namely complementary) to at least part of a target transcriptional product (primarily a transcriptional product of a target gene), and is able to produce an antisense effect on a target transcriptional product. According to the present invention, the antisense oligonucleotide region in the first nucleic acid strand can produce an antisense effect on a target transcriptional product.

Figure 4:
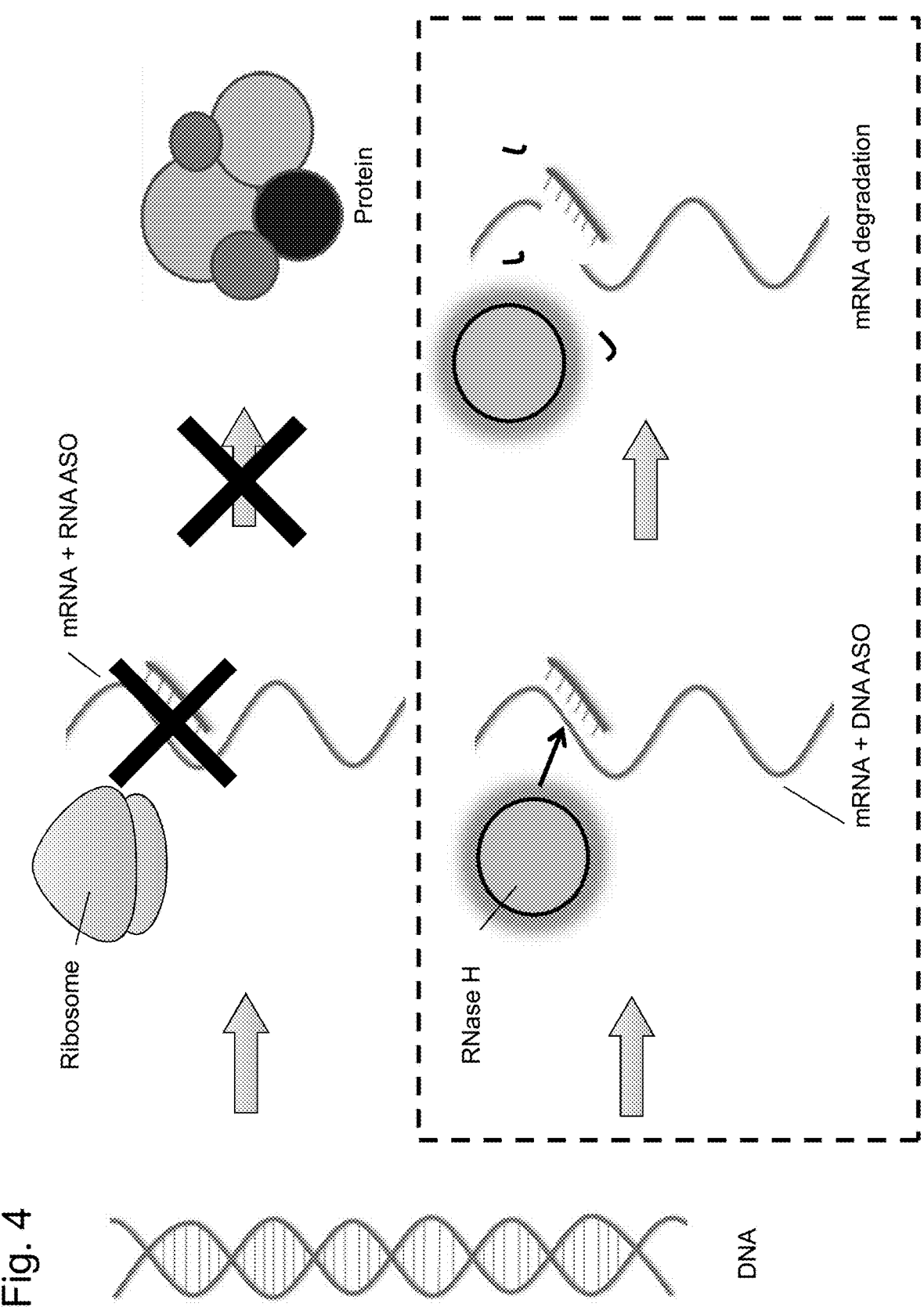
FIG. 4 is a diagram showing an example of a general mechanism of the antisense method.

The "antisense effect" means the modulation of expression of a target transcriptional product, which results from hybridization of the target transcriptional product (RNA sense strand) with a strand (e.g. DNA strand) that is complementary to a partial sequence of a transcriptional product or the like and is designed to produce an antisense effect. The modulation of expression of a target transcriptional product comprises inhibition or reduction of expression of a target gene or the level (expression amount) of a target transcriptional product, or in a certain example inhibition of translation or splicing function modification effect such as exon skipping, or degradation of a transcriptional product (see FIG. 4). For example, in the case of inhibition of translation, when an oligonucleotide comprising RNA is introduced into a cell as an antisense oligonucleotide (ASO), the ASO binds to a transcriptional product (mRNA) of the target gene to form a partial double strand. This partial double strand serves as a cover to prevent translation by a ribosome, and thus expression of a protein encoded by the target gene is inhibited on the translational level (FIG. 4, x mark outside the dashed line box). Meanwhile, when an oligonucleotide comprising DNA is introduced into a cell as ASO, a partial DNA-RNA heteroduplex is formed. This heteroduplex structure is recognized by RNase H, and as a result mRNA of the target gene is degraded, and consequently expression of a protein encoded by the target gene is inhibited at the expression level (FIG. 4, inside the dashed line box). This is called "RNase H-dependent pathway". Further, in a certain example, an antisense effect may also be brought about by targeting an intron of an mRNA precursor. An antisense effect can also be brought about by targeting miRNA, and in this case the function of the miRNAs is inhibited, and expression of a gene whose expression is normally regulated by the miRNA may be increased. In an embodiment, the modulation of expression of a target transcriptional product may be reduction of the amount of the target transcriptional product.

Although there is no particular restriction on the "target gene" whose expression is modulated (for example, inhibited, altered, or modified) by an antisense effect, examples thereof include a gene derived from an organism to which a nucleic acid complex according to the present invention is introduced, such as a gene whose expression increases in an ischemic disease, and a gene whose expression inhibition produces improvement of an ischemic disease, and more specifically AIF (apoptosis inducing factor), caspase, TNF-α, RIPK1 (receptor-interacting serine/threonine kinase 1), E-selectin, ICAM-1, MCP-1, IL-1, and IL-6. A "transcriptional product of a target gene" refers to an mRNA transcribed from the genomic DNA encoding the target gene, and also includes mRNAs without base modification, an unprocessed mRNA precursor, or the like. A "target transcriptional product" may include not only an mRNA, but also a non-coding RNA (ncRNA) such as a miRNA. Further, in general, a transcriptional product may be any RNA synthesized by a DNA-dependent RNA polymerase.

In an embodiment, a "target transcriptional product" may be, for example, a non-coding RNA of a metastasis associated lung adenocarcinoma transcript 1 (Malat-1). The base sequences of murine and human Malat-1 non-coding RNA are shown respectively in SEQ ID NOs: 1 and 2, (base sequence of RNA is shown as base sequence of DNA). The base sequences of genes and transcriptional products are available from public databases, such as NCBI (U.S. National Center for Biotechnology Information) database.

The antisense oligonucleotide region in the first nucleic acid strand comprises a base sequence that can hybridize to at least part of a target transcriptional product (for example, any target region). The target region may comprise a 3' UTR, a 5' UTR, an exon, an intron, a coding region, a translation initiation region, a translation termination region, or any other nucleic acid region. The target region of a target transcriptional product may comprise, for example, the base sequence of position 1317 to 1332 of SEQ ID NO: 1 in the case of murine Malat-1 non-coding RNA.

The term "nucleic acid" or "nucleic acid molecule" as used herein may refer to a monomer of a nucleotide or a nucleoside, or may mean an oligonucleotide consisting of a plurality of monomers. The term "nucleic acid strand" or "strand" is also used herein to refer to an oligonucleotide. A nucleic acid strand can be produced as a full-length strand, or a partial strand by a chemical synthesis method (for example, with an automated synthesis apparatus) or by an enzymatic process (for example, but not limited to, by a polymerase, ligase, or a restriction reaction).

The term "nucleobase" or "base" as used herein means a base component (heterocyclic moiety) constituting a nucleic acid, and primarily adenine, guanine, cytosine, thymine, and uracil are known.

The term "complementary" as used herein means a relationship in which nucleobases can form so-called Watson-Crick base pairs (natural type base pair), or non-Watson-Crick base pairs (such as Hoogsteen type base pairs) via hydrogen bonds. In the present invention, it is not necessarily required that the antisense oligonucleotide region in the first nucleic acid strand is completely complementary to at least a part of a target transcriptional product (e.g., the transcriptional product of a target gene), but it is tolerated if the base sequence has a complementarity of at least 70%, preferably at least 80%, and more preferably at least 90% (e.g., 95%, 96%, 97%, 98%, or 99% or more). An antisense oligonucleotide region in the first nucleic acid strand can hybridize to a target transcriptional product, when the base sequence is complementary (typically, when the base sequence is complementary to at least part of the base sequence of the target transcriptional product). Similarly, it is not necessarily required that the complementary region in the second nucleic acid strand is completely complementary to at least part of the first nucleic acid strand, but it is tolerated if the base sequence has a complementarity of at least 70%, preferably at least 80%, and more preferably at least 90% (e.g., 95%, 96%, 97%, 98%, or 99% or more). When the base sequence of the complementary region in the second nucleic acid strand is complementary to at least part of the first nucleic acid strand, the region can be annealed thereto. The complementarity of a base sequence can be determined using a BLAST program or the like. One skilled in the art can easily determine the conditions (temperature, salt concentration, etc.) under which two strands can be annealed or hybridized to each other, taking into account the complementarity between the strands. Further, one skilled in the art can easily design an antisense nucleic acid that is complementary to the target transcriptional product based on, for example, information on the base sequence of a target gene.

Hybridization conditions may be a variety of stringent conditions, such as a low-stringent condition and a high-stringent condition. A low-stringent condition may be a condition with a relatively low temperature and a high salt concentration, such as 30° C., 2×SSC, and 0.1% SDS. A high-stringent condition may be a condition with a relatively high temperature and a low salt concentration, such as 65° C., 0.1×SSC, and 0.1% SDS. The stringency of hybridization can be adjusted by varying the conditions, such as temperature and salt concentration. Here, 1×SSC contains 150 mM of sodium chloride and 15 mM of sodium citrate.

The antisense oligonucleotide region in the first nucleic acid strand may be usually, but not particularly limited to, at least 8 bases in length, at least 9 bases in length, at least 10 bases in length, at least 11 bases in length, at least 12 bases in length, or at least 13 bases in length. The antisense oligonucleotide region in the first nucleic acid strand may be 35 bases in length or less, 30 bases in length or less, 25 bases in length or less, 24 bases in length or less, 23 bases in length or less, 22 bases in length or less, 21 bases in length or less, 20 bases in length or less, 19 bases in length or less, 18 bases in length or less, 17 bases in length or less, or 16 bases in length or less. The antisense oligonucleotide region in the first nucleic acid strand may be, for example, from 8 to 35 bases in length, from 9 to 30 bases in length, from 10 to 25 bases in length, from 10 to 20 bases in length, from 11 to 18 bases in length, or 12 to 16 bases in length.

Although there is no particular restriction, the first nucleic acid strand may be at least 9 bases in length, at least 10 bases in length, at least 11 bases in length, at least 12 bases in length, or at least 13 bases in length. The first nucleic acid strand may be 50 bases in length or less, 45 bases in length or less, 40 bases in length or less, 35 bases in length or less, 30 bases in length or less, 28 bases in length or less, 26 bases in length or less, 24 bases in length or less, 22 bases in length or less, 20 bases in length or less, 18 bases in length or less, or 16 bases in length or less. The first nucleic acid strand may be, for example, from 9 to 50 bases in length, from 10 to 40 bases in length, from 11 to 35 bases in length, or from 12 to 30 bases in length.

The complementary region in the second nucleic acid strand may be usually, but not limited to, at least 9 bases in length, at least 10 bases in length, at least 11 bases in length, at least 12 bases in length, or at least 13 bases in length. The complementary region in the second nucleic acid strand may be 35 bases in length or less, 30 bases in length or less, 25 bases in length or less, 24 bases in length or less, 23 bases in length or less, 22 bases in length or less, 21 bases in length or less, 20 bases in length or less, 19 bases in length or less, 18 bases in length or less, 17 bases in length or less, or 16 bases in length or less. The complementary region in the second nucleic acid strand may be, for example, from 9 to 35 bases in length, from 9 to 30 bases in length, from 10 to 25 bases in length, from 10 to 20 bases in length, from 11 to 18 bases in length, or from 12 to 16 bases in length.

Although there is no particular restriction, the second nucleic acid strand may be at least 9 bases in length, at least 10 bases in length, at least 11 bases in length, at least 12 bases in length, or at least 13 bases in length. The second nucleic acid strand may be 50 bases in length or less, 45 bases in length or less, 40 bases in length or less, 35 bases in length or less, 30 bases in length or less, 28 bases in length or less, 2 bases in length or less, 24 bases in length or less, 22 bases in length or less, 20 bases in length or less, 18 bases in length or less, or 16 bases in length or less. The second nucleic acid strand may be, for example, from 9 to 50 bases in length, from 10 to 40 bases in length, from 11 to 35 bases in length, or from 12 to 30 bases in length. The length is generally selected especially according to the balance between the strength of the antisense effect and the specificity of the nucleic acid strand with respect to the target among other factors, such as cost, and synthesis yield.

The second nucleic acid strand comprises or consists of a complementary region that is complementary to at least part of the first nucleic acid strand.

Figure 1:
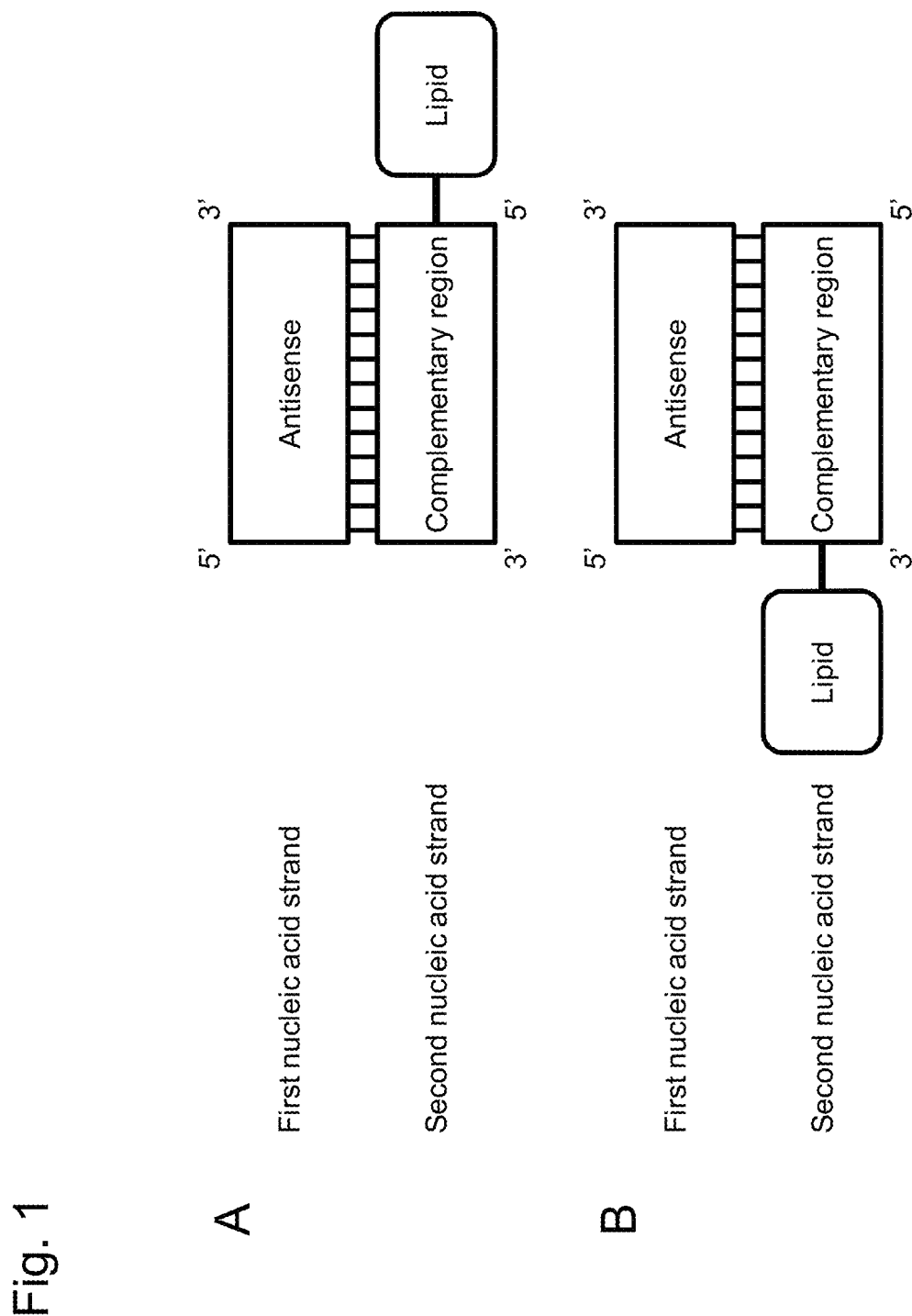

In an embodiment, the complementary region in the second nucleic acid strand may be complementary to at least part of the antisense oligonucleotide region in the first nucleic acid strand. The complementary region in the second nucleic acid strand may be complementary to all of the antisense oligonucleotide region in the first nucleic acid strand. The complementary region in the second nucleic acid strand may be complementary also to a part of the first nucleic acid strand other than the antisense oligonucleotide region, in addition to the antisense oligonucleotide region. As an example of this embodiment there is a heteroduplex oligonucleotide (HDO) as disclosed in International Publication No. WO 2013/089283, Nishina K., et al. Nature Communication, 2015, 6:7969, or Asami Y., et al. Drug Discoveries & Therapeutics, 2016; 10(5):256-262 (FIGS. 1A and 1B).

In a further embodiment, the second nucleic acid strand may further comprise at least one overhanging region located on either or both of the 5' end side and the 3' end side of the complementary region. An example of this embodiment is described in PCT/JP2017/035553. An "overhanging region" refers to a region adjacent to the complementary region, where the 5' end of the second nucleic acid strand extends beyond the 3' end of the first nucleic acid strand, and/or the 3' end of the second nucleic acid strand extends beyond the 5' end of the first nucleic acid strand, when the first nucleic acid strand and the second nucleic acid strand anneal to form a double-stranded structure. In other words, it means nucleotide region(s) in the second nucleic acid strand, protruded from the double-stranded structure. The overhanging region in the second nucleic acid strand may be located on the 5' end side of the complementary region (FIG. 2A), or on the 3' end side (FIG. 2B). The overhanging regions in the second nucleic acid strand may be located on the 5' end side and the 3' end side of the complementary region (FIG. 2C).

In general, a "nucleoside" is a combination of a base and a sugar. The nucleobase moiety (also known as a base) of a nucleoside is usually a heterocyclic base moiety. A "nucleotide" further comprises a phosphate group covalently bonded to the sugar moiety of the nucleoside. In a nucleoside comprising a pentofuranosyl sugar, a phosphate group is can be linked to the 2', 3', or 5' hydroxyl portion of the sugar. An oligonucleotide is formed by contiguous nucleosides linked to each other by a covalent bond, forming a linear polymer oligonucleotide. Inside the oligonucleotide structure, it is considered that a phosphate group generally forms an internucleoside bond in the oligonucleotide.

A nucleic acid strand can comprise a natural nucleotide and/or a non-natural nucleotide. A "natural nucleotide" includes deoxyribonucleotide found in DNA and ribonucleotide found in RNA. The "deoxyribonucleotide" and "ribonucleotide" may be also occasionally referred to as "DNA nucleotide" and "RNA nucleotide", respectively.

Similarly, a "natural nucleoside" includes deoxyribonucleoside found in DNA and ribonucleoside found in RNA. The "deoxyribonucleoside" and "ribonucleoside" may be also occasionally referred to as "DNA nucleoside" and "RNA nucleoside," respectively.

A "non-natural nucleotide" refers to any nucleotide other than natural nucleotide and includes a modified nucleotide or a nucleotide mimic. Similarly, a "non-natural nucleoside" refers to any nucleoside other than natural nucleoside, and includes a modified nucleoside, or a nucleoside mimic. A "modified nucleotide" means a nucleotide comprising one or more of a modified sugar moiety, a modified internucleoside bond, and a modified nucleobase. A "modified nucleoside" means a nucleoside having a modified sugar moiety and/or a modified nucleobase. A nucleic acid strand comprising a non-natural oligonucleotide is in many cases more preferable than a natural type, because of such desirable characteristics as enhanced cellular uptake, enhanced affinity for a nucleic acid target, increased stability in the presence of a nuclease, or increased inhibitory activity.

The term "modified internucleoside bond" refers to an internucleoside bond having a substitution or any change from a naturally occurring internucleoside bond (i.e., phosphodiester bond). The modified internucleoside bond includes an internucleoside bond comprising a phosphorus atom, and an internucleoside bond not comprising a phosphorus atom. Examples of a typical phosphorus-containing internucleoside bond include, but not limited to, a phosphodiester bond, a phosphorothioate bond, a phosphorodithioate bond, a phosphotriester bond, a methylphosphonate bond, a methylthiophosphonate bond, a boranophosphate bond, and a phosphoramidate bond. A phosphorothioate bond refers to an internucleoside bond in which a non-bridging oxygen atom of a phosphodiester bond is replaced with a sulfur atom. A method for preparing a phosphorus-containing bond or a phosphorus-free bond is well known. A modified internucleoside bond is preferably a bond whose nuclease resistance is higher than a naturally occurring internucleoside bond.

A "modified nucleobase" or a "modified base" means any nucleobase other than adenine, cytosine, guanine, thymine, or uracil. An "unmodified nucleobase" or an "unmodified base" (natural nucleobase) means adenine (A) and guanine (G), which are purine bases, as well as thymine (T), cytosine (C), and uracil (U), which are pyrimidine bases. Examples of a modified nucleobase include, but not limited to, 5-methylcytosine, 5-fluorocytosine, 5-bromocytosine, 5-iodocytosine, or N4-methylcytosine; N6-methyladenine or 8-bromoadenine; and N2-methylguanine or 8-bromoguanine. A modified nucleobase is preferably 5-methylcytosine.

The term "modified sugar" refers to a sugar having a substitution and/or any change from a natural sugar moiety (i.e., a sugar moiety found in DNA(2'-H) or RNA(2'-OH)). A nucleic acid strand may, in some cases, comprise one or more modified nucleoside including a modified sugar. Such a sugar-modified nucleoside can confer beneficial biological properties, such as an enhanced nuclease stability, an increased binding affinity, or the like to a nucleic acid strand. In a certain embodiment, a nucleoside comprises a chemically modified ribofuranose ring moiety. Examples of a chemically modified ribofuranose ring include, but not limited to, addition of a substituent (including 5' or 2' substituent), formation of a bicyclic nucleic acid (bridged nucleic acid, BNA) by forming a bridge between non-geminal ring atoms, and substitution of a ribosyl ring oxygen atom with S, N(R), or C(R1)(R2) (wherein R, R1 and R2 each independently represents H, a $C_1$ to $C_{12}$ alkyl, or a protective group), and a combination thereof.

Examples of a nucleoside having a modified sugar moiety include, but not limited to, a nucleoside having a substituent, such as 5'-vinyl, 5'-methyl(R or S), 4'-S, 2'-F (2'-fluoro group), 2'-OCH$_3$ (2'-OMe group, or 2'-O-methyl group), and 2'-O(CH$_2$)$_2$OCH$_3$. A substituent at the 2' position may be selected from allyl, amino, azide, thio, —O-allyl, —O—$C_1$-$C_{10}$ alkyl, —OCF$_3$, —O(CH$_2$)$_2$SCH$_3$, —O(CH$_2$)$_2$—O—N(Rm)(Rn), and —O—CH$_2$—C(=O)—N(Rm)(Rn), wherein each Rm and Rn is independently H or a substituted or unsubstituted $C_1$-$C_{10}$ alkyl. A "2'-modified sugar" means a furanosyl sugar modified at the 2' position.

The term "bicyclic nucleoside" refers to a modified nucleoside comprising a bicyclic sugar moiety. A nucleic acid comprising a bicyclic sugar moiety is generally referred to as bridged nucleic acid (BNA). A nucleoside comprising a bicyclic sugar moiety is sometimes referred to as "bridged nucleoside".

A bicyclic sugar may be a sugar in which the carbon atom at the 2' position and the carbon atom at the 4' position are bridged via two or more atoms. Examples of a bicyclic sugar are known to those skilled in the art. A subgroup of nucleic acid comprising a bicyclic sugar (BNA) may be described as having a carbon atom at the 2' position and a carbon atom at the 4' position bridged by 4'-$(CH_2)_p$—O-2', 4'-$(CH_2)_p$—$CH_2$-2', 4'-$(CH_2)$p-S-2', 4'-$(CH_2)_p$—OCO-2', or 4'-$(CH_2)_n$—N($R_3$)—O—$(CH_2)_m$-2' [in the formula, p, m, and n respectively represent integers of 1 to 4, 0 to 2, and 1 to 3; and $R_3$ represents a hydrogen atom, an alkyl group, an alkenyl group, a cycloalkyl group, an aryl group, an aralkyl group, an acyl group, a sulfonyl group, or a unit substituent (such as a fluorescently or chemiluminescently labeled molecule, a functional group having nucleic acid cleavage activity, and intracellular or intranuclear localization signal peptide)]. Further, regarding the BNA according to a specific embodiment, in an $OR_2$ substituent on the carbon atom at the 3' position and an OR' substituent on the carbon atom at the 5' position, $R_1$ and $R_2$ are typically a hydrogen atom, but they may be the same or different, and further may be a protecting group for a hydroxyl group for nucleic acid synthesis, an alkyl group, an alkenyl group, a cycloalkyl group, an aryl group, an aralkyl group, an acyl group, a sulfonyl group, a silyl group, a phosphate group, a phosphate group protected by a protecting group for nucleic acid synthesis, or —P($R_4$)$R_5$ [where $R_4$ and $R_5$ may be the same or different, and respectively may be a hydroxyl group, a hydroxyl group protected by a protecting group for nucleic acid synthesis, a mercapto group, a mercapto group protected by a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms]. Non-restrictive examples of such BNA include methyleneoxy (4'-$CH_2$—O-2') BNA (LNA (Locked Nucleic Acid®, also known as 2',4'-BNA), e.g., α-L-methyleneoxy (4'-$CH_2$—O-2') BNA, or β-D-methyleneoxy (4'-$CH_2$—O-2') BNA, ethyleneoxy (4'-$(CH_2)_2$—O-2') BNA (also known as ENA), β-D-thio (4'-$CH_2$—S-2') BNA, aminooxy (4'-$CH_2$—O—N($R_3$)-2') BNA, oxyamino (4'-$CH_2$—N($R_3$)—O-2') BNA (also known as 2',4'-BNA$^{NC}$), 2',4'-BNA$^{coc}$, 3'-amino-2',4'-BNA, 5'-methyl BNA, (4'-CH(CH$_3$)—O-2') BNA (also known as cEt BNA), (4'-CH(CH$_2$OCH$_3$)—O-2')BNA (also known as cMOE BNA), amide BNA (4'-C(O)—N(R)-2') BNA (R═H, Me) (also known as AmNA), 2'-O,4'-C-spirocyclopropylene bridged nucleic acid (also known as scpBNA), and other BNAs known to those skilled in the art.

A bicyclic nucleoside having a methyleneoxy (4'-$CH_2$—O-2') bridge is sometimes referred to as LNA nucleoside.

The method for preparing a modified sugar is well known to those skilled in the art. In a nucleotide having a modified sugar moiety, the nucleobase moiety (natural one, modified one, or a combination thereof) may be maintained for hybridization with an appropriate nucleic acid target.

Figure 5:
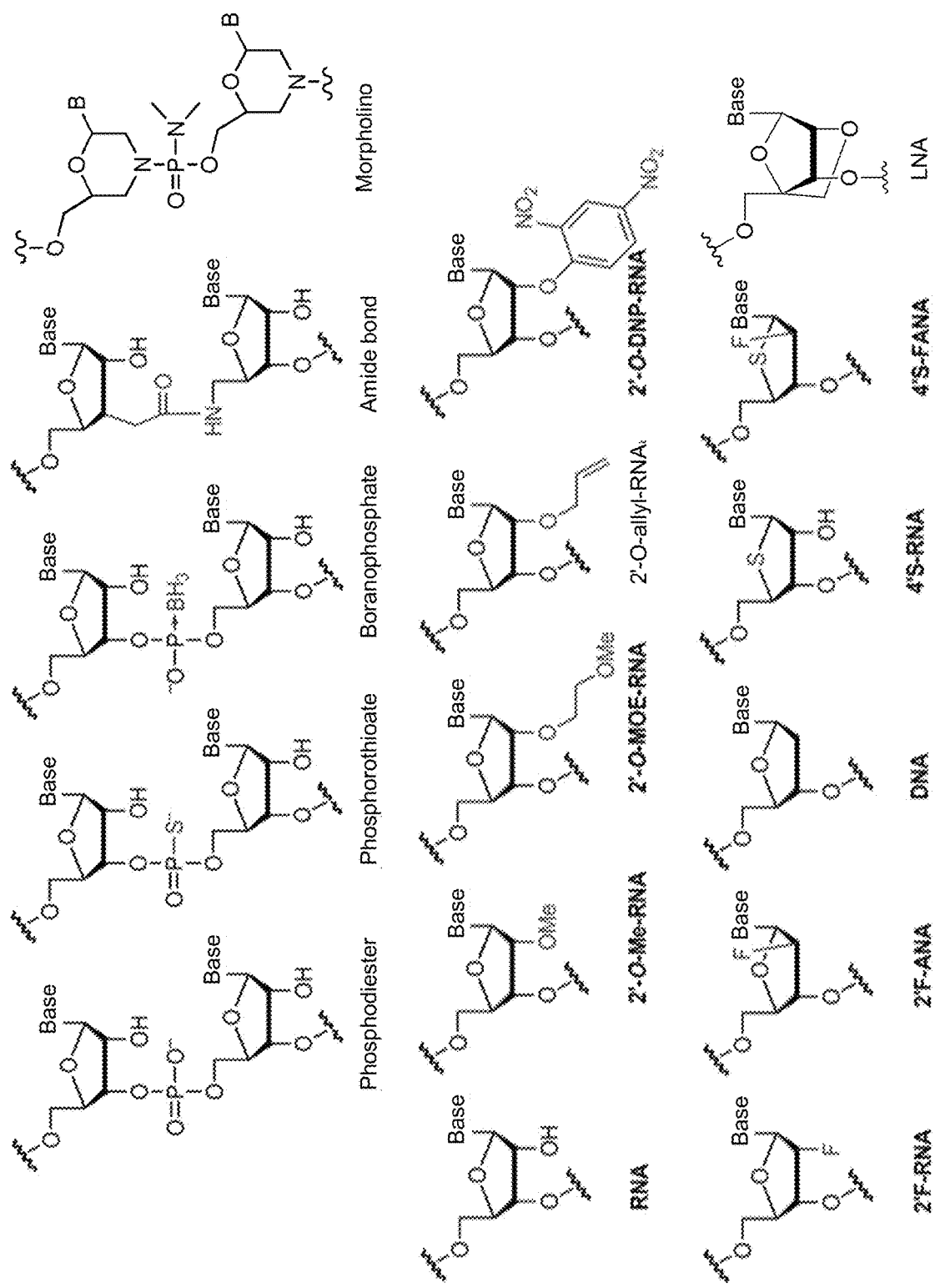
FIG. 5 is a diagram showing the structures of various natural nucleotides or non-natural nucleotides.

The "nucleoside mimic" includes a structure used for replacing a sugar, or a sugar and a base, and, but not mandatorily, a bond at one or more positions of an oligomeric compound. The term "oligomeric compound" means a polymer of linked monomeric subunits capable of hybridizing to at least a region of a nucleic acid molecule. Example of a nucleoside mimic include, for example, morpholino, cyclohexenyl, cyclohexyl, tetrahydropyranyl, bicyclic or tricyclic sugar mimic, e.g., a nucleoside mimic having a non-furanose sugar unit. The "nucleotide mimic" includes a structure used for replacing a nucleoside and a bond at one or more positions of an oligomeric compound. Examples of a nucleotide mimic include a peptide nucleic acid, and a morpholino nucleic acid (a morpholino linked by —N(H)—C(═O)—O— or other non-phosphodiester bonds). A peptide nucleic acid (PNA) is a nucleotide mimic having a main chain in which N-(2-aminoethyl)glycine in place of a sugar is linked by an amide bond. An example of the structure of a morpholino nucleic acid is shown in FIG. 5. A "mimic" refers to a group that replaces one or more of a sugar, a nucleobase, and an internucleoside bond. In general, a mimic is used in place of a sugar or a combination of sugar and an internucleoside bond, and a nucleobase is maintained for hybridization to a selected target.

In general, modifications can be performed such that nucleotides in the same strand can independently undergo different modifications. In addition, to confer resistance to enzymatic cleavage, the same nucleotide may have a modified internucleoside bond (e.g., phosphorothioate bond), and also have a modified sugar (e.g., 2'-O-methyl modified sugar, or bicyclic sugar). Further, the same nucleotide can have a modified nucleobase (e.g., 5-methylcytosine) and further have a modified sugar (e.g., 2'-O-methyl modified sugar, or bicyclic sugar).

The number, type, and position of a non-natural nucleotide in a nucleic acid strand can influence the antisense effect or the like provided by a nucleic acid complex. Selection of a modification may vary depending on the sequence of a target gene or the like, but one skilled in the art can determine a suitable embodiment by referring to the description of literatures related to the antisense method (for example, WO 2007/143315, WO 2008/043753, and WO 2008/049085). Furthermore, when the antisense effect of the nucleic acid complex after the modification is measured, if the measurement value thus obtained is not significantly lower than the measurement value of the nucleic acid complex before the modification (for example, in a case where the measurement value obtained after the modification are 70% or more, 80% or more, or 90% or more of the measurement value of the nucleic acid complex before the modification), a relevant modification can be evaluated.

Measurement of an antisense effect may be performed, for example, by administering a test nucleic acid compound to a subject (e.g., mouse), and measuring the expression amount of a target gene whose expression is modulated by the antisense effect provided by the test nucleic acid compound, or the level (amount) of the target transcriptional product (for example, the amount of mRNA, or the amount of RNA such as microRNA, the amount of cDNA, or the amount of protein), for example, several days after the administration (for example, after 2 to 7 days).

For example, in a case where the expression amount of a target gene, or the level of a target transcriptional product measured as above is reduced by at least 10%, at least 20%, at least 25%, at least 30%, or at least 40% compared to the negative control (e.g., vehicle administration), it is demonstrated that the test nucleic acid compound can produce an antisense effect (e.g., reduction of target transcriptional product amount).

The internucleoside bond in the first nucleic acid strand may be a naturally occurring internucleoside bond and/or a modified internucleoside bond.

At least one, at least two, or at least three internucleoside bonds from the 5' end of the first nucleic acid strand may be modified internucleoside bonds. At least one, at least two, or at least three internucleoside bonds from the 3' end of the first nucleic acid strand may be modified internucleoside bonds. For example, two internucleoside bonds from an end of a nucleic acid strand refers to an internucleoside bond closest to the end of the nucleic acid strand, and an internucleoside bond positioned next thereto in the direction opposite to the end of the nucleic acid strand. Modified internucleoside bond(s) at the terminal region of a nucleic acid strand are preferred because they can reduce or inhibit undesired degradation of the nucleic acid strand.

Modified internucleoside bond(s) may be at least 70%, at least 80%, at least 85%, at least 90%, at least 93%, at least 95%, at least 98%, or 100% of the internucleoside bonds of the antisense oligonucleotide region in the first nucleic acid strand. A modified internucleoside bond may be a phosphorothioate bond.

The nucleoside in the first nucleic acid strand may be a natural nucleoside (including deoxyribonucleoside, ribonucleoside, or both) and/or a non-natural nucleoside.

The antisense oligonucleotide region in the first nucleic acid strand may be an antisense oligonucleotide region of a gapmer type (a gapmer type antisense oligonucleotide region). A "gapmer type" refers to a nucleoside configuration consisting of a central region (DNA gap region) comprising at least four contiguous deoxyribonucleosides, and regions (5' wing region, and 3' wing region) which comprise non-natural nucleosides and are located respectively on the 5' end side and the 3' end side of the central region. A gapmer in which a non-natural nucleoside is constituted by a bridged nucleoside is specifically referred to as "BNA/DNA gapmer". The length of the DNA gap region may be 4 to 20 bases in length, 5 to 18 bases in length, 6 to 16 bases in length, 7 to 14 bases in length, or 8 to 12 bases in length. The lengths of the 5' wing region and the 3' wing region may independently be usually 1 to 10 bases in length, 1 to 7 bases in length, 2 to 5 bases in length, or 2 to 3 bases in length. It is permissible if the 5' wing region and the 3' wing region comprise at least one non-natural nucleoside, and the 5' wing region and the 3' wing region may additionally comprise a natural nucleoside. A gapmer type antisense oligonucleotide region may have a nucleoside configuration of BNA/DNA gapmer type comprising a 5' wing region comprising two or three bridged nucleosides, a 3' wing region comprising two or three bridged nucleosides, and a DNA gap region therebetween. The bridged nucleoside may comprise a modified nucleobase (e.g., 5-methylcytosine). Further, the gapmer may be a "LNA/DNA gapmer" in which the bridged nucleoside is constituted by a LNA nucleoside.

The antisense oligonucleotide region in the first nucleic acid strand may be an antisense oligonucleotide region of a mixmer type (a mixmer type antisense oligonucleotide region). A "mixmer type" refers to a nucleoside configuration alternatingly comprises natural nucleosides (deoxyribonucleoside and/or ribonucleoside) and non-natural nucleosides having periodic or random segment lengths, and does not comprise four or more contiguous deoxyribonucleosides, nor four or more contiguous ribonucleosides. It is not necessarily required that a mixmer comprises only two kinds of nucleosides. A mixmer may comprise any number of kinds of nucleosides, irrespective of a natural or modified nucleoside, or a nucleoside mimic. For example, a mixmer may have one or two contiguous deoxyribonucleosides separated by a bridged nucleoside (for example, LNA nucleoside).

The first nucleic acid strand may comprise entirely or partly a nucleoside mimic or a nucleotide mimic. A nucleotide mimic may be a peptide nucleic acid and/or a morpholino nucleic acid. The first nucleic acid strand may comprise at least one modified nucleoside. The modified nucleoside may comprise a 2'-modified sugar. The 2'-modified sugar may be a sugar that comprises a 2'-O-methyl group.

An internucleoside bond in the second nucleic acid strand may be a naturally occurring internucleoside bond and/or a modified internucleoside bond.

All of the internucleoside bonds in the second nucleic acid strand may be modified internucleoside bonds. Alternatively, all of the internucleoside bonds in the second nucleic acid strand may be natural internucleoside bonds.

At least one, at least two, or at least three internucleoside bonds from the 5' end of the second nucleic acid strand may be modified internucleoside bonds. At least one, at least two, or at least three internucleoside bonds from the 3' end of the second nucleic acid strand may be modified internucleoside bonds.

Nucleosides in the second nucleic acid strand may be natural nucleosides (comprising deoxyribonucleoside, ribonucleoside, or both) and/or non-natural nucleosides.

The complementary region in the second nucleic acid strand may comprise natural nucleosides (comprising deoxyribonucleoside, ribonucleoside, or both) and/or non-natural nucleosides.

In an embodiment, the complementary region in the second nucleic acid strand may comprise at least two, at least three, at least four, or at least five contiguous ribonucleosides. Such contiguous ribonucleosides can form a double strand with a DNA gap region of a gapmer type oligonucleotide region in the first nucleic acid strand. The double strand can be recognized by RNase H so as to facilitate cleavage of the second nucleic acid strand by RNase H. The contiguous ribonucleosides may be linked with a phosphodiester bond. The nucleosides in the complementary region in the second nucleic acid strand may consist of ribonucleosides.

In another embodiment, the complementary region in the second nucleic acid strand need not comprise at least two contiguous ribonucleosides. The nucleosides in the complementary region in the second nucleic acid strand may consist of ribonucleosides.

The complementary region in the second nucleic acid strand may comprise at least one, at least two, or at least three modified nucleosides from the 5' end. The complementary region in the second nucleic acid strand may comprise at least one, at least two, or at least three modified nucleosides from the 3' end. The complementary region in the second nucleic acid strand may also comprise at least one, at least two, or at least three modified nucleosides from the 5' end, and comprise at least one, at least two, or at least three modified nucleosides from the 3' end. The modified nucleosides may comprise a modified sugar and/or a modified nucleobase. The modified sugar may be a bicyclic sugar, or a 2'-modified sugar (e.g., a sugar comprising a 2'-O-methyl group). The modified nucleobase may be 5-methylcytosine.

The first nucleic acid strand and the second nucleic acid strand may comprise any combination of the aforedescribed modified internucleoside bonds and modified nucleosides.

Figure 3:
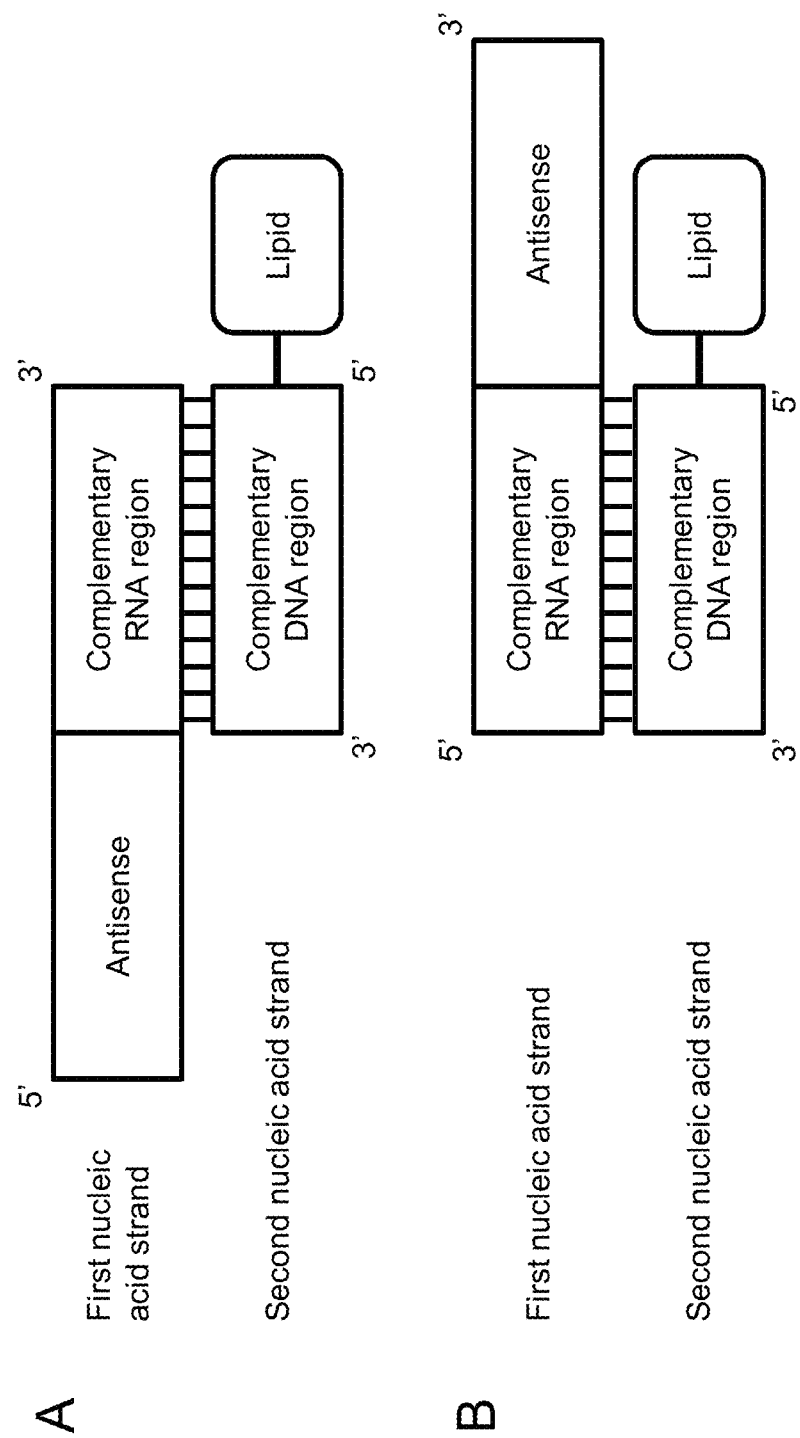

In another specific embodiment, the first nucleic acid strand further comprises a complementary RNA region, while this complementary RNA region has at least two contiguous RNA nucleotides that can be recognized by RNase H, when the first nucleic acid strand is hybridized to the second nucleic acid strand; the complementary region in the second nucleic acid strand is a complementary DNA region, and this complementary DNA region can hybridize to the complementary RNA region of the first nucleic acid strand to facilitate the recognition of at least two contiguous RNA nucleotides in the first nucleic acid strand by RNase H, and further the antisense oligonucleotide region in the first nucleic acid strand cannot hybridize with the second nucleic acid strand. As an example of this embodiment, there is a hetero-chimera-duplex oligonucleotide (HCDO) disclosed in International Publication No. WO 2014/192310. The antisense oligonucleotide region in the first nucleic acid strand may be located on the 5' end side of the complementary RNA region (FIG. 3A), or may be located on the 3' end side of the complementary RNA region (FIG. 3B). When a nucleic acid complex of this embodiment is introduced into a cell, the complementary RNA region is cleaved by RNase H to release the antisense oligonucleotide, and then the antisense oligonucleotide can function, for example, to modify the activity or the function of a transcriptional product (see International Publication No. WO 2014/192310).

The complementary DNA region is complementary to part or all of the complementary RNA region, and in some cases, it may be complementary to part of the antisense oligonucleotide region. However, it is not required that the complementary RNA region is completely complementary to the complementary DNA region, or it has the same number of bases as the complementary DNA region.

The complementary RNA region may include 2, 3, 4, or 5, or even more, for example 5 to 20, 5 to 16, or 5 to 12 contiguous RNA nucleotides (natural RNA), which may optionally be flanked on one or both sides by modified RNA nucleotides.

The complementary DNA region may have a nucleoside configuration of gapmer type as described herein elsewhere.

Although there is no particular restriction on the length of the complementary RNA region or the complementary DNA region, it is usually at least 8 bases, at least 10 bases, at least 12 bases, or at least 13 bases. The length of the complementary RNA region or the complementary DNA region may be 20 bases or less, 25 bases or less, or 35 bases or less.

The second nucleic acid strand is bound (conjugated) to a lipid. Examples of the lipid include, but not limited to, tocopherol, cholesterol, fatty acid, phospholipid and analogs thereof; folic acid, vitamin C, vitamin B1, vitamin B2; estradiol, androstane, and analogs thereof; steroid and analogs thereof; ligands for LDLR, SRBI or LRP1/2; FK-506, and cyclosporine. It has been previously known that the deliverability to e.g., liver may be enhanced by binding a lipid such as tocopherol or cholesterol to a nucleic acid strand. The present invention is based on the findings by the present inventors that a double-stranded nucleic acid complex (a lipid-conjugated heteroduplex oligonucleotide) formed by annealing a complementary strand, to which a lipid (tocopherol) is conjugated, to an antisense oligonucleotide is unexpectedly delivered to an ischemic site of a subject at a high efficiency, so that expression of a target transcriptional product can be modulated at the ischemic site (see Examples 1 to 9 below). It has been suggested (Examples 10 to 13 described below) that this is because a lipid-conjugated heteroduplex oligonucleotide is delivered to vascular endothelial cells in an ischemic site and internal cells beyond the blood vessels (such as neuronal cells in the brain parenchyma, cardiac muscle cells, and skeletal muscle cells) through transcellular pathways via lipid receptors having increased after ischemia.

An "analog" herein refers to a compound having the same or an analogous basic backbone and an analogous structure and nature. An analog includes, for example, a biosynthesis intermediate, a metabolite, and a compound having a substituent. A skilled in the art can determine whether a compound is an analog of another compound.

A tocopherol can be selected from the group consisting of α-tocopherol, β-tocopherol, γ-tocopherol, and δ-tocopherol. Examples of an analog of a tocopherol include various unsaturated analogs of tocopherols, such as α-tocotrienol, β-tocotrienol, γ-tocotrienol, and δ-tocotrienol. Tocopherol is preferably α-tocopherol.

A cholesterol analog refers to various cholesterol metabolites, which are alcohols having a sterol backbone, and analogs thereof. Examples thereof include, but not limited to, cholestanol, lanosterol, cerebrosterol, dehydrocholesterol, and coprostanol.

A lipid may be linked to the 5' end or the 3' end, or to both the ends of the second nucleic acid strand. Alternatively, a lipid may be linked to a nucleotide inside the second nucleic acid strand. The second nucleic acid strand may comprise two or more lipids, which may be linked to a plurality of positions in the second nucleic acid strand and/or may be linked as a group to one position in the second nucleic acid strand. Lipids may be linked one each to the 5' end and the 3' end of the second nucleic acid strand.

The bond between the second nucleic acid strand and a lipid may be a direct bond or an indirect bond mediated by another substance. However, in a specific embodiment, it is preferable that the lipid is directly conjugated to the second nucleic acid strand via a covalent bond, an ionic bond, a hydrogen bond, or the like, and in view of the fact that a more stable bond can be obtained, a covalent bond is more preferable.

The lipid may also be conjugated to the second nucleic acid strand via a cleavable linking group (linker). A "cleavable linking group (linker)" means a linking group that is cleaved under physiological conditions, for example, inside a cell, or inside an animal body (e.g., inside a human body). In a certain embodiment, a cleavable linker is selectively cleaved by an endogenous enzyme, such as a nuclease. Examples of a cleavable linker include an amide, an ester, one or both esters of a phosphodiester, a phosphate ester, a carbamate, and a disulfide bond, as well as a natural DNA linker.

The lipid may also be conjugated to the second nucleic acid strand via an uncleavable linker. An "uncleavable linker" means a linking group that is not cleaved under physiological conditions, for example, inside a cell, or inside an animal body (e.g., inside a human body). Examples of an uncleavable linker include a linker consisting of a phosphorothioate bond, and modified or unmodified deoxyribonucleosides, or modified or unmodified ribonucleosides linked by a phosphorothioate bond. When the linker is a nucleic acid or an oligonucleotide, such as DNA, its chain length is not particularly limited, and may be from 2 to 20 bases in length, from 3 to 10 bases in length, or from 4 to 6 bases in length.

The second nucleic acid strand may further comprise at least one functional moiety conjugated to a polynucleotide. There is no particular restriction on the structure of a "functional moiety" in a specific embodiment, insofar as the functional moiety can confer a desired function to the strand to which a nucleic acid complex and/or the functional moiety is conjugated. Examples of a desired function include a labeling function and a purifying function. Examples of a moiety to confer a labeling function include a compound such as a fluorescent protein, and luciferase. Examples of a moiety to confer a purifying function include a compound such as biotin, avidin, His-tag peptide, GST-tag peptide, and FLAG-tag peptide. The binding position and the type of bond of the functional moiety in the second nucleic acid strand are as described above in connection with the bond between a lipid and the second nucleic acid strand.

One skilled in the art can produce the first nucleic acid strand and the second nucleic acid strand constituting a nucleic acid complex by appropriately selecting known methods. For example, a nucleic acid can be produced by designing the base sequence of each nucleic acid based on the information about the base sequence of a target transcriptional product (or, in some examples, the base sequence of a target gene), synthesizing the nucleic acid using a commercial automatic nucleic acid synthesizer (such as product of Applied Biosystems, Inc., or product of Beckman Coulter, Inc.), and then purifying the obtained oligonucleotides using a reversed phase column or the like. The nucleic acid produced by this method is mixed in an appropriate buffer solution and denatured at about 90° C. to 98° C. for several minutes (e.g., 5 min), and then the nucleic acid is annealed at about 30° C. to 70° C. for about 1 to 8 hours, so that a nucleic acid complex can be produced. Production of an annealed nucleic acid complex is not limited to such time and temperature protocols. Conditions suitable for promoting annealing of strands are well known in the art. A nucleic acid complex to which a lipid or a functional moiety is conjugated can be produced by using a nucleic acid species to which a lipid or a functional moiety has been conjugated in advance, and performing the synthesis, purification, and annealing as described above, or by linking a lipid or a functional moiety to a nucleic acid afterwards. A large number of methods for linking a lipid or a functional moiety to a nucleic acid are well known in the art. Alternatively, a nucleic acid strand is available on demand from a manufacturer (e.g., GeneDesign Inc.) by specifying a base sequence and a modification site or type.

(Composition)

A composition comprising the above nucleic acid complex for modulating expression of a target transcriptional product in an ischemic site of a subject having ischemia is provided. This composition may be a pharmaceutical composition.

Also provided is a composition comprising the above nucleic acid complex for delivering the nucleic acid complex to an ischemic site of a subject having ischemia.

Ischemia is a condition where the blood is not supplied. There is no limitations of causes for ischemia, and there are, for example, compressive ischemia caused by constriction or blockage of the arterial wall due to an external pressure, occlusive ischemia due to changes inside the blood vessel or of the vessel itself, etc.

An ischemic site may be located in any organ or tissue of the body. For example, it may be located in the brain, spinal cord, cardiac muscles, skeletal muscles (including upper limb skeletal muscle, and lower limb skeletal muscle), blood vessels, lung, kidney, liver, enteric canal, spleen, eye, retina, skin, peripheral nerve, or extremities.

Although there is no particular restriction on a cell in an ischemic site in which expression of a target transcriptional product is modulated by the present composition, or to which the nucleic acid complex is delivered, examples thereof may include, but not limited to, a vascular endothelial cell (artery, arteriola, capillary, venula, and vein), a vascular smooth muscle, a cardiac muscle cell (including special cardiac muscle), a skeletal muscle cell, a central nerve cell (neuronal cell, astroglia, microglia, and oligodendrocyte), buffy coat, a peripheral nerve cell (neuronal cell, and Schwann cell), a liver cell, and a kidney cell.

The present composition may be for treating an ischemic disease. The ischemic disease may be either acute or chronic ischemic disease. An ischemic disease encompasses any disease associated with ischemic pathology.

Examples of an acute ischemic disease include, but not limited to, cerebrovascular disorder (ischemic stroke, spinal cord infarction, cerebral venous sinus thrombosis, cerebral vasoconstriction syndrome, cerebral vasculitis, cerebral hemorrhage, subarachnoid hemorrhage, moyamoya disease, cerebral arteriovenous fistula, cerebral arteriovenous malformation, cerebral aneurysm, cervical/cerebral artery dissection, head trauma, brain contusion, and brain tumor); myocardial infarction, angina, and postmyocardial infarction arrhythmia; arteriosclerosis obliterans (ASO), e.g., lower limb arteriosclerosis obliterans; other acute ischemic diseases, e.g., coagulation disorder (disseminated intravascular coagulation syndrome, hypercoagulability associated with malignant tumor, protein C deficiency, protein S deficiency, etc.), congenital connective tissue disease (Ehlers-Danlos syndrome, fibromuscular dysplasia), aortic dissection, pulmonary infarction, renal infarction, hepatic infarction, and acute mesenteric artery occlusion, splenic infarction, acute (femoral) arterial occlusion, retina arterial occlusion, radiation vasculopathy, age-related vasculopathy, and drug-induced vasculopathy.

Examples of a chronic ischemic disease include, but not limited to, cerebrovascular dementia (hereditary cerebrovascular disorder (e.g., CADASIL, CARASIL), Fabry disease, and Binswanger's disease), cerebrovascular parkinsonian syndrome, cerebral amyloid angiopathy, traumatic disease, Buerger's disease, ischemic enteritis, diabetic peripheral neuropathy, and ischemic optic nerve disorder.

Examples of other diseases with ischemic pathology include, but not limited to, inflammatory disease, hereditary/congenital disease, trauma, neoplastic disease, infectious disease, metabolic disease, toxic disease, meningitis, encephalitis, brain abscess, septicemia, infectious endocarditis, Takayasu's disease, vasculitis syndrome (ANCA-associated disease, and secondary vasculitis associated with collagen disease), myositis (polymyositis, dermatomyositis, inclusion body myopathy, and necrotizing myopathy), inflammatory bowel disease, livedo vasculopathy, malignant tumor such as malignant lymphoma, paraneoplastic syndrome, hereditary vasculopathy, mitochondrial encephalomyopathy, and spinal disorders with ischemic pathology (cervical spondylosis, lumbar spondylosis, spinal arteriovenous fistula, and spinal arteriovenous malformation).

The ischemic disease is preferably ischemic stroke, myocardial infarction, or arteriosclerosis obliterans.

A subject may be any animal, including human. However, there is no specific limitation on animal other than human, and various livestock, poultry, pets, and laboratory animals can be a subject. The subject may be a subject in need of modulation of expression of a target transcriptional product in an ischemic site. The subject may also be a subject in need of a treatment for an ischemic disease. The subject may be a subject in the ischemia acute phase.

The present composition may be formulated by a known pharmaceutical production method. For example, the present composition can be used perorally or parenterally in a form of capsule, tablet, pill, liquid formulation, dispersant, granule, microgranule, film coating agent, pellet, troche, sublingual formulation, peptizer, buccal tablet, paste, syrup, suspending agent, elixir, emulsion formulation, coating agent, ointment, plaster, cataplasm, transdermal patch, lotion, inhalant, aerosol, eye drop, injection, or suppository.

The present composition may appropriately incorporate a pharmaceutically acceptable carrier, specifically a surfactant, a pH regulator, a stabilizer, an excipient, a vehicle, a preservative, a diluent, an isotonizing agent, a sedative, a buffer, and other additives, as well as a pharmaceutically acceptable solvent, specifically sterile water, a physiological saline solution, a buffer solution (including phosphate buffer), and other solvents.

The dose of the present composition may be selected appropriately according to the age, body weight, symptoms, and health status of a subject, the dosage form, etc. The dose of the present composition may be, for example, in terms of nucleic acid complex, from 0.0000001 mg/kg/day to 1,000,000 mg/kg/day, from 0.00001 mg/kg/day to 10,000 mg/kg/day, or from 0.001 mg/kg/day to 500 mg/kg/day.

There is no specific limitation on the administration mode of the present composition, and examples thereof include peroral administration or parenteral administration, more specifically, intravenous administration, intraventricular administration, intrathecal administration, subcutaneous administration, intra-arterial administration (e.g., selective intra-arterial administration with an intravascular catheter), intraperitoneal administration, intradermal administration, tracheal/bronchial administration, rectal administration, intra-ocular administration, and intramuscular administration, as well as administration by transfusion. Administration may be performed by intramuscular injection, continuous instillation, inhalation, skin patch, or implantable continuous subcutaneous administration. In this regard, the subcutaneous administration may be advantageous compared to the intravenous administration in terms of ease of administration, or the like. Since a subcutaneous administration can be carried out by self-injection by a patient on its own, it is preferable.

The present composition can be administered in the ischemia acute phase. The ischemia acute phase may be within 15 hours, within 12 hours, within 9 hours, within 6 hours, within 3 hours, or within 1 hour from the onset of ischemia. A treatment in the ischemia acute phase is important, because as the ischemic condition lasts longer, the damages to organs, tissues, and cells become severer. However, in the case of a cerebrovascular disorder such as ischemic stroke, drug delivery to the brain is difficult due to the function of the blood-brain barrier (BBB), which restricts the supply of substances into the brain, in the ischemia acute phase within approximately 15 hours from the onset of ischemia. The present invention advantageously makes it possible to deliver a drug (antisense oligonucleotide) to the brain, even in the ischemia acute phase before the blood-brain barrier is disrupted.

According to the present composition is used, a nucleic acid complex can be delivered specifically to an ischemic lesion site so as to modulate expression of a target transcriptional product. Consequently, it is possible to control a gene with a lower dosage, and to avoid side effects because drug delivery to other than the target organ can be lowered.

In one aspect, provided is a method of treating an ischemic disease comprising administering the above nucleic acid complex or composition to a subject having ischemia.

In another aspect, provided is a method of modulating expression of a target transcriptional product (for example, reducing the expression amount of a transcriptional product) in an ischemic site of a subject, comprising administering the above nucleic acid complex or composition to a subject having ischemia.

In another aspect, provided is a method of delivering a nucleic acid complex to an ischemic site of a subject, comprising administering the above nucleic acid complex or composition to a subject having ischemia is provided.

EXAMPLES

Hereinafter, the present invention is described more specifically with reference to Examples. However, the scope of the present invention is not limited to these Examples.

Example 1

(Delivery of Lipid-Ligand-Conjugated Double-Stranded Oligonucleotide to Ischemic Stroke Site)

The delivery of lipid-ligand-conjugated heteroduplex oligonucleotide (HDO; also referred to as heteronucleic acid; see International Publication No. WO 2013/089283, Nishina K, et. al. Nature Communication, 2015, 6:7969, and Asami Y, et al., Drug Discoveries & Therapeutics. 2016; 10(5): 256-262) to an ischemic stroke site (ischemic lesion) was compared with that of a conventional antisense oligonucleotide (ASO).

(Method)

An LNA/DNA gapmer ASO (Alexa-ASO) with AlexaFluor568, a fluorescent dye, covalently linked at the 5' end was prepared (FIG. 6A). This ASO has a base sequence complementary to position 1317 to 1332 of Malat-1 non-coding RNA (SEQ ID NO: 1) and targets the Malat-1 gene. This ASO is an oligonucleotide of 16 bases in length comprising three LNA nucleosides from the 5' end, three LNA nucleosides from the 3' end, and 10 DNA nucleosides therebetween.

A complementary RNA strand having a base sequence complementary to this ASO and having a tocopherol covalently linked at the 5' end (Toc-cRNA) was prepared. Toc-cRNA is an oligonucleotide of 16 bases in length comprising three 2'-O-methyl RNA nucleosides from the 5' end, three 2'-O-methyl RNA nucleosides from the 3' end, and 10 RNA nucleosides therebetween.

By annealing Alexa-ASO to Toc-cRNA, an Alexa-labeled lipid-ligand (tocopherol)-conjugated heteroduplex oligonucleotide (Alexa-Toc-HDO) was prepared as follows (FIG. 6B). Alexa-ASO and Toc-cRNA (powder) were placed in phosphate-buffered saline (PBS), and dissolved through vortexing, and the resulting solutions were mixed in equal molar volumes, the mixture was heated at 95° C. for 5 minutes, then cooled to 37° C. and held for 1 hour, whereby Alexa-ASO was annealed to Toc-cRNA. The annealed nucleic acids were stored at 4° C. or on ice.

Figure 6:
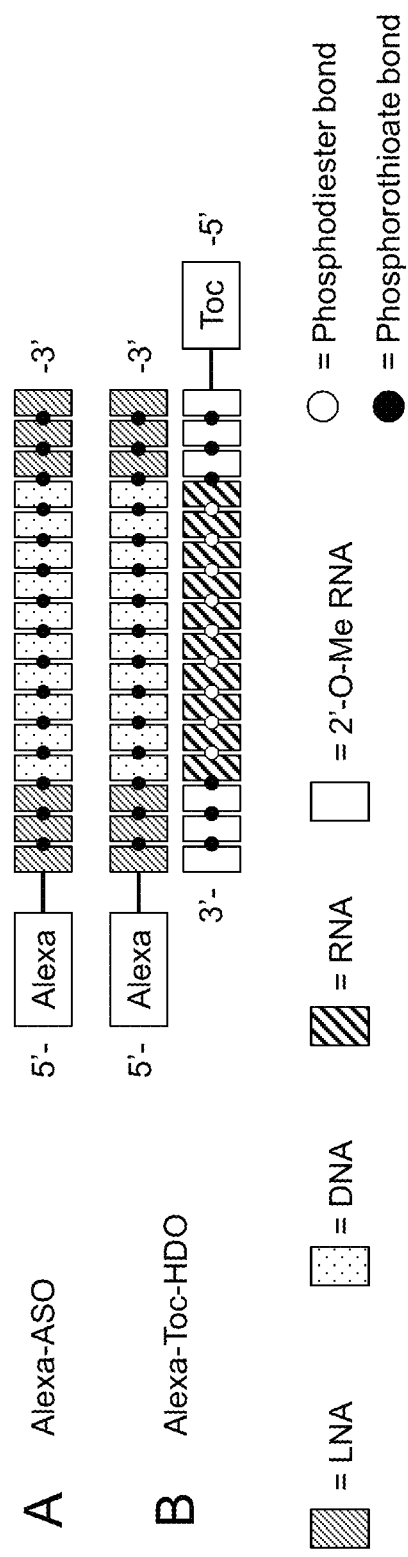
FIG. 6 is a schematic diagram of the structures of the nucleic acids used in Example 1. Alexa represents AlexaFluor568. Toc represents tocopherol.

The sequences, chemical modifications, and structures of the oligonucleotides used in Example 1 are shown in Table 1 and FIG. 6. All oligonucleotides were produced by Gene Design, Inc. (Osaka, Japan).

TABLE 1

| Oligo-<br>nucleotide<br>name | Sequence (5'-3') | SEQ<br>ID<br>NO: |
| --- | --- | --- |
| Alexa-ASO | Alexa-5(L)*T(L)*A(L)*g*t*t*<br>c*a*c*t*g*a*a*T(L)*G(L)*5(L) | 3 |

TABLE 1-continued

| Oligo-nucleotide name | Sequence (5'-3') | SEQ ID NO: |
|---|---|---|
| Toc-cRNA | Toc-G(M)*C(M)*A(M)*UUCAGUGA AC*U(M)*A(M)*G(M) | 4 |

Uppercase letter (L): LNA (5 (L) represents 5-methylcytosine LNA),
Lowercase letter: DNA,
Uppercase letter: RNA,
Uppercase letter (M): 2'-O-Me RNA,
*Phosphorothioate bond,
Alexa: AlexaFlour568,
Toc: tocopherol Using 8 to 12 week-old mice (C57BL6, male, Sankyo Lab Services Co., Ltd.), a model of ischemic stroke was prepared as follows. A mouse was anesthetized by inhalation of 2.5% isoflurane, and body temperature was maintained at 36.5±0.5° C. with a heat pad during the surgery. The skin of the left head of the mouse was incised and a 2-mm hole was drilled with a microdrill into the skull just above the middle cerebral artery to expose the middle cerebral artery. The exposed middle cerebral artery was occluded by electronic incineration to prepare an ischemic stroke mouse model.

After 3 hours of arterial occlusion, the ischemic stroke model mouse was injected intravenously through a tail vein with Alexa-ASO or Alexa-Toc-HDO at a dose of 50 mg/kg. As a negative control group, only PBS was administered to an ischemic stroke mouse model.

Three hours after injection (6 hours after arterial occlusion), the mouse was euthanized, perfused with PBS, and then dissected, and organs (cerebrum and liver) were isolated. The isolated organs were fixed with 4% paraformaldehyde (PFA), and thin sections of 20 μm were prepared. The sections were treated with DAPI (4',6-diamidino-2-phenylindole) and the nuclei were stained. The sections were observed for Alexa signals and nuclei by fluorescence microscopy.

Another ischemic stroke mouse model was prepared using a similar protocol, and three hours after tail vein administration of Alexa-ASO or Alexa-Toc-HDO, the mouse was euthanized, perfused with PBS, and organs (cerebral hemisphere and liver) were isolated. The cerebral hemisphere was divided into an ischemic stroke cerebral hemisphere and a non-ischemic cerebral hemisphere. The organs were placed in PBS and homogenized. The fluorescence intensity of Alexa in the obtained samples was measured with a microplate reader (Infinite® M1000 PRO, TECAN group Ltd., Mannedorf, Switzerland). The amount of oligonucleotides (pmol) per 1 g of an organ was calculated based on the measurement results.

(Results)

Figure 7:
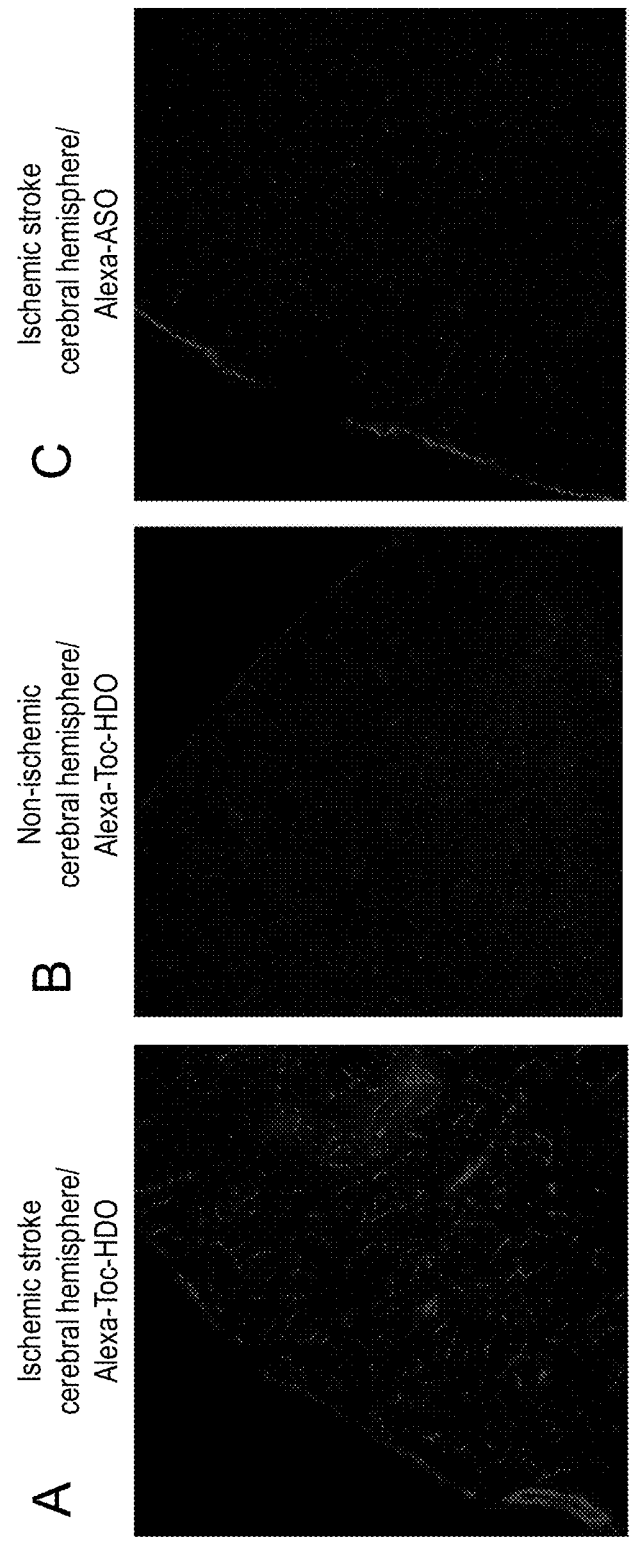
FIG. 7 shows fluorescence microscope images showing the results of Example 1, in which delivery of a lipid-ligand-conjugated double-stranded oligonucleotide to an ischemic stroke site was examined.
Figure 8:
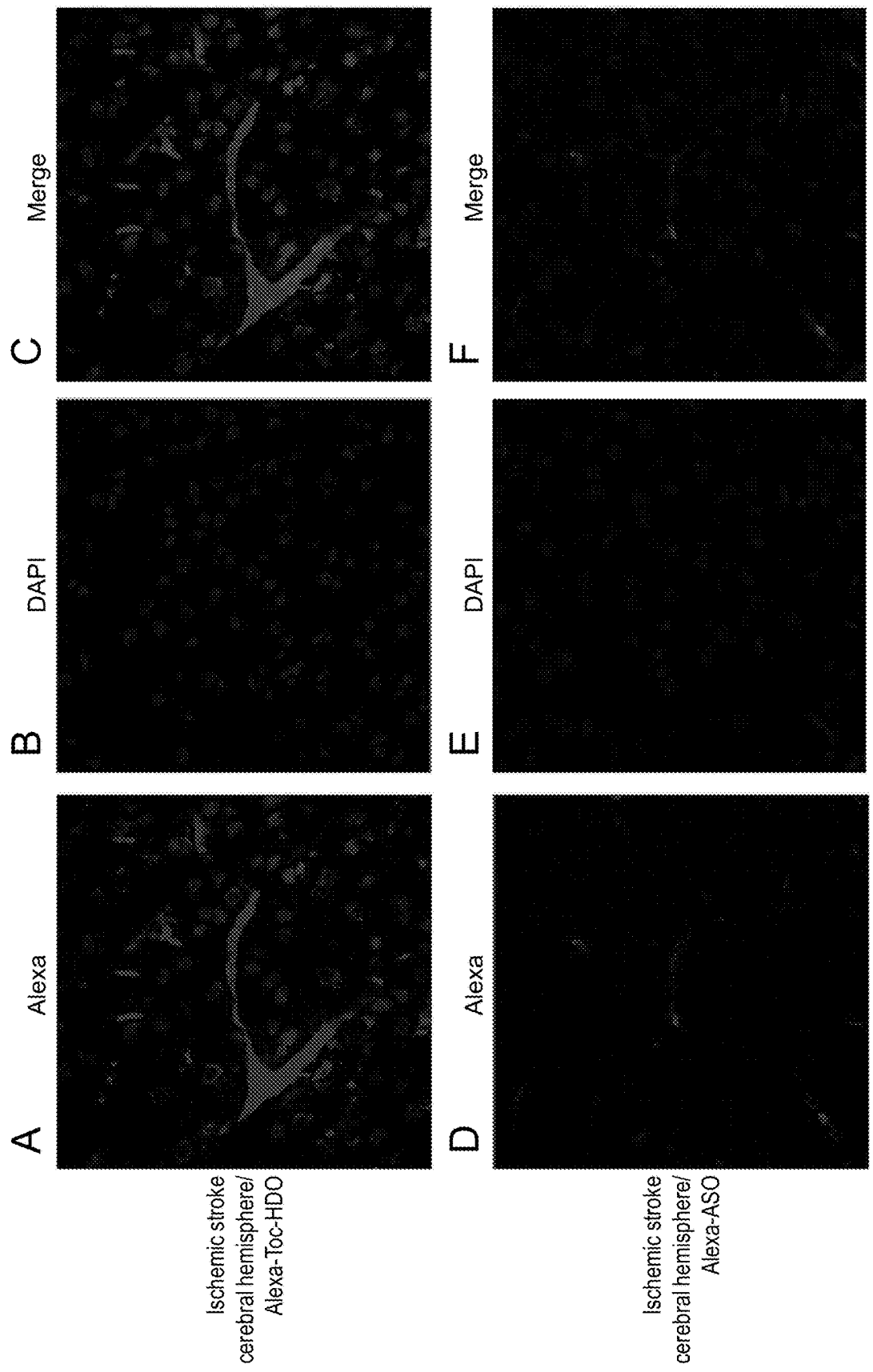
FIG. 8 shows fluorescence microscope images showing the results of Example 1, in which delivery of a lipid-ligand-conjugated double-stranded oligonucleotide to an ischemic stroke site was examined.

In an Alexa-Toc-HDO administration group, a very strong Alexa signal was found in an ischemic stroke site (FIGS. 7A and 8A to 8C), whereas in a non-ischemic site, only a weak Alexa signal was found mainly in cerebral vascular endothelial cells (FIG. 7B). Further, in an Alexa-ASO administration group, even in the ischemic stroke cerebral hemisphere, there was only a weak Alexa signal in some cerebral vascular endothelial cells (FIGS. 7C and 8D to 8F). In a negative control group in which PBS was administered, no obvious Alexa signal was detected on brain sections in both the ischemic stroke cerebral hemisphere and non-ischemic cerebral hemisphere.

At ischemic stroke sites in an Alexa-Toc-HDO administration group, an Alexa signal was found morphologically in arteries, arterioles, capillaries, a pia mater, and neuronal cells and some glial cells belonging to the central nervous system (FIG. 7A).

Figure 9:
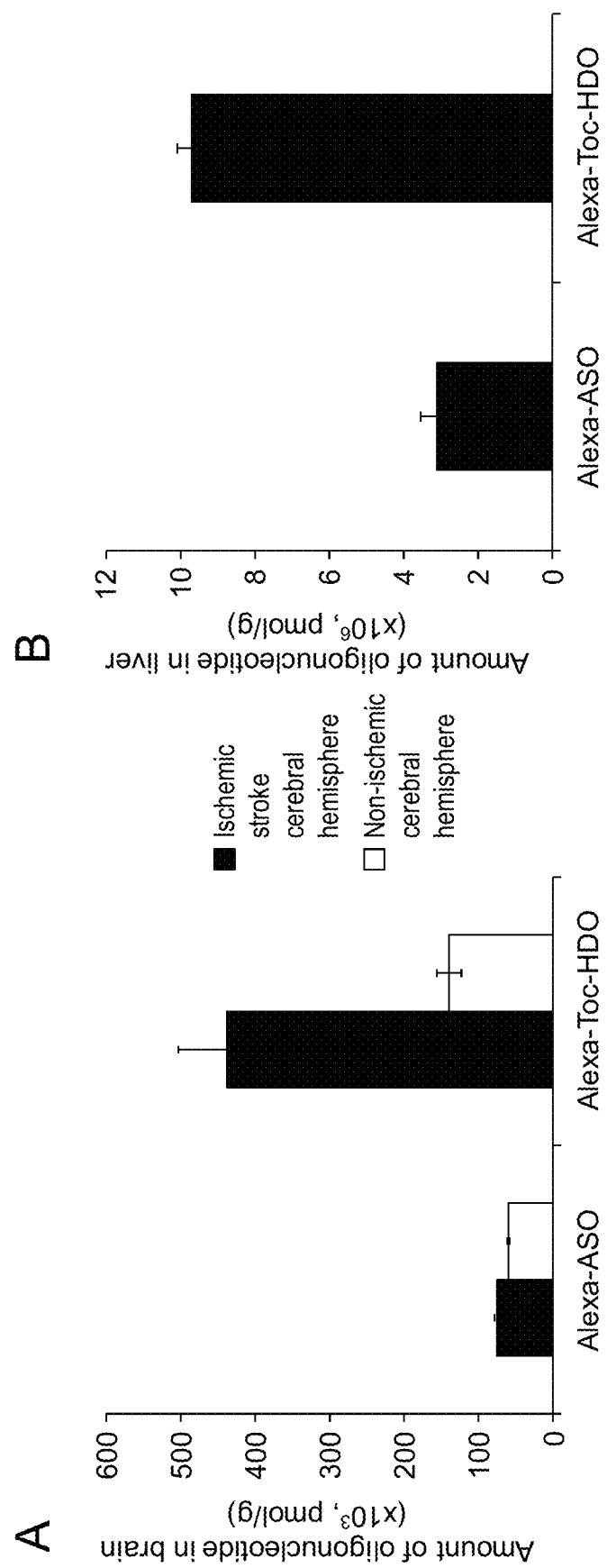
FIG. 9 shows graphs showing the results of Example 1, which show the amounts of oligonucleotides in the organs isolated from ischemic stroke mouse model administered with Alexa-ASO or Alexa-Toc-HDO.

Further, as shown by the amount of oligonucleotides in a brain in FIG. 9A, the amount of Alexa-Toc-HDO in an ischemic stroke cerebral hemisphere was larger than that of Alexa-ASO, and also larger than that of Alexa-Toc-HDO in a non-ischemic cerebral hemisphere. As shown by the amount of oligonucleotides in a liver in FIG. 9B, Alexa-Toc-HDO in a liver is more abundant than Alexa-ASO, and this result was consistent with a previous report (International Publication No. WO 2013/089283).

These results showed that lipid-ligand-conjugated heteroduplex oligonucleotides are delivered to an ischemic stroke site far more efficiently than single-stranded antisense oligonucleotides, and are delivered to a variety of cell types, including arteries, arterioles, capillaries, a pia mater, and neuronal cells and some glia cells belonging to the central nervous system, in the ischemic stroke site.

Example 2

(Further Analysis of Delivery of Lipid-Ligand-Conjugated Duplex Oligonucleotide to Ischemic Stroke Site)

An ischemic stroke site to which a lipid-ligand-conjugated heteroduplex oligonucleotide was delivered was observed in more detail using a vascular endothelial marker and a neuronal cell marker.

(Method)

An ischemic stroke mouse model was prepared as described in Example 1, a lipid-ligand (tocopherol)-conjugated heteroduplex oligonucleotide (Alexa-Toc-HDO) was administered to the ischemic stroke mouse model, the brain was isolated, and thin sections were prepared. The sections were immunostained using an anti-CD31 antibody (a rat anti-mouse CD31 antibody (1:50 dilution, BD Pharmingen™, BD Biosciences) or a rat anti-mouse CD31 antibody (1:50 dilution, Santa Cruz Biotechnology)) as a vascular endothelial cell marker and an anti-NeuN antibody (mouse anti-NeuN antibody (1:100 dilution, EMD Millipore)) as a neuronal cell marker. Fluorescently labeled secondary antibodies (FITC or rhodamine-labeled goat antibodies) corresponding to respective primary antibodies were obtained from EMD Millipore Corporation. Further, the sections were treated with DAPI and the nuclei were stained. The sections were observed for Alexa signals, CD31 or NeuN signals, and nuclei by fluorescence microscopy.

(Results)

Figure 10:
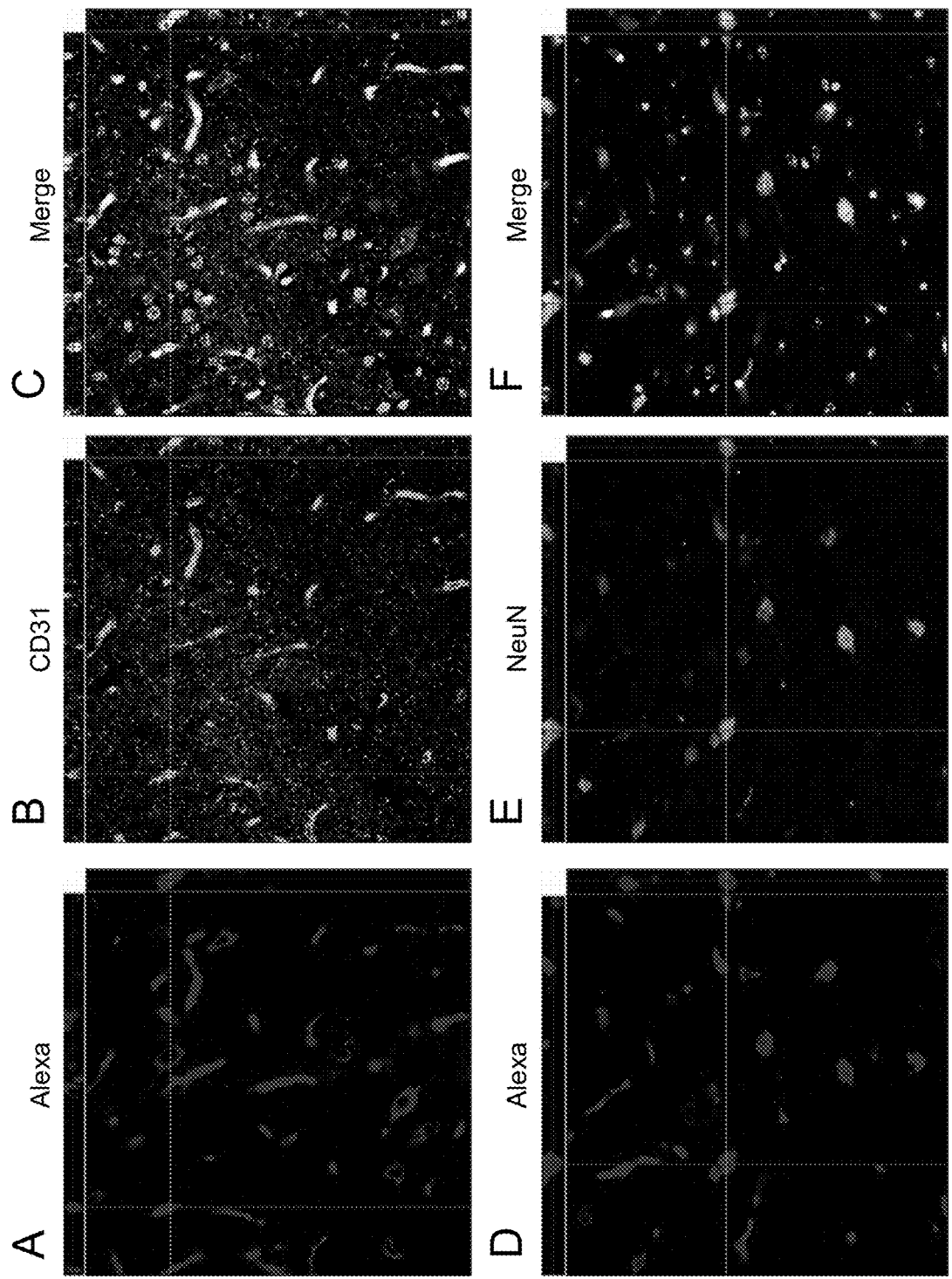
FIG. 10 shows fluorescence microscope images showing the results of Example 2, in which delivery of a lipid-ligand-conjugated double-stranded oligonucleotide to an ischemic stroke site was further analyzed.

In an ischemic stroke site in an ischemic stroke mouse model to which Alexa-Toc-HDO was administered, an Alexa signal was observed in CD31-positive cerebral vascular endothelial cells (FIGS. 10A to 10C) and also in neuronal cells (NeuN-positive cells) which are central neurons (FIGS. 10D to 10F).

The results of Examples 1 and 2 showed that, even in an ischemic stroke hyperacute phase three hours after arterial occlusion without disruption of the intercellular space of the blood-brain barrier, a lipid-ligand-conjugated heteroduplex oligonucleotide was delivered to a cerebral blood vessel selectively at an ischemic stroke site, and further delivered to neuronal cells and glial cells (in the brain parenchyma) beyond the blood-brain barrier, and that the delivery efficiency thereof was much superior to that of a single chain antisense oligonucleotide.

Example 3

(Inhibition of Target Gene Expression in Ischemic Stroke Model Mice)

An effect of inhibiting target gene expression by a lipid-ligand-conjugated heteroduplex oligonucleotide in an ischemic stroke mouse model was examined in comparison with an antisense oligonucleotide (ASO).

(Method)

The same LNA/DNA gapmer ASO as used in Example 1 except that AlexaFluor568 which is a fluorescent dye was not conjugated was prepared. This ASO was annealed to the Toc-cRNA (a complementary RNA strand covalently bound to tocopherol) used in Example 1 to prepare a lipid-ligand (tocopherol)-conjugated heteroduplex oligonucleotide (Toc-HDO).

The same protocol as in Example 1 was used to prepare an ischemic stroke mouse model and 3 hours after arterial occlusion, ASO or Toc-HDO at a dose of 50 mg/kg was injected intravenously through a tail vein. As a negative control group, PBS only or shuffled Toc-HDO was administered to an ischemic stroke mouse model.

The shuffled Toc-HDO is a double-stranded oligonucleotide having the same base composition and chemical modifications as Toc-HDO, and having a different base sequence. The sequences and chemical modifications of the two oligonucleotides constituting the shuffled Toc-HDO are shown in Table 2.

TABLE 2

| Sequence (5'-3') | SEQ ID NO: |
|---|---|
| T(L)*A(L)*5(L)*a*t*a*t*g*c*g*c*t*a*5(L)*T(L)*G(L) | 5 |
| Toc-C(M)*A(M)*G(M)*UAGCGCAUAU*G(M)*U(M)*A(M) | 6 |

Uppercase letter (L): LNA (5 (L) represents 5-methylcytosine LNA),
Lowercase letter: DNA,
Uppercase letter: RNA,
Uppercase letter (M): 2'-O-Me RNA,
*Phosphorothioate bond,
Toc: tocopherol Seventy two hours after injection (75 hours after arterial occlusion), the mouse was euthanized, perfused with PBS, and then dissected, and organs (cerebrum and liver) were isolated. The cerebrum was divided into ischemic stroke cerebral hemisphere and non-ischemic cerebral hemisphere. RNA was extracted from isolated organs using Isogen (Nippon Gene, Tokyo, Japan), cDNA was synthesized using Transcriptor Universal cDNA Master (Roche Diagnostics), and quantitative RT-PCR was performed by Light Cycler 480 Real-Time PCR Instrument (Roche Diagnostics) using Malat-1 primer (NR_002847, Applied Biosystems (TaqMan Gene Expression Assays)) to assess the expression level of mouse Malat-1 non-coding RNA. A Gapdh (glyceraldehyde-3-phosphate dehydrogenase) primer (Thermo Fisher Scientific Inc., product number 4352932E) was used as an internal standard gene for quantitative RT-PCR. A relative Malat1-level was obtained by normalizing the Malat-1 expression level to the Gapdh mRNA expression level.

Another ischemic stroke mouse model that was administered similarly was prepared, and the mouse was euthanized 72 hours after injection (75 hours after arterial occlusion), perfused with PBS, and the cerebrum was isolated. The cerebrum was fixed with 4% PFA and 12 µm thin sections were prepared. The Malat-1 gene on frozen sections was identified by in situ hybridization using the QuantiGene ViewRNA tissue assay (Affymetrix Inc., catalog number QVT0011) and Malat-1 probe (Affymetrix Inc., catalog number VB-11110-01/mouse).

(Results)

Figure 11:
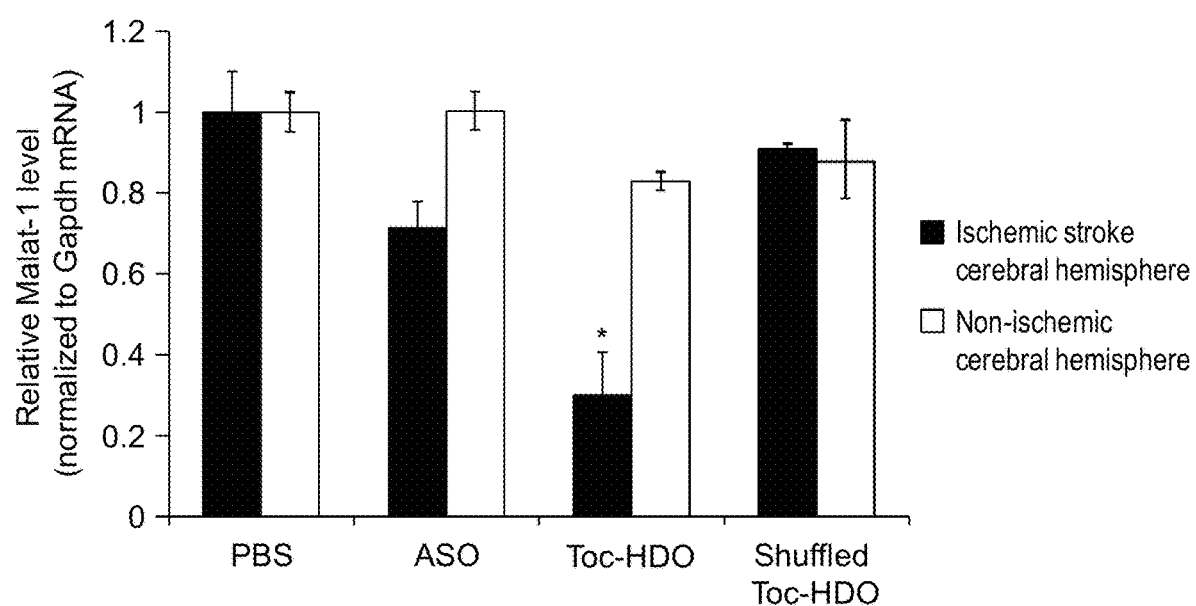
FIG. 11 is a graph showing the results of Example 3, in which an inhibition of target gene expression by a lipid-ligand-conjugated double-stranded oligonucleotide in an ischemic stroke mouse model was examined by quantitative RT-PCR method.

As shown in white bars in FIG. 11 (relative Malat-1 levels), in a non-ischemic cerebral hemisphere, there was no significant decrease in Malat-1 gene expression in both the ASO administration group and the Toc-HDO administration group compared with the PBS administration group (each group was examined for five animals). On the other hand, as shown by the black bars in FIG. 11 (relative Malat-1 levels), Malat-1 gene expression was significantly decreased in ischemic stroke cerebral hemispheres only in the Toc-HDO administration group compared with the PBS administration group (*p<0.01).

Figure 12:
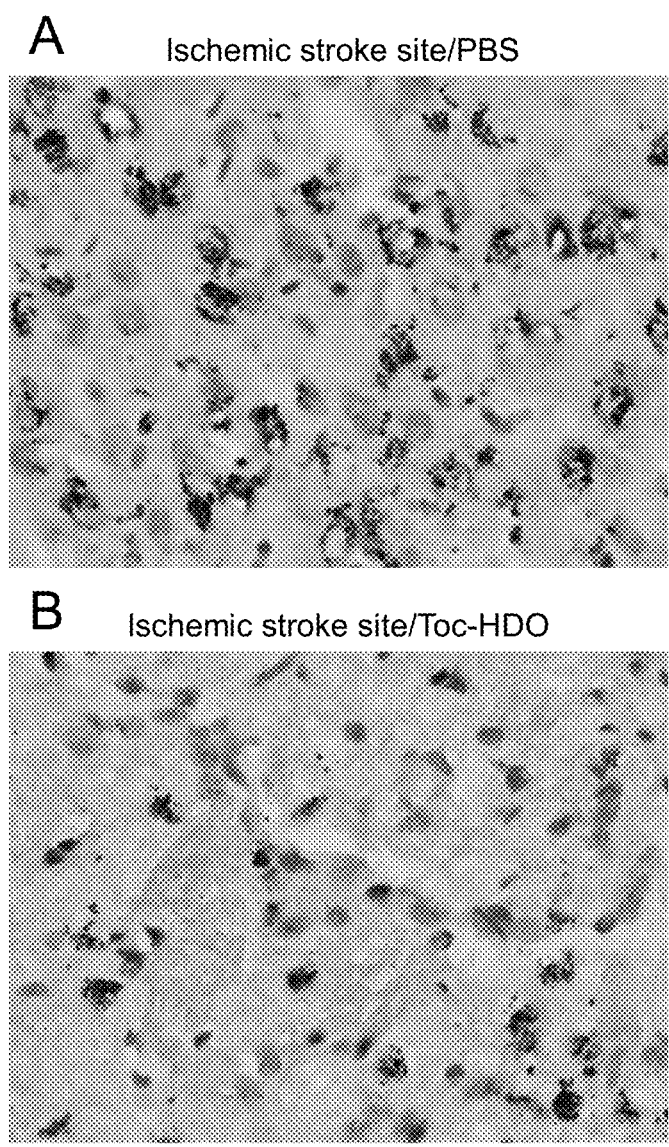
FIG. 12 shows photographs showing the results of Example 3, in which an inhibition of target gene expression by a lipid-ligand-conjugated double-stranded oligonucleotide in ischemic stroke model mice was examined by in situ hybridization method.

In Malat-1 in situ hybridization of ischemic stroke lesion sites shown in FIGS. 12A and 12B, Malat-1 gene signal was mainly found in cerebral vascular endothelial cells and neuronal cells. Compared with PBS administration group (FIG. 12A) and ASO administration group, Malat-1 gene signal was significantly reduced in cerebral vascular endothelial cells and neuronal cells in ischemic stroke site in the Toc-HDO administration group (FIG. 12B).

These results indicate that lipid-ligand-conjugated heteroduplex oligonucleotides administered intravenously can achieve a strong gene inhibition effect selectively at ischemic stroke sites.

Example 4

(Change in Pathophysiology of Ischemic Stroke)

Whether a lipid-ligand-conjugated heteroduplex oligonucleotide can change the pathophysiology of ischemic stroke was examined.

(Method)

An ischemic stroke mouse model was prepared in the same manner as in Example 3, and 3 hours after arterial occlusion, Toc-HDO at a dose of 50 mg/kg was injected intravenously through a tail vein. As a negative control group, PBS only or shuffled Toc-HDO was administered to an ischemic stroke mouse model.

Motor function of mice was evaluated over time until 4 days after arterial occlusion. The motor function was evaluated by the right-biased body swing rate (%). Specifically, a mouse was lifted by the tail, the direction of trunk bend was counted for 1 minute, and the ratio of the number of rightward bends to the total number of bends was defined as the right-biased body swing rate (%) (see Borlongan C V, Sanberg P R. Elevated body swing test: a new behavioral parameter for rats with 6-hydroxydopamine-induced hemi-parkinsonism. J Neurosci. 1995; 15: 5372-5378). A mouse having a left ischemic stroke will have a higher number of trunk bends to the opposite side, the right. The higher this rate is, the worse the motor function is on the paralyzed side.

The brain blood flow was also measured in a mouse 4 days after arterial occlusion. The brain blood flow was expressed as a percentage (%) over the baseline (before surgery).

Then, 20 µm thin sections were prepared from the mouse cerebrum using the same method as in Example 3, and the ischemic stroke volume was quantified and compared. The percentage (%) of ischemic stroke volume to the whole brain was calculated.

(Results)

Figure 13:
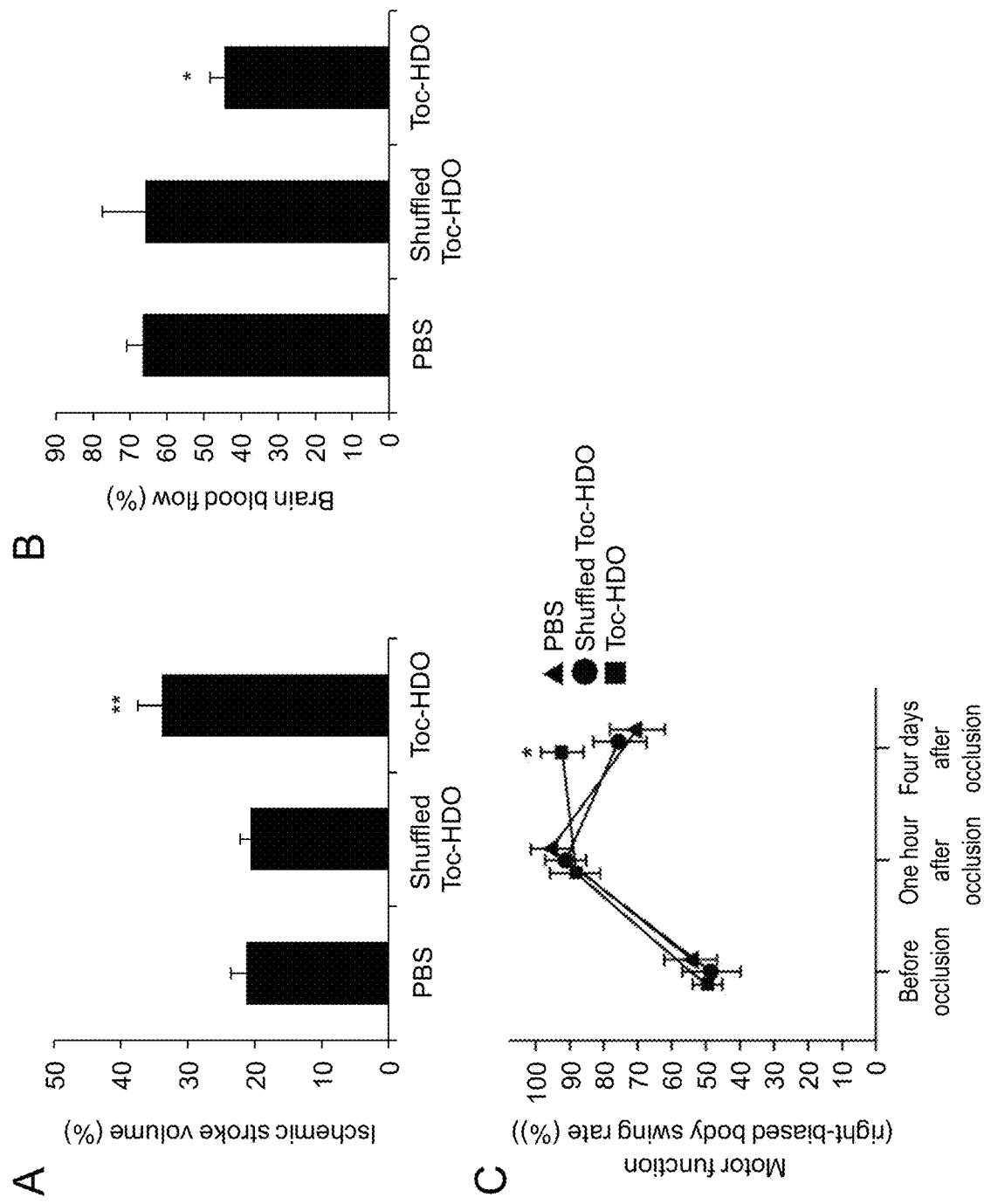
FIG. 13 shows graphs showing the results of Example 4, in which changes in pathophysiology of ischemic stroke by a lipid-ligand-conjugated double-stranded oligonucleotide were examined.

The ischemic stroke volume was significantly increased in the Toc-HDO administration group compared with the PBS administration group and the shuffled Toc-HDO administration group (negative control) (FIG. 13A, **p<0.01).

The brain blood flow was significantly reduced in the Toc-HDO administration group (FIG. 13B, *p<0.05) and motor function was significantly worsened (FIG. 13C, *p<0.05).

These worsenings in the pathophysiology of ischemic stroke were similar to those reported in a previous report (Zhang X, et al., Long Noncoding RNA Malat1 Regulates Cerebrovascular Pathologies in Ischemic Stroke. J Neurosci. 2017; 37(7):1797-1806) of ischemic stroke in Malat-1 gene knockout mice.

The results of Examples 1 to 4 showed that lipid-ligand-conjugated heteroduplex oligonucleotides administered intravenously during the hyperacute phase of ischemic stroke can be delivered into the cerebral blood vessels and brain parenchyma, strongly inhibiting target gene expression and also altering the pathophysiology of ischemic stroke. It was suggested that a lipid-ligand-conjugated heteroduplex oligonucleotide can treat an ischemic disease such as ischemic stroke by targeting such a gene that produces a disease-improving effect when the expression is inhibited, contrary to Malat-1.

Example 5

(Delivery of Lipid-Ligand-Conjugated Duplex Oligonucleotide to Myocardial Infarction Site)

The delivery of a lipid-ligand-conjugated heteroduplex oligonucleotide to a myocardial infarction site was compared with a conventional antisense oligonucleotide (ASO).
(Method)

A myocardial infarction model was prepared as follows using 8 to 10 week-old mice (C57BL/6, male, SANKYO LABO SERVICE CORPORATION, INC.). After anesthesia by inhalation of 3 to 4% isoflurane, an oral intubation cannula was inserted into the trachea of the mouse, and the cannula was connected to a small animal ventilator for respiratory management. The precordial region of the mouse was incised about 1 cm, and the chest cavity and heart were exposed from the intercostal space with a retractor. A silicone tube was implanted in the central area above the left anterior descending branch of the coronary artery, and the same blood vessel (left anterior descending branch of the coronary artery) and the silicone tube were ligated with a suture to maintain the ischemic state of the left anterior descending branch while confirming the ST abnormality (abnormality in the ST area) on an electrocardiogram. After 60 minutes of ischemia, the silicone tube was removed and reperfusion was performed. Hemostasis was confirmed and skin sutures were performed, and the tube was extubated after confirmation of spontaneous respiration.

Immediately after reperfusion, the mouse was injected intravenously through a tail vein with Alexa-ASO or Alexa-Toc-HDO used in Example 1 at a dose of 10 mg/kg. Three hours after injection, the mouse was euthanized, perfused with PBS, and then dissected to isolate the heart. The isolated heart was immersed in isopentane cooled with liquid nitrogen and rapidly frozen and fixed. Thin sections of 20 µm were prepared from the heart. The sections were treated with DAPI and the nuclei were stained. The sections were observed for Alexa signals and nuclei by fluorescence microscopy.

(Results)

Figure 14:
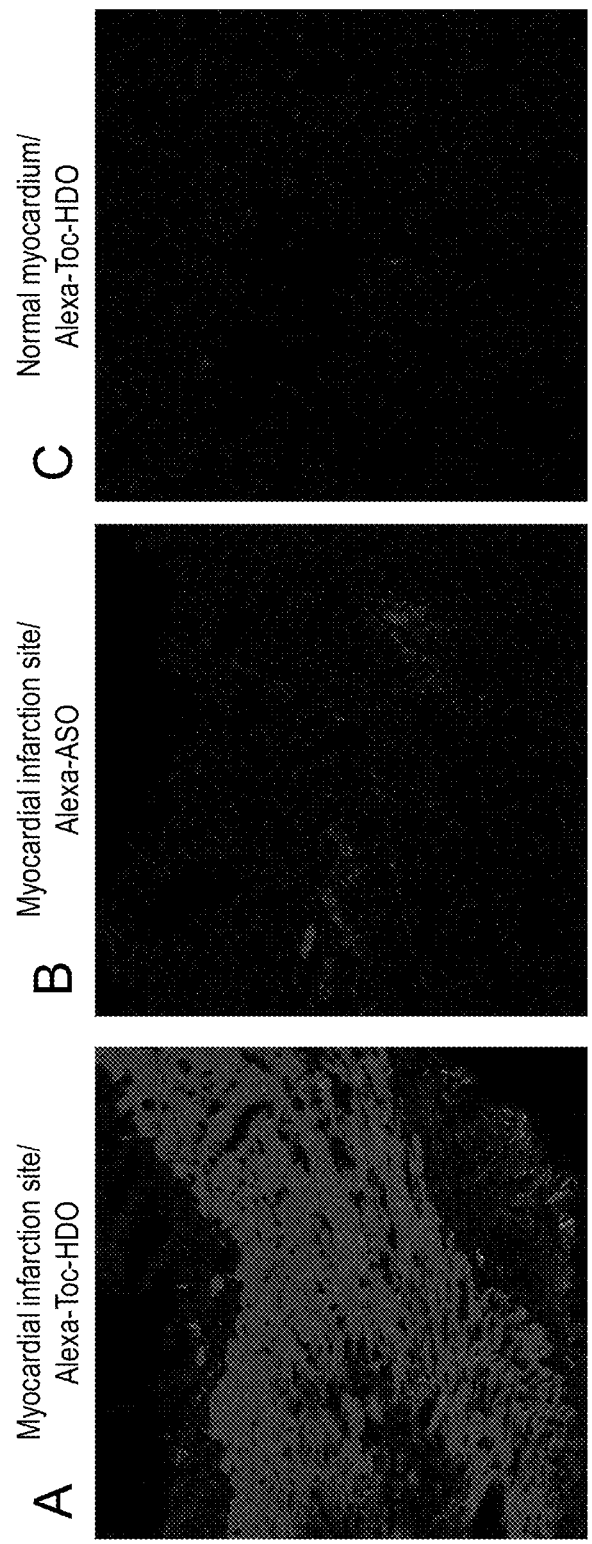
FIG. 14 shows fluorescence microscope images showing the results of Example 5, in which delivery of a lipid-ligand-conjugated double-stranded oligonucleotide to a myocardial infarction site was examined.

A very strong Alexa signal was detected across the entire area of myocardial infarction sites in the Alexa-Toc-HDO administration group (FIG. 14A). On the other hand, a weak Alexa signal was only found in myocardial infarction sites in the Alexa-ASO administration group (FIG. 14B). Further, in normal myocardium, only a weak dot-like Alexa signal was found in both Alexa-ASO administration group and Alexa-Toc-HDO administration group (FIG. 14C).

These results indicated that a lipid-ligand-binding heteroduplex oligonucleotide was delivered more efficiently to a myocardial infarction site than a single-stranded antisense oligonucleotide, and that the delivery was ischemic site selective.

Example 6

(Further Analysis of Delivery of Lipid-Ligand-Conjugated Duplex Oligonucleotide to Myocardial Infarction Site)

A myocardial infarction site to which a lipid-ligand-conjugated heteroduplex oligonucleotide is delivered was observed in more detail using a vascular endothelial cell marker.
(Method)

A myocardial infarction mouse model was prepared as described in Example 5, an Alexa-labeled lipid-ligand (tocopherol)-conjugated heteroduplex oligonucleotide (Alexa-Toc-HDO) was administered to the myocardial infarction mouse model, the heart was isolated, and thin sections were prepared.

The sections were immunostained with anti-CD31 antibody as a vascular endothelial cell marker as in Example 2. The sections were treated with DAPI to stain the nuclei. The sections were observed for Alexa signals, CD31 signals, and nuclei by fluorescence microscopy.
(Results)

Figure 15:
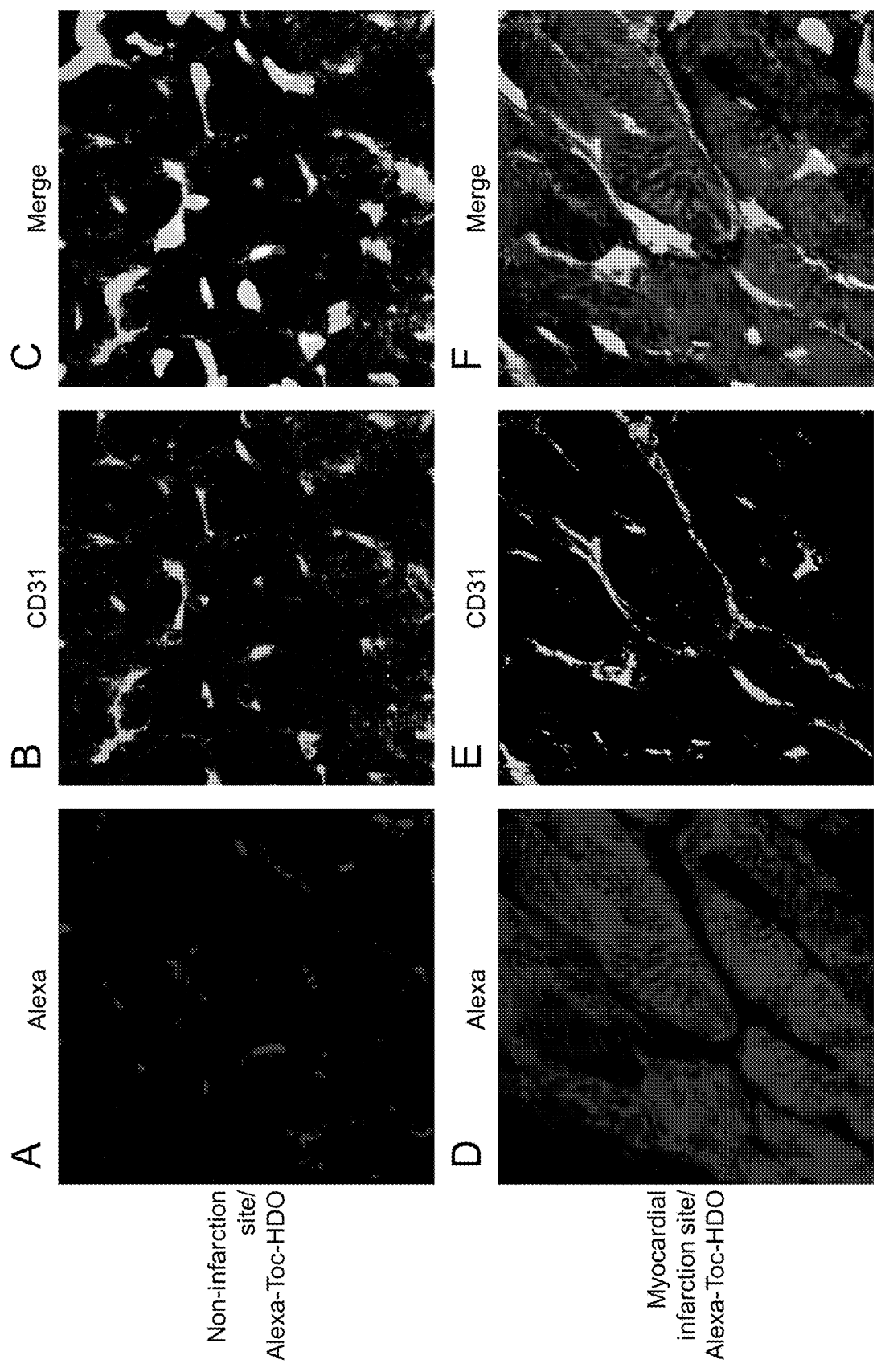
FIG. 15 shows fluorescence microscope images showing the results of Example 6, in which delivery of a lipid-ligand-conjugated double-stranded oligonucleotide to a myocardial infarction site was further analyzed.
Figure 16:
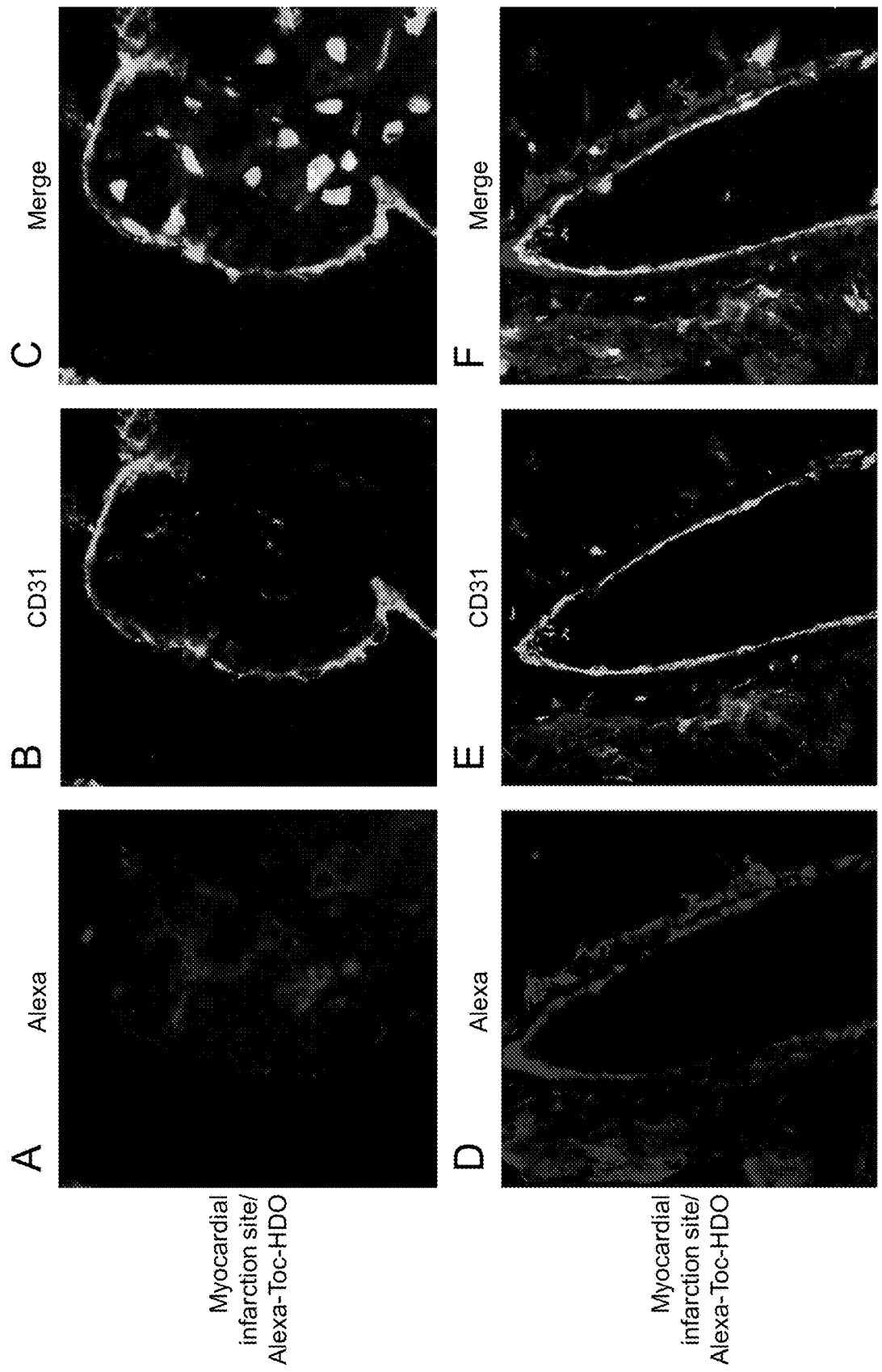
FIG. 16 shows fluorescence microscope images showing the results of Example 6, in which delivery of a lipid-ligand-conjugated double-stranded oligonucleotide to a myocardial infarction site was further analyzed.

In a non-infarction site in a myocardial infarction mouse model to which Alexa-Toc-HDO was administered, an Alexa signal was found only in some vascular endothelial cells (FIGS. 15A to 15C). On the other hand, in a myocardial infarction site in a myocardial infarction mouse model to which Alexa-Toc-HDO was administered, there was a strong Alexa signal not only in vascular endothelial cells but also in the myocardium (FIGS. 15D to 15F). In a myocardial infarction site in a myocardial infarction mouse model to which Alexa-Toc-HDO was administered, there was a strong Alexa signal in the special cardiac muscle, which controls the heartbeat (FIG. 16A to 16C), as well as in not only vascular endothelial cells, but also endothelial cells of large arteries such as coronary arteries (coronary artery endothelial cells) and smooth muscle cells (FIGS. 16D to 16F).

These results indicated that a lipid-ligand-conjugated heteroduplex oligonucleotide was efficiently delivered to a vascular endothelial cell of a myocardial infarction site, as well as to a myocardium beyond a blood vessel, and also to a special cardiac muscle, coronary artery endothelial cell, and smooth muscle cell.

Example 7

(Delivery of Lipid-Ligand-Conjugated Duplex Oligonucleotide to Lower Limb Ischemia Site in Arteriosclerosis Obliterans Model)

Whether a lipid-ligand-conjugated heteroduplex oligonucleotide is delivered to a lower limb ischemic site in an arteriosclerosis obliterans model was examined in comparison with a conventional antisense oligonucleotide (ASO).

(Method)

8 to 10 week-old mice (BALB/c, male, Sankyo Lab Services, Inc.) were used to prepare an arteriosclerosis obliterans model as follows. After induction of anesthesia by inhalation of 3 to 4% isoflurane, anesthesia was maintained with 2 to 2.5% isoflurane, the right thigh was incised approximately 1 cm, the femoral artery was separated from the femoral vein and femoral nerve just below the inguinal ligament, four positions of femoral arteries in total, two proximal and distal to the femoral artery and two branches therebetween, were ligated, and the femoral artery was excised. Subsequently, hemostasis was confirmed and skin sutures were performed to prepare an arteriosclerosis obliterans mouse model.

Three hours after ligation (ischemia), Alexa-ASO or Alexa-Toc-HDO at a dose of 10 mg/kg was injected intravenously through a tail vein into an arteriosclerosis obliterans mouse model. The Alexa-ASO and Alexa-Toc-HDO used in the present Example are the same as the Alexa-ASO and Alexa-Toc-HDO described in Example 1, respectively, except that AlexaFluor647 was used instead of the fluorescent dye AlexaFluor568.

Three hours after injection, the mouse was euthanized, perfused with PBS, and then dissected to isolate the lower limb skeletal muscles. The right lower limb skeletal muscle was defined as ischemic lower limb skeletal muscle, and the left lower limb skeletal muscle was defined as non-ischemic (healthy) lower limb skeletal muscle. An isolated lower limb skeletal muscle was immersed in isopentane cooled with liquid nitrogen, and rapidly frozen and fixed. Thin sections of 20 μm were prepared from the lower limb skeletal muscle. The sections were treated with DAPI to stain the nuclei, and observed for Alexa signals and nuclei by fluorescence microscopy. 20 μm thin sections were prepared from ischemic and non-ischemic (healthy) lower limb skeletal muscle of a mouse 3 hours after ligation (ischemia), the sections were stained with hematoxylin and eosin (HE), and observed under a microscope.

(Results)

Figure 17:
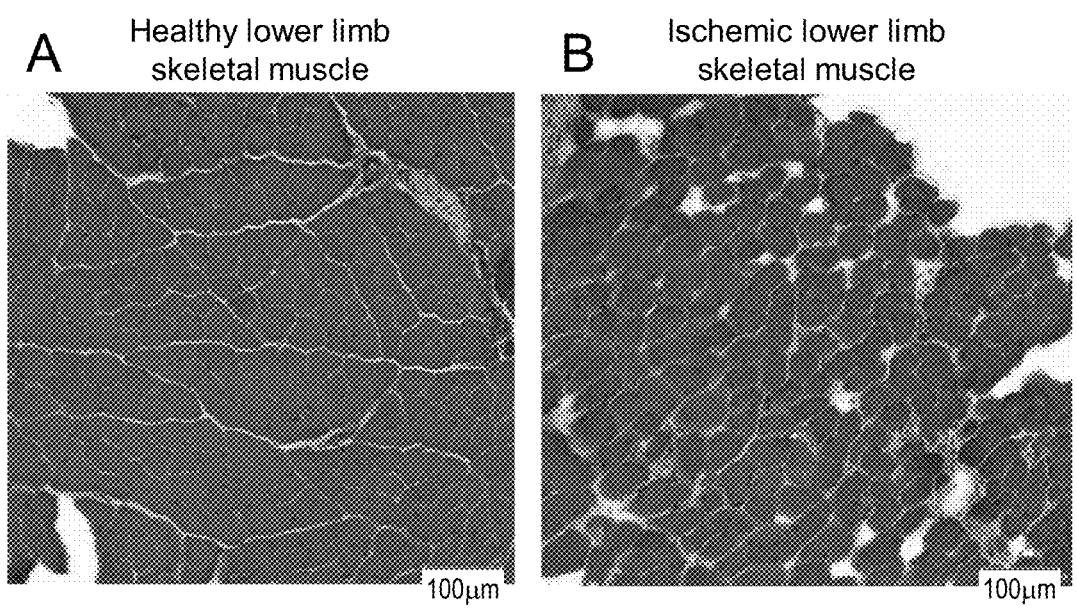
FIG. 17 shows photographs of hematoxylin-eosin (HE) treated specimens of the lower limb skeletal muscle of an arteriosclerosis obliterans mouse model produced in Example 7.

As shown in HE-stained specimens in FIGS. 17A and 17B, there was mild muscle fiber circularization and increased nuclear components in an ischemic lower limb skeletal muscle (FIG. 17B) compared with a healthy lower limb skeletal muscle (FIG. 17A), confirming that ligation of the femoral artery could prepare an arteriosclerosis obliterans model.

Figure 18:
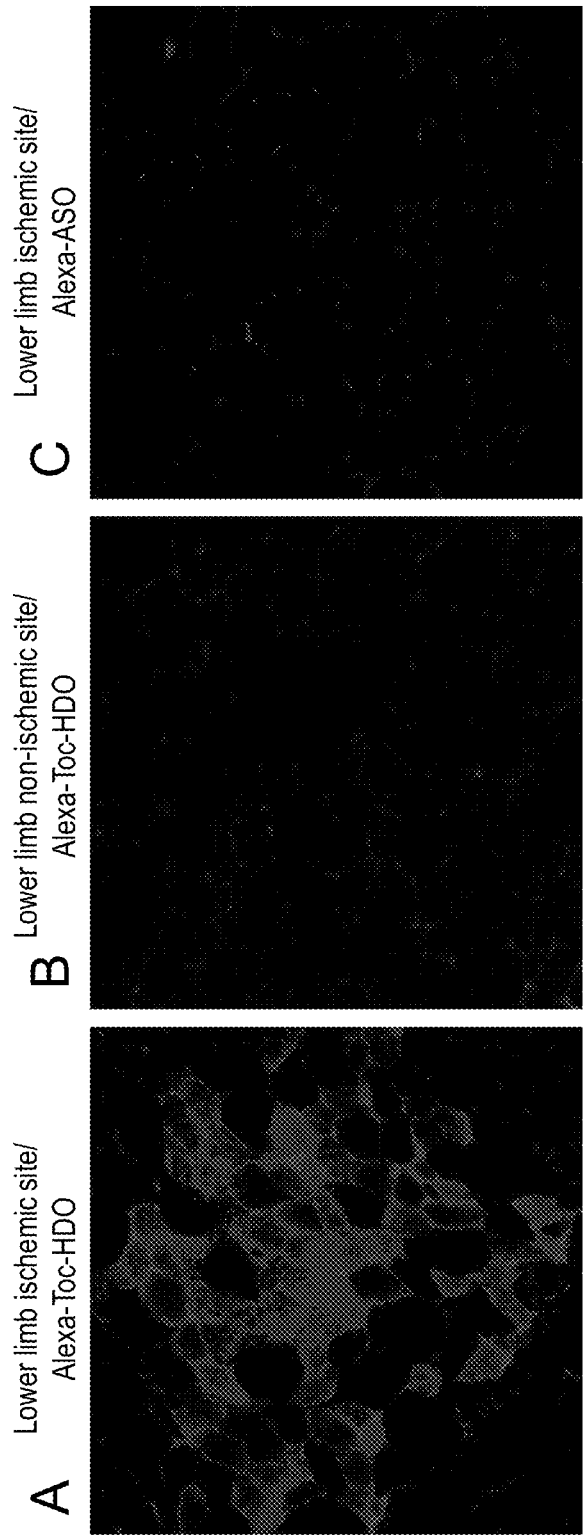
FIG. 18 shows fluorescence microscope images showing the results of Example 7, in which delivery of a lipid-ligand-conjugated double-stranded oligonucleotide to a lower limb ischemic site in arteriosclerosis obliterans model mice was examined.
Figure 19:
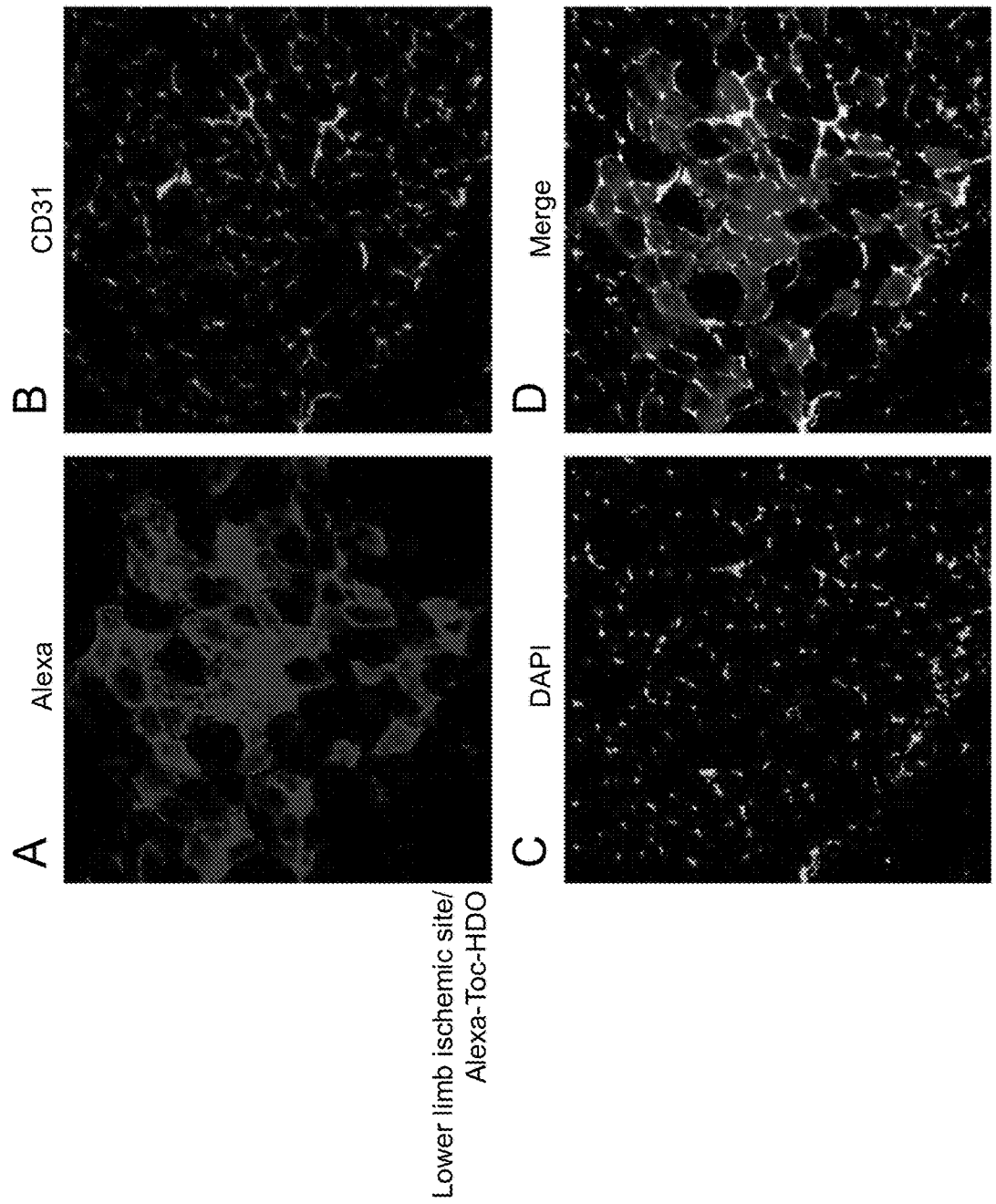
FIG. 19 shows fluorescence microscope images showing the results of Example 8, in which delivery of a lipid-ligand-conjugated double-stranded oligonucleotide to a lower limb ischemic site was further analyzed.

In the ischemic lower limb skeletal muscle of the Alexa-Toc-HDO administration group, a very strong Alexa signal was observed not only in endothelial cells but also in skeletal muscle cells and nerve fibers (FIG. 18A). On the other hand, in the non-ischemic lower limb skeletal muscle of the Alexa-Toc-HDO administration group, only a weak Alexa signal was found in vascular endothelial cells (FIG. 18B). In the Alexa-ASO administration group, only point-like Alexa signals were found in some endothelial cells, even in the ischemic lower limb skeletal muscle (FIG. 18C).

These results indicated that a lipid-ligand-conjugated heteroduplex oligonucleotide was delivered more efficiently to a lower limb ischemic site than a single-chain-antisense oligonucleotide, and the delivery thereof was ischemic site selective.

Example 8

(Further Analysis of Delivery of Lipid-Ligand-Conjugated Duplex Oligonucleotide to Lower Limb Ischemic Site)

A lower limb ischemic site to which a lipid-ligand-conjugated heteroduplex oligonucleotide is delivered was observed in more detail using a vascular endothelial cell marker.

(Method)

An arteriosclerosis obliterans mouse model was prepared as described in Example 7, an Alexa-labeled lipid-ligand (tocopherol)-conjugated heteroduplex oligonucleotide (Alexa-Toc-HDO) was administered to the arteriosclerosis obliterans mouse model, an ischemic lower limb skeletal muscle was isolated, and thin sections were prepared.

The sections were immunostained with anti-CD31 antibody as a vascular endothelial cell marker as in Example 2. Further, the sections were treated with DAPI to stain the nuclei. The sections were observed for Alexa signals, CD31 signals, and nuclei by fluorescence microscopy.

(Results)

In an ischemic lower limb skeletal muscle of an arteriosclerosis obliterans mouse model to which Alexa-Toc-HDO was administered, an Alexa signal was observed in vascular endothelial cells, and an Alexa signal was observed also in skeletal muscle (FIGS. 19A to 19D). The results indicated that a lipid-ligand-conjugated heteroduplex oligonucleotide was efficiently delivered to vascular endothelial cells in a lower limb ischemic site, as well as to skeletal muscle beyond blood vessels.

Example 9

(Inhibition of Target Gene Expression in Arteriosclerosis Obliterans Model Mice)

An effect of inhibiting expression of a target gene in an arteriosclerosis obliterans mouse model by a lipid-ligand-conjugated heteroduplex oligonucleotide was examined in comparison with an antisense oligonucleotide (ASO).

(Method)

The LNA/DNA gapmer ASO to which a fluorescent dye was not conjugated and the lipid-ligand (tocopherol)-conjugated heteroduplex oligonucleotide (Toc-HDO) used in Example 3 were used in the present Example.

An arteriosclerosis obliterans mouse model was prepared using the same protocol as in Example 7, and 3 hours after arterial occlusion, ASO or Toc-HDO at a dose of 10 mg/kg was injected intravenously through a tail vein. Seventy-two hours after injection (75 hours after arterial occlusion), the mouse was euthanized, perfused with PBS, and then the ischemic lower limb skeletal muscle was isolated. RNA was extracted from the isolated ischemic lower limb skeletal muscle, and the Malat-1 gene expression level was quantified by quantitative RT-PCR as in Example 3. A relative Malat-1 level was obtained by normalizing the Malat-1 expression level to the Gapdh mRNA expression level.

(Results)

Figure 20:
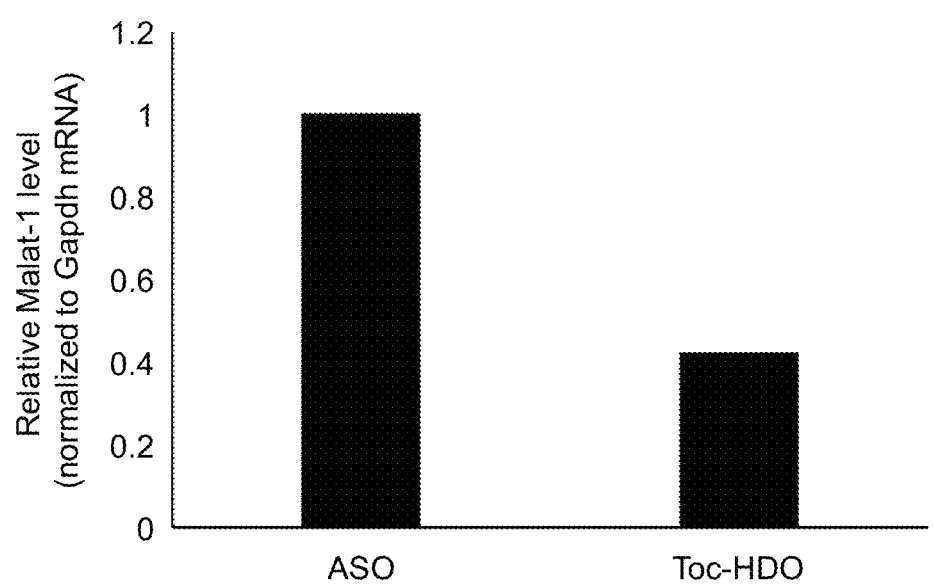
FIG. 20 is a graph showing the results of Example 9, in which an inhibition of target gene expression by a lipid-ligand-conjugated double-stranded oligonucleotide in an arteriosclerosis obliterans mouse model was examined by quantitative RT-PCR method.

In an ischemic lower limb skeletal muscle, the Malat-1 gene expression was greatly reduced in the Toc-HDO administration group compared with the ASO administration group (FIG. 20). These results indicated that a lipid-ligand-conjugated heteroduplex oligonucleotide could achieve stronger inhibition of a gene in a lower limb ischemia site than a single-stranded antisense oligonucleotide.

Example 10

(Increase of Lipid Receptors in Acute Phase of Ischemic Stroke)

Whether lipid-conjugated receptors were increased in an ischemic pathology (particularly in the acute phase of ischemic stroke) was examined.

(Method)

Ischemic stroke mouse model was prepared as described in Example 1, and after 3, 6, 9, and 15 hours of vascular occlusion and after 1 day of vascular occlusion (n=4 for each group), the mice were perfused with PBS, and then dissected to isolate the ischemic (ischemic stroke) cerebral hemisphere. In the ischemic cerebral hemisphere, the mRNA expression levels and protein levels of major lipid receptors in vivo (LDLR (low density lipoprotein receptor), SRBI (scavenger receptor class B type I), and LRP1 (LDL receptor-related protein-1)) were measured.

The mRNA expression amounts were measured by quantitative RT-PCR as in Example 3 and compared with the non-ischemic group (sham surgery group). PCR primers used were mouse LDLR (Mm00440169_m1), SRB1 (Mm00450234_m1), and LRP1 (Mm00464608_m1) from TaqMan Gene Expression Assays (Applied Biosystems).

The amount of protein was measured as follows. Isolated brain was homogenized, the protein concentration was measured using a Pierce BCA Protein Assay kit (Thermo Fisher Scientific, Waltham, Mass.), and the purified proteins were electrophoresed on SDS polyacrylamide gels (ATTO Corporation, Tokyo, Japan) and transferred to a polyvinylidene fluoride (PVDF) membrane. Bands were detected by western blotting using rabbit anti-LDLR antibody (ab30532, Abcam), rabbit anti-SRB1 antibody (ab217318, Abcam), or rabbit anti-LRP1 antibody (ab92544, Abcam) as primary antibodies, and the detected bands were quantified by the ChemiDoc Touch Imaging System (Bio-Rad Laboratories). An anti-β-actin antibody (1:2000 dilution, Wako Pure Chemical Co., Ltd., Osaka, Japan) was used as a primary antibody for an internal control.

(Results)

Figure 22:
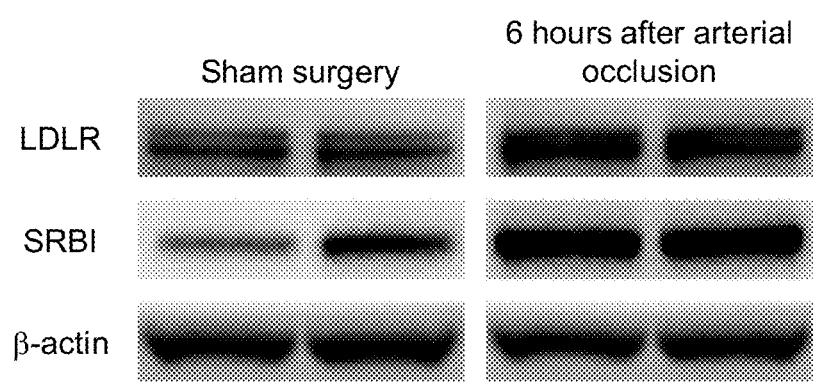
FIG. 22 shows photographs showing the results of Example 10, in which upregulation of lipid receptors expression in an acute phase of ischemic stroke was examined at the protein level.

As shown in FIGS. 21A to 21C, LDLR, SRBI, and LRP1 were all significantly increased at the mRNA level in a brain in hyperacute phase within 24 hours of ischemia compared with normal brain (sham-operation) (FIG. 21, $*p<0.05$, $p<0.01$, $*p<0.001$). Further, as shown in FIG. 22, in both LDLR and SRBI, the protein level was also significantly increased in the brain after 6 hours of ischemia compared with the non-ischemic cerebral hemisphere (sham-operation). The increase in lipid receptor expression in the ischemic stroke hyperacute phase (in particular, within 12 hours of onset), when there is no physical disruption of the blood-brain barrier, has never been reported before and is the first finding.

Example 11

(Identification of Cell Types with Increased Lipid Receptor Expression)

Cell types with increased lipid receptor expression, as shown in Example 10, were identified using a vascular endothelial cell marker and a neuronal cell marker.

(Method)

Ischemic stroke model mice were prepared as described in Example 1, and after 6 hours, the mice were perfused with PBS and then dissected to isolate the cerebrum. The cerebellum was isolated also from non-ischemic mice (sham surgery mice) in the same way. The isolated cerebellum was fixed in 4% PFA, and 20 μm thin sections were prepared. Sections were immunohistochemically stained with an anti-LDLR antibody, an anti-SRBI antibody, or an anti-LRP1 antibody in combination with an anti-CD31 antibody (a vascular endothelial cell marker) or an anti-NeuN antibody (a neuronal cell marker) as primary antibodies and observed by fluorescence microscopy. The anti-LDLR antibody, the anti-SRBI antibody, and the anti-LRP1 antibody are described in Example 10. The anti-CD31 antibody and the anti-NeuN antibody are described in Example 2.

(Results)

Figure 23:
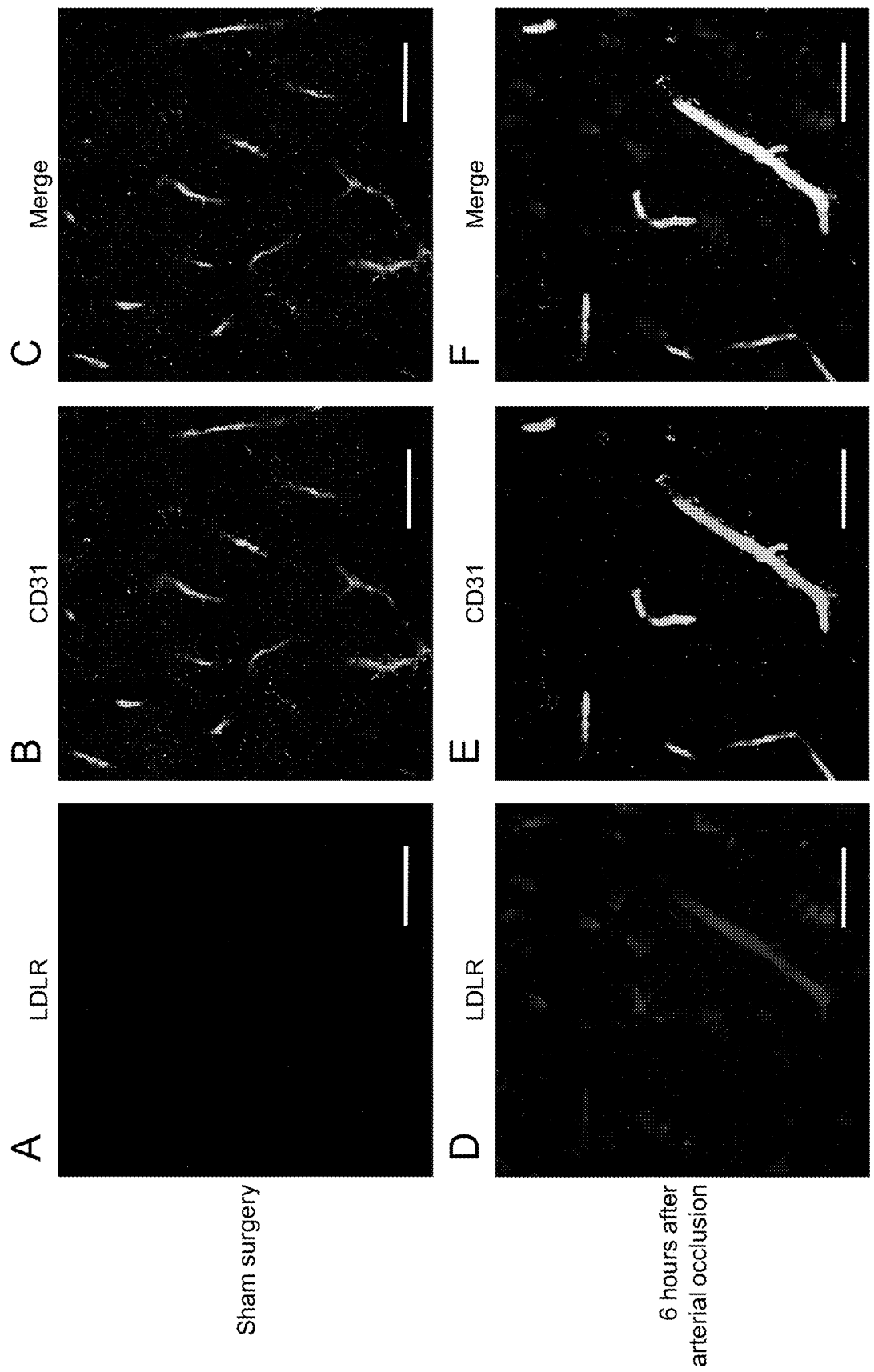
FIG. 23 shows fluorescence microscope images showing the results of Example 11, in which a cell type increasing expression of the lipid receptor LDLR in an acute phase of ischemic stroke was identified using a vascular endothelial cell marker.

Immunostaining for LDL receptors (LDLR) revealed little expression of LDL receptors in the non-ischemic brain (sham surgery) (FIG. 23A), and increased expression of LDL receptors in the brain 6 hours after ischemic stroke (ischemic stroke hyperacute phase) (FIG. 23D). The increased expression of LDL receptors was noticeably found mainly in CD31-positive vascular endothelial cells (FIGS. 23D to 23F) and in neuronal cells in the brain parenchyma.

Figure 24:
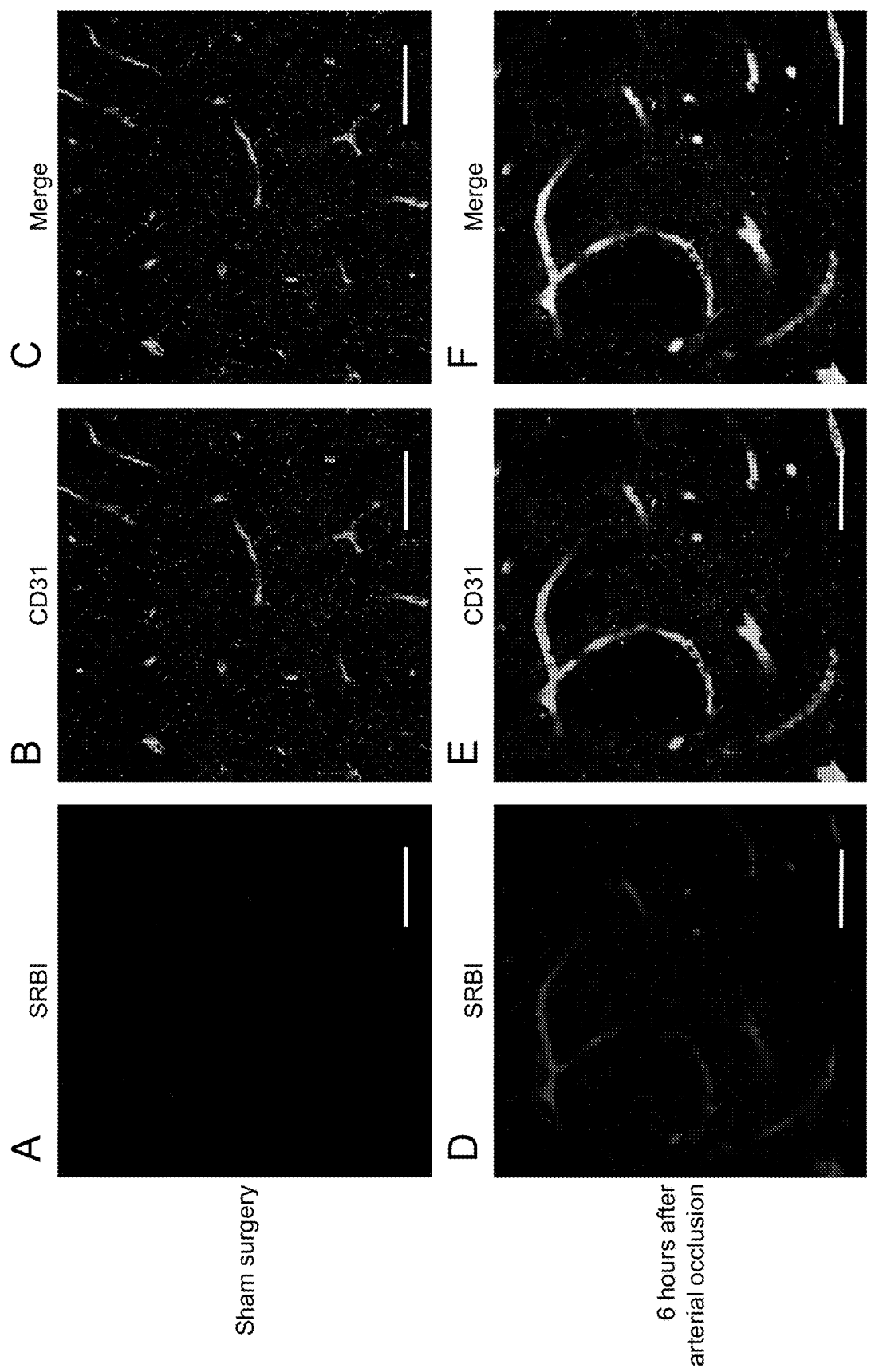
FIG. 24 shows fluorescence microscope images showing the results of Example 11, in which a cell type increasing expression of the lipid receptor SRBI in an acute phase of ischemic stroke was identified using a vascular endothelial cell marker.

Immunostaining for SRBI showed little SRBI expression in the non-ischemic brain (sham surgery) (FIG. 24A), and increased SRBI expression in the brain 6 hours after ischemic stroke (ischemic stroke hyperacute phase) (FIG. 24D). Expression of SRBI was mainly observed in CD31-positive vascular endothelial cells (FIGS. 24D to 24F).

Figure 25:
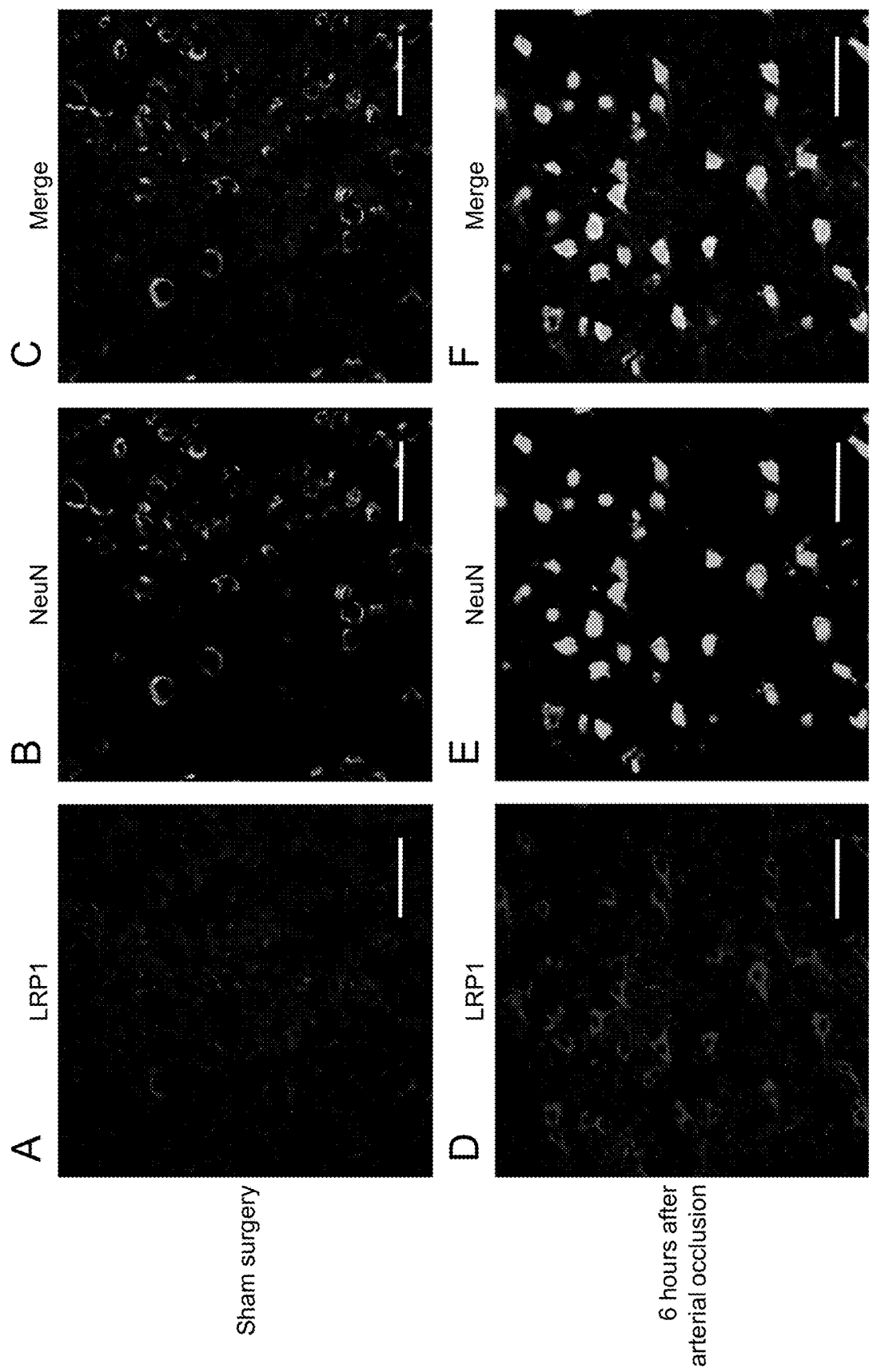
FIG. 25 shows fluorescence microscope images showing the results of Example 11, in which a cell type increasing expression of the lipid receptor LPR1 in an acute phase of ischemic stroke was identified using a neuronal cell marker.

Immunostaining for LRP1 revealed that in non-ischemic brains (sham surgery), LRP1 showed only a dot-like signal (FIG. 25A). The expression of LRP1 was increased in the brain 6 hours after ischemic stroke (ischemic stroke hyperacute phase) (FIG. 25D). The expression of LRP1 was mainly observed in NeuN-positive neuronal cells (FIGS. 25D to 25F).

These results indicated that lipid receptor expression is increased in cerebral vascular endothelial cells and neuronal cells in the ischemic stroke acute phase.

Example 12

(Examination of Vascular Permeability in Ischemic Stroke Hyperacute Phase Using LDL Receptor Knockout Mice)

Ischemic stroke was induced in an LDL receptor (LDLR) knockout mouse, and vascular permeability was examined in the ischemic stroke hyperacute phase.

(Method)

LDL receptor knockout mice (C57BL/6J; B6.129S7-Ldlr (tmlHer)/J (Ldlr−/−) mice (Jackson Laboratory, Me., USA); see Ishibashi S, et al. "Hypercholesterolemia in low density lipoprotein receptor knockout mice and its reversal by adenovirus-mediated gene delivery", *J Clin Invest*. 1993; 92(2):883-93) and normal C57BL6J mice (wild type) were used to prepare an ischemic stroke model as described in Example 1. Three hours after the ischemic stroke model was prepared, Evans Blue (Wako Pure Chemical Industries, Ltd., 054-04062) was diluted in physiological saline and injected (4 ml/kg) into the mouse via a tail vein. Three hours after injection (6 hours after ischemic stroke), the mouse was perfused and fixed with 4% PFA to isolate the brain. Photographs of the lateral view of the brain were taken. Subsequently, the isolated brains were sliced 2 mm thick and imaged with a stereomicroscope, and Evans Blue-positive regions were quantified.

(Results)

Figure 26:
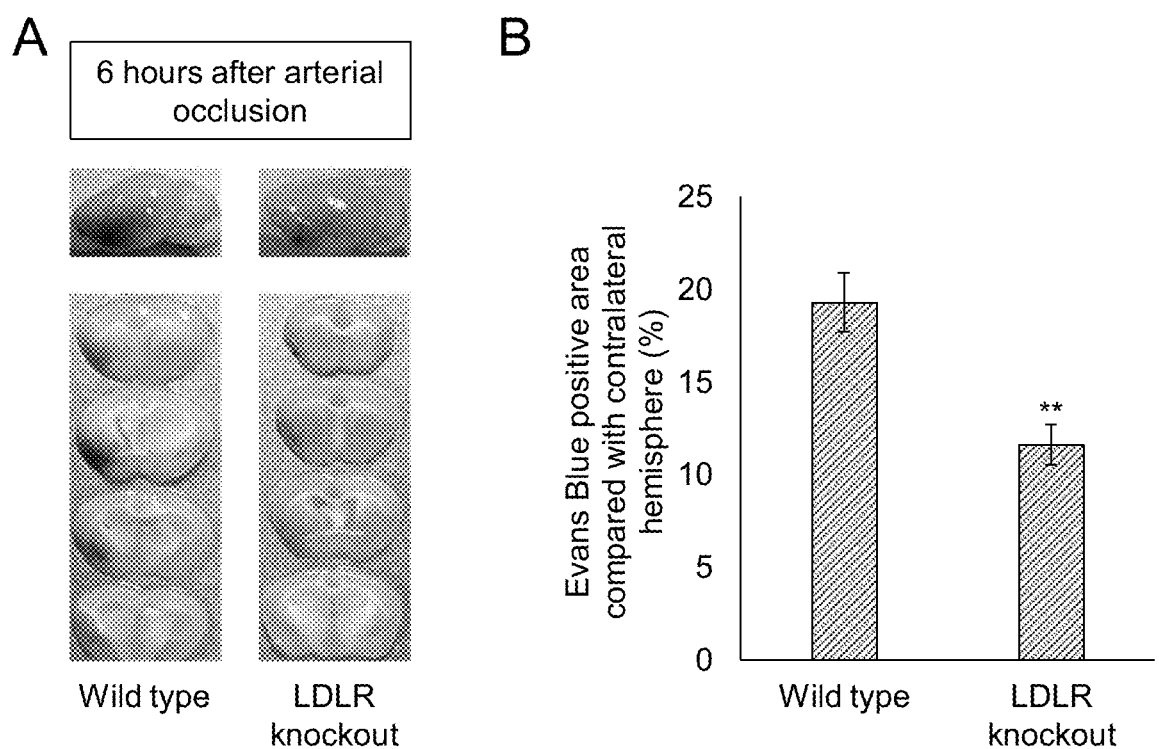
FIG. 26 shows diagrams showing the results of Example 12, in which the vascular permeability in an ischemic stroke hyper-acute phase was examined using an LDL receptor (LDLR) knockout mouse.

The Evans Blue-positive region of the brain represent a region with increased vascular permeability. As shown in the photographs in FIG. 26A and the graph in FIG. 26B, in normal mice, the Evans Blue-positive region was widely distributed throughout the occluded middle cerebral artery region, and in LDL receptor knockout mice, the region was significantly reduced (FIG. 26B, **p<0.01).

These results indicated that the ability of delivery into the brain parenchyma in the ischemic stroke hyperacute phase was reduced in lipid receptor knockout mice, thus indicating that lipid receptors such as LDLRs play an important role in enhancing vascular permeability in the ischemic stroke hyperacute phase, when the blood-brain barrier is not disrupted.

The results of Examples 10 to 12 indicated that the expression of lipid receptors was increased in cerebral vascular endothelial cells and neuronal cells in the brain parenchyma in the ischemic stroke hyperacute phase, and that lipid receptors are responsible for the increase in vascular permeability in the ischemic stroke hyperacute phase. These results suggested a mechanism for the efficient delivery of a lipid-conjugated heteroduplex oligonucleotide to cerebral vascular endothelial cells and brain parenchyma through a transcellular pathway via lipid receptors.

Example 13

(Increased Lipid Receptors in Arteriosclerosis Obliterans Model)

Changes in expression of lipid receptors in ischemic pathologies other than ischemic stroke as shown in Examples 10 to 12 were examined in an arteriosclerosis obliterans model.
(Method)

An arteriosclerosis obliterans mouse model was prepared as described in Example 7, and after 3 hours of perfusion of the mouse with PBS, the mouse was dissected to isolate ischemic side skeletal muscles. Skeletal muscles were isolated in the same way from a non-ischemic mouse (sham surgery mouse). The mRNA expression levels of LDLR, SRBI, and LRP1 were measured by quantitative RT-PCR and compared with the non-ischemic group (sham surgery group), as described in Example 10.
(Results)

Figure 27:
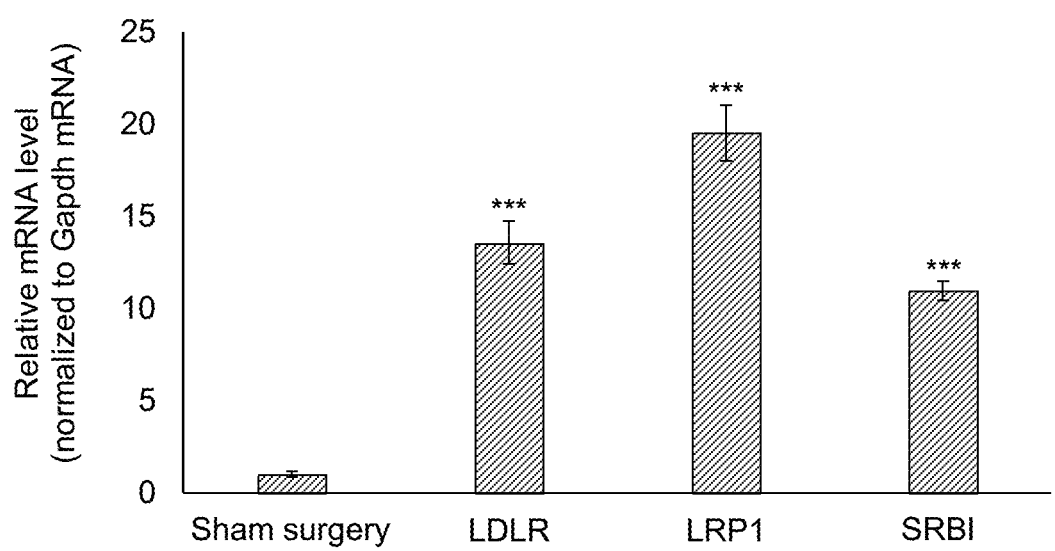
FIG. 27 is a graph showing the results of Example 13, in which an increase in a lipid receptor in an arteriosclerosis obliterans mouse model was examined.

LDL receptor (LDLR), SRBI, and LRP1 mRNA expression levels were significantly increased in the arteriosclerosis obliterans model, similarly to the ischemic stroke model in Example 10 (FIG. 27, ***p<0.001). This indicated that the increase in lipid receptors was a characteristic change in ischemic pathology. Thus, the mechanism of delivery of a lipid-conjugated heteroduplex oligonucleotide to an ischemic site via a lipid receptor, as described in Example 12, was suggested to be applicable to an arteriosclerosis obliterans model as well.

Example 14

(Delivery of Cholesterol-Conjugated Duplex Oligonucleotide to Ischemic Stroke Site)

Delivery of cholesterol-conjugated heteroduplex oligonucleotide to an ischemic stroke site (ischemic lesion) was compared with a conventional antisense oligonucleotide (ASO) and the like.
(Method)

Ischemic stroke model mice were prepared as described in Example 1, and 3 hours after arterial occlusion, the mice were randomly divided into five groups (n=4 per group), and to each group, PBS or 50 mg/kg of ASO, HDO, Toc-HDO, or Cho-HDO was administered through a tail vein.

The same ASO and Toc-HDO were prepared as described in Example 1, and HDO which is the same as Toc-HDO as described in Example 1 except that no tocopherol was conjugated at the 5' end was prepared in accordance with the method described in Example 1.

Cho-HDO was prepared as follows. First, ASO (Alexa-ASO) with AlexaFluor568 covalently bound to the 5' end of the LNA/DNA gapmer ASO as described in Example 1 was prepared. Subsequently, a complementary RNA strand (Cho-cRNA) with cholesterol instead of tocopherol conjugated at the 5' end of the cRNA was prepared for the Toc-cRNA described in Example 1. An Alexa-labeled lipid-ligand (cholesterol)-conjugated heteroduplex oligonucleotide (Cho-HDO) was prepared by annealing the prepared Alexa-ASO and Cho-cRNA according to the method described in Example 1. After 3 days of arterial occlusion, Malat-1 RNA expression amount was measured by quantitative RT-PCR according to the method described in Example 3, and a gene inhibition effect was compared.
(Results)

Figure 28:
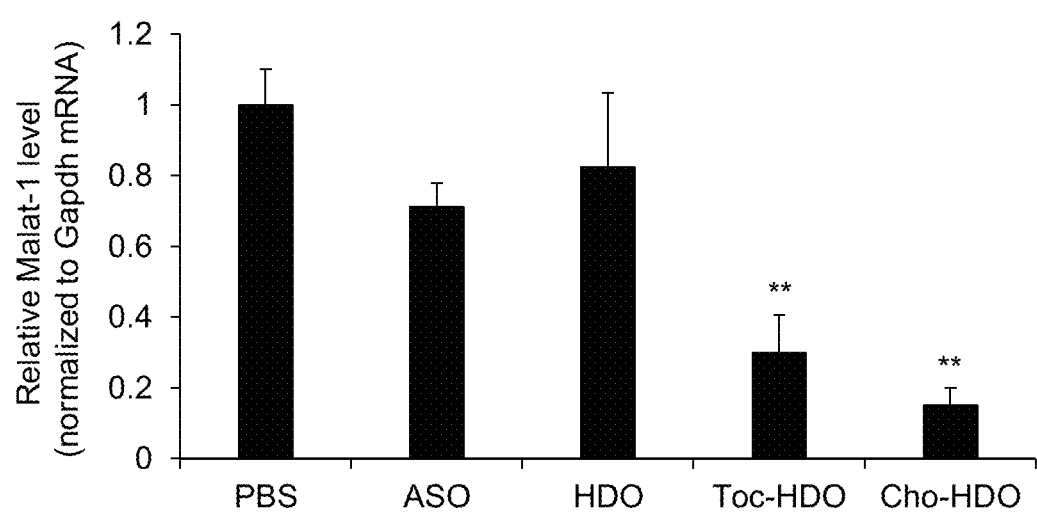
FIG. 28 is a graph showing the results of Example 14, in which an inhibition of target gene expression by a lipid-ligand-conjugated double-stranded oligonucleotide in ischemic stroke mouse model was examined by quantitative RT-PCR method.

The gene inhibition effect of PBS on the ischemic cerebral hemisphere is shown in FIG. 28 (**p<0.01). As shown in FIG. 28, HDO without ASO and lipid ligands did not show a prominent gene inhibition effect. In contrast, Toc-HDO and Cho-HDO showed a prominent gene inhibition effect, and particularly when cholesterol was used, the highest effect was observed.

These results indicated that HDO without lipid ligands has a poor gene inhibition effect in the central nervous system similarly to ASOs, but when a lipid ligand such as Toc or Cho is conjugated, the inhibition effect thereof was significantly increased.

Example 15

(Examination of Gene Inhibition Effect in Ischemic Stroke Hyperacute Phase Using LDL Receptor Knockout Mice)

Whether the delivery of a lipid-ligand-conjugated HDO to an ischemic cerebral hemisphere is mediated by an LDL receptor was examined using an LDL receptor knockout mouse.
(Method)

An ischemic stroke model was prepared using an LDL receptor knockout mouse (C57BL/6J) and a normal C57BL6J mouse (WT) in accordance with Example 12. Three hours after arterial occlusion, 50 mg/kg of Toc-HDO prepared in Example 14 was administered via a tail vein, and 3 days after arterial occlusion, the expression level of Malat-1 RNA was measured by quantitative RT-PCR according to the method described in Example 3 to compare the gene inhibition effect (n=4 per group).
(Results)

Figure 29:
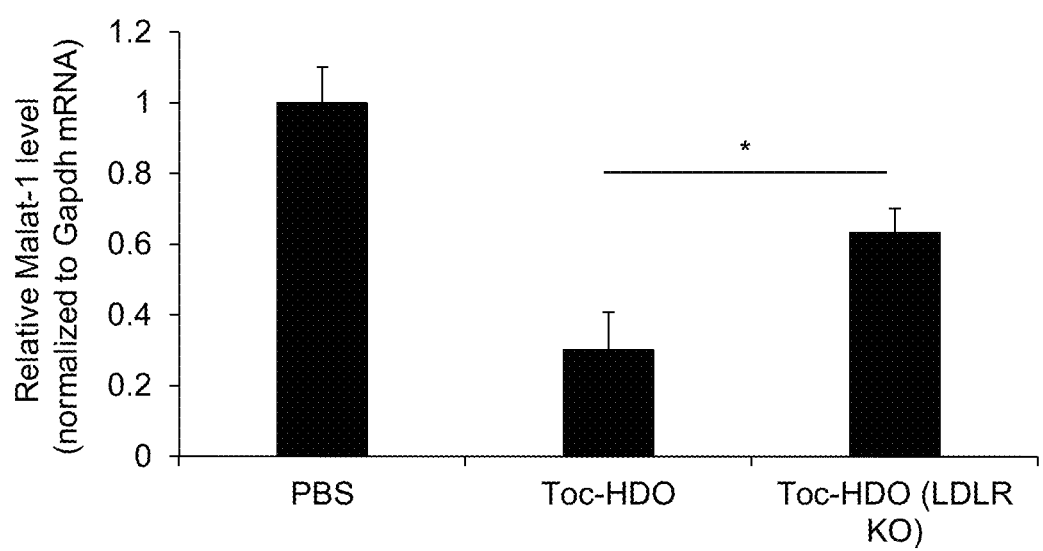
FIG. 29 is a graph showing the results of Example 15, in which an inhibition of target gene expression by a lipid-ligand-conjugated double-stranded oligonucleotide in an ischemic stroke mouse model with LDL receptor knockout was examined by quantitative RT-PCR method.

As shown in FIG. 29, an inhibition effect on the Malat-1 gene by Toc-HDO was observed in the ischemic cerebral hemisphere, and the gene inhibition effect was significantly decreased in an LDL receptor knockout (LDLR KO) mouse (*p<0.05).

This result suggested that an LDL receptor was involved in the delivery of lipid ligand-conjugated HDO to the ischemic cerebral hemisphere.

Example 16

(Examination of Delivery Effect of Tocopherol-Conjugated HDO in Myocardial Infarction Model)

Whether a tocopherol-conjugated heteroduplex oligonucleotide is delivered to an ischemia site in a myocardial infarction model was examined in comparison with a conventional antisense oligonucleotide (ASO).

(Method)

A myocardial infarction model was prepared as described in Example 5, and after 1 hour, 10 mg/kg of Alexa-ASO or 10 mg/kg of Alexa-Toc-HDO prepared according to Example 1 was administered via a tail vein, and after 3 hours, the delivery efficiency to a tissue was quantitatively compared by the fluorescence intensity of Alexa according to the method described in Example 1 (n=3 per group).
(Results)

Figure 30:
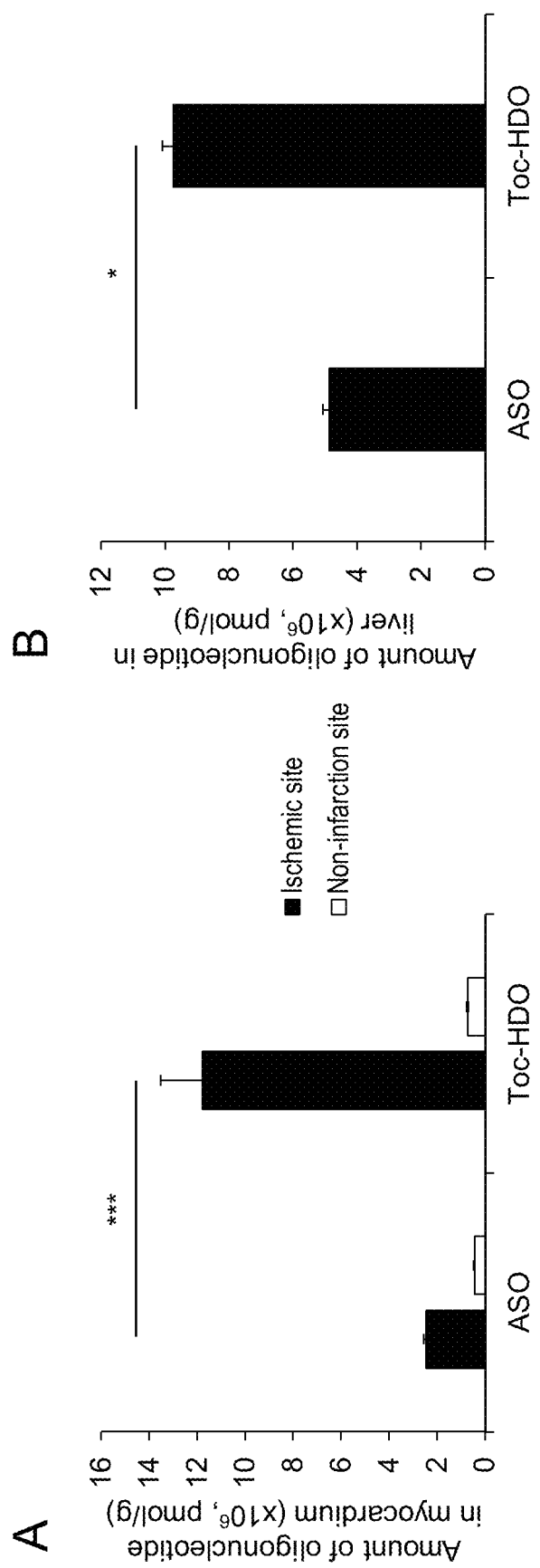
FIG. 30 is a graph showing the results of Example 16 showing the oligonucleotide amount in the organ isolated from a myocardial infarction mouse model administered with Alexa-ASO or Alexa-Toc-HDO.

As shown in FIG. 30, the delivery efficiency was slightly improved with Toc-HDO compared with ASO in a non-infarction site of a myocardial infarction mouse model ($*p<0.05$, $***p<0.001$). In an ischemic site, 5-fold or more improvement in delivery efficiency was observed with Toc-HDO compared with ASO. In a liver, the delivery efficiency of Toc-HDO was improved by about 2-fold compared with ASO.

These results indicated that delivery was ischemic site-selective and specific for a lipid-ligand-conjugated HDO. This is consistent with histological studies showing efficient delivery of Alexa-Toc-HDO to myocardial infarction as shown in Example 6.

Example 17

(Comparison of Inhibition Effect on Malat-1 RNA Expression in Myocardial Infarction Model Mice)

An effect of inhibiting target gene expression by a lipid-ligand-conjugated heteroduplex oligonucleotide in a myocardial infarction mouse model was examined in comparison with an antisense oligonucleotide (ASO).
(Method)

Myocardial infarction model mice were prepared as described in Example 5, and after one hour, the mice were randomly divided into five groups (n=4 per group), and to each group, PBS or 10 mg/kg of ASO, HDO, Toc-HDO, or Cho-HDO was administered via a tail vein. The methods for preparing ASO, HDO, Toc-HDO, and Cho-HDO were as described in Example 14. Three days after preparation of a myocardial infarction mouse model, the expression level of Malat-1 RNA was measured by quantitative RT-PCR according to the method described in Example 3, and a gene inhibition effect was compared.
(Results)

Figure 31:
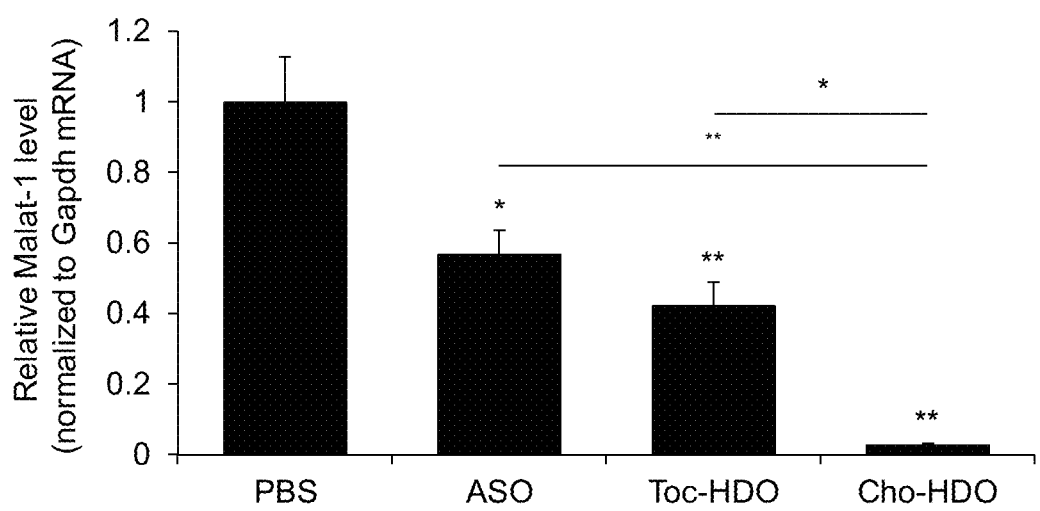
FIG. 31 is a graph showing the results of Example 17, in which an inhibition of target gene expression by a lipid-ligand-conjugated double-stranded oligonucleotide in myocardial infarction model mice was examined by quantitative RT-PCR method.

As shown in FIG. 31, a strong gene inhibition effect was observed in Toc-HDO and Cho-HDO compared with ASO also in a myocardial infarction mouse model, and the inhibition effect was particularly remarkable in Cho-HDO ($*p<0.05$, $**p<0.01$). Unlike the central nervous system, a sufficient inhibition effect was observed at a dose of 10 mg/kg (50 mg/kg for the brain).

Example 18

(Increased Lipid Receptors in Myocardial Infarction)

Whether lipid-binding receptors are increased in myocardial infarction was examined.
(Method)

Myocardial infarction model mice were prepared as described in Example 5, and after 3 days, the mRNAs of LDLR, LRP1, and SRBI were analyzed by quantitative RT-PCR according to the method described in Example 10. The analysis was performed at three sites: a site without ischemia, a pen-infarction site, and an infarction site.

(Results)

Figure 32:
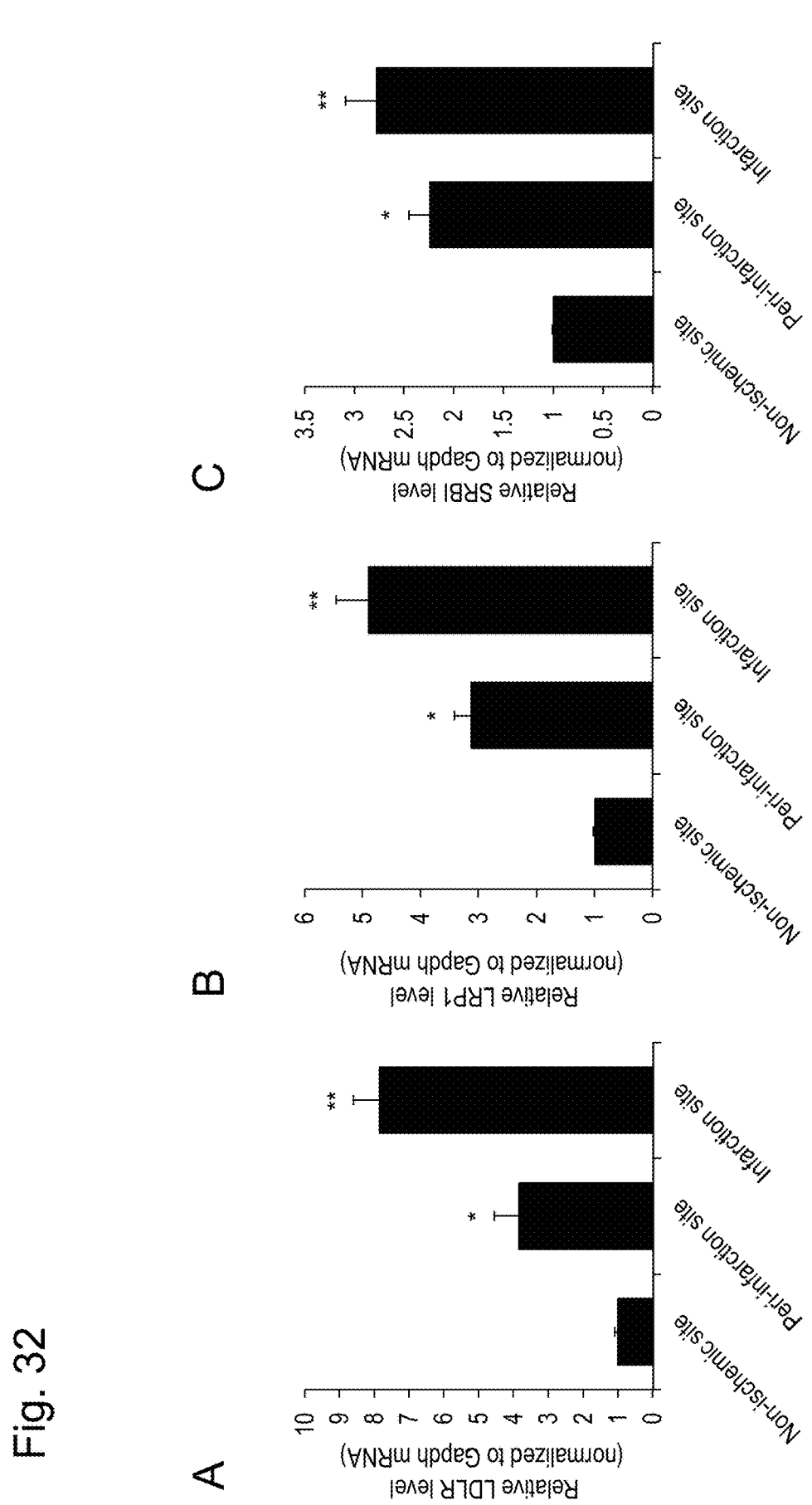
FIG. 32 shows graphs showing the results of Example 18, in which an increase in lipid receptor expression in a myocardial infarction was examined at the mRNA level.

As shown in FIG. 32, the expression of all lipid receptors was significantly increased in the pen-infarction and infarction sites compared with non-ischemic site ($*p<0.05$, $**p<0.01$).

Like in the ischemic stroke model, a high expression of lipid receptors was found in an ischemic site in the myocardial infarction model, which may be related to the increased efficiency of lipid-conjugated HDO delivery in an ischemic site.

Example 19

(Comparison of Effect of Inhibiting Malat-1 RNA Expression in Arteriosclerosis Obliterans Model)

The effect of inhibiting target gene expression by a lipid-ligand-conjugated heteroduplex oligonucleotide in an arteriosclerosis obliterans mouse model was examined in comparison with an antisense oligonucleotide (ASO).
(Method)

Arteriosclerosis obliterans models were prepared as described in Example 7, and after three hours, the mice were randomly divided into five groups (n=4 per group), and to each group, PBS or 10 mg/kg of ASO, HDO, Toc-HDO, or Cho-HDO was administered via a tail vein. The methods for preparing ASO, HDO, Toc-HDO, and Cho-HDO were in accordance with Example 14. Three days after preparation of an arteriosclerosis obliterans mouse model, the expression level of Malat-1 RNA was measured by quantitative RT-PCR according to the method described in Example 3, and a gene inhibition effect was compared.
(Results)

Figure 33:
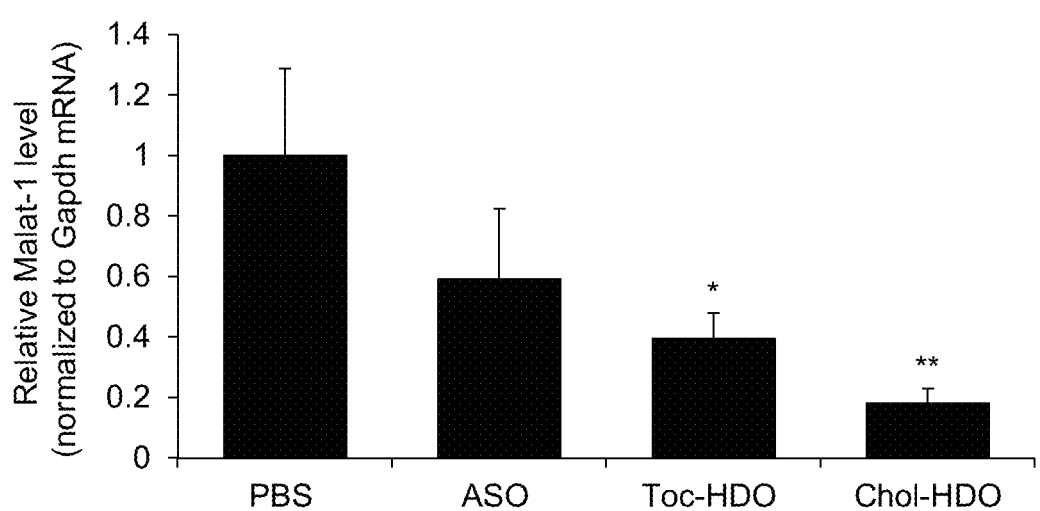
FIG. 33 is a graph showing the results of Example 19, in which an inhibition of target gene expression by a lipid-ligand-conjugated double-stranded oligonucleotide in arteriosclerosis obliterans model mice was examined by quantitative RT-PCR method.

As shown in FIG. 33, a strong gene inhibition effect was observed in Toc-HDO and Cho-HDO compared with ASO also in an arteriosclerosis obliterans mouse model, and the inhibition effect was particularly remarkable in Cho-HDO ($*p<0.05$, $**p<0.01$). Unlike the central nervous system, a sufficient inhibition effect was shown at a dose of 10 mg/kg (50 mg/kg for the brain).

Example 20

(Expression of Lipid Receptors in Arteriosclerosis Obliterans Model)

Increased expression of lipid receptors in an arteriosclerosis obliterans model was confirmed by immunofluorescence staining.
(Method)

An arteriosclerosis obliterans model was prepared as described in Example 7, and LDLRSRBI expression in this model was confirmed by immunofluorescence staining according to the method described in Example 11.
(Results)

Figures 1, 34:
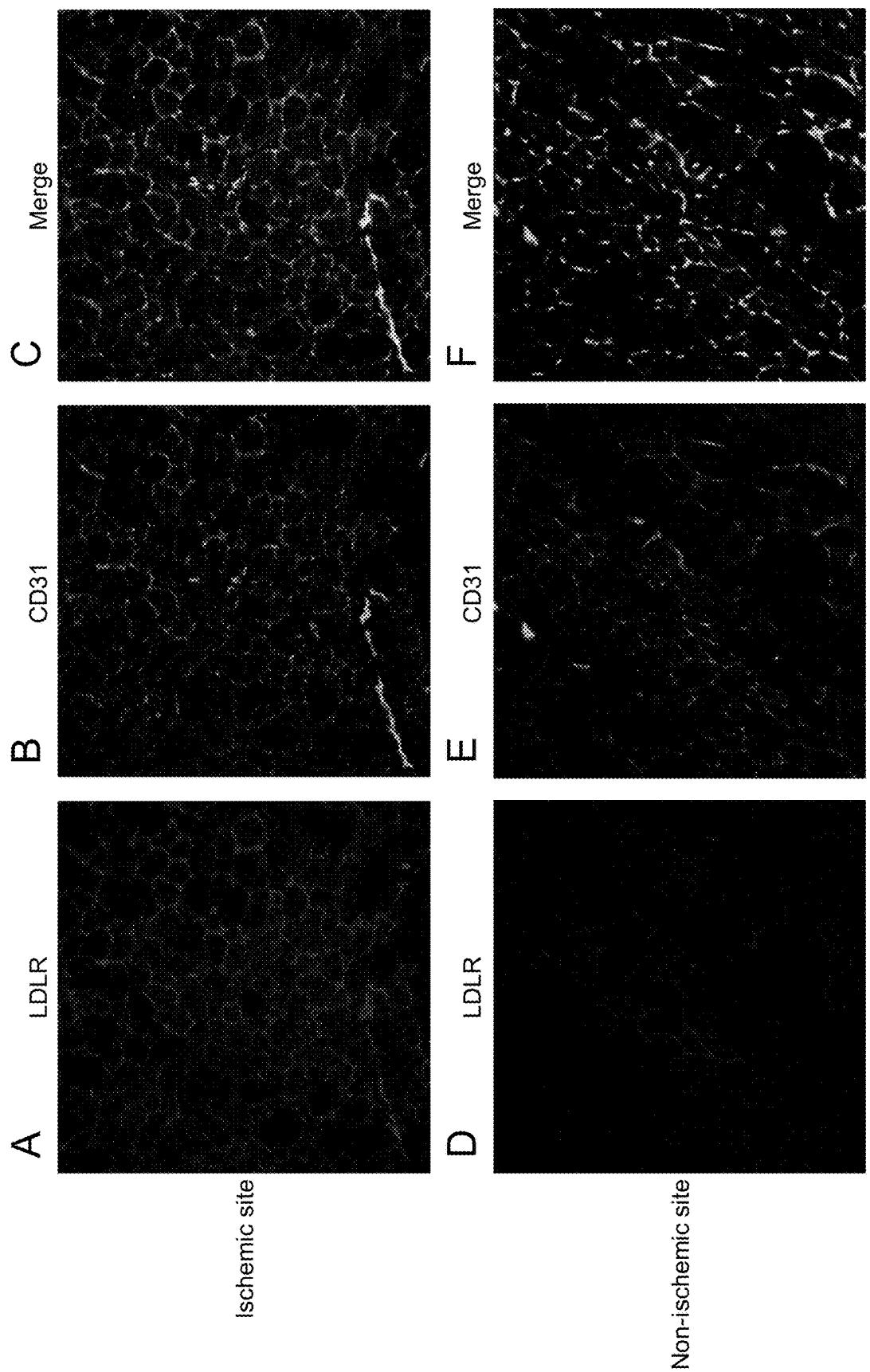
Figures 2, 34:
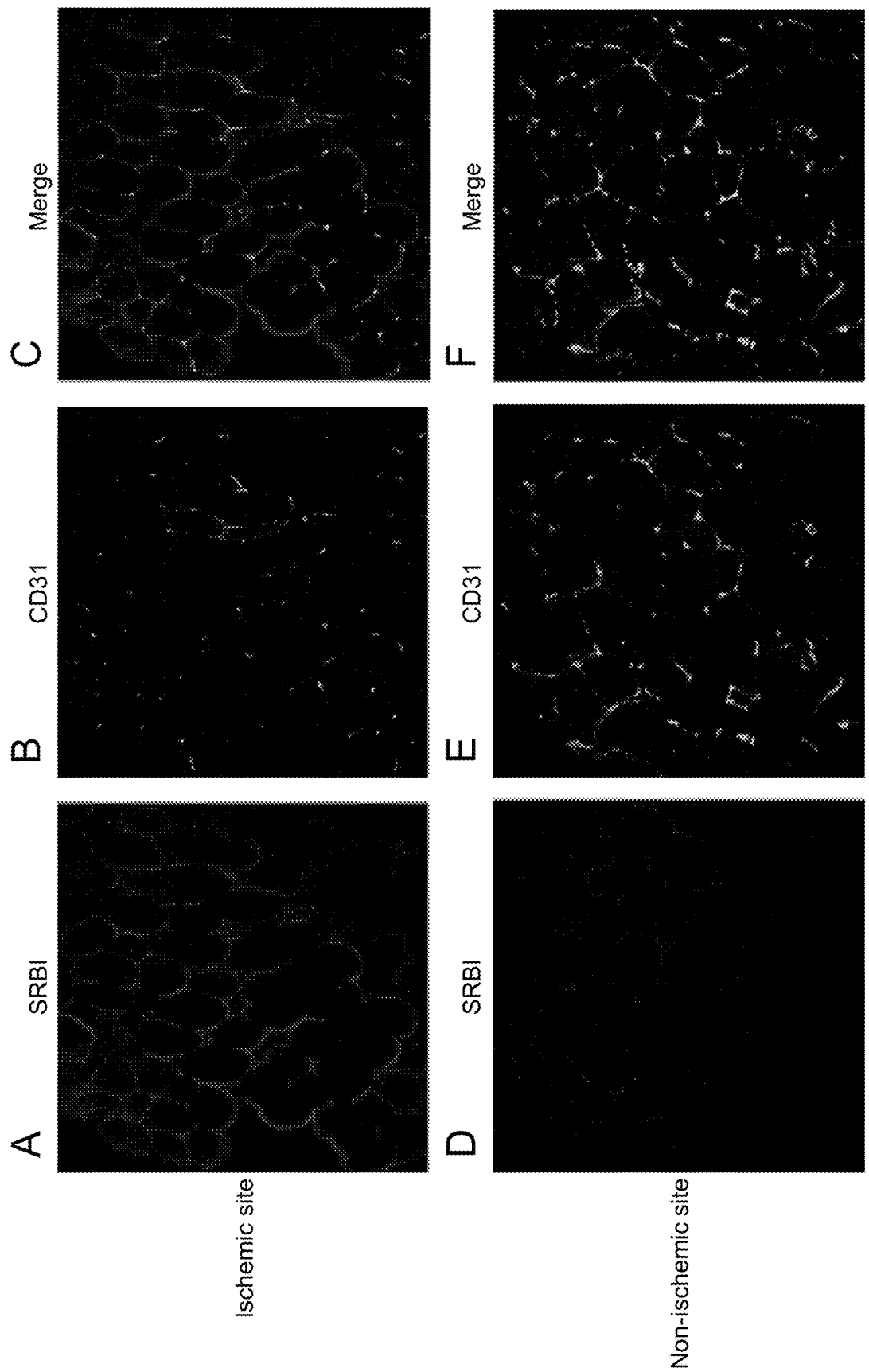

As shown in FIG. 34, the expression of LDLR and SRBI was increased in the ischemic site (A) compared with the normal site (B), particularly in CD31-positive vascular endothelial cells. This may be related to the increased efficiency of lipid-conjugated HDO delivery in an ischemic site.

All publications, patents and patent applications cited herein are incorporated herein by reference in their entirety.

The invention claimed is:

1. A method for modulating expression of a target transcriptional product in an ischemic site of a subject, comprising administering a composition to the subject, wherein the composition comprises a nucleic acid complex formed by annealing together a first nucleic acid strand comprising an antisense oligonucleotide region with respect to the target transcriptional product, and a lipid-conjugated second nucleic acid strand comprising a complementary region that is complementary to at least part of the first nucleic acid strand; and wherein the target transcriptional product is an mRNA or an mRNA precursor.

2. The method according to claim 1, wherein the first nucleic acid strand is from 9 to 50 bases in length.

3. The method according to claim 1, wherein said antisense oligonucleotide region in the first nucleic acid strand is from 9 to 20 bases in length.

4. The method-according to claim 1, wherein the second nucleic acid strand is from 9 to 50 bases in length.

5. The method according to claim 1, wherein said complementary region in the second nucleic acid strand is complementary to at least part of said antisense oligonucleotide region in the first nucleic acid strand.

6. The method according to claim 1, wherein the antisense oligonucleotide region is a gapmer type or mixmer type antisense oligonucleotide region.

7. The method according to claim 1, wherein the lipid is tocopherol or an analog thereof, or cholesterol or an analog thereof.

8. The method according to claim 7, wherein the lipid is cholesterol or an analog thereof.

9. The method according to claim 1, wherein the ischemic site is located in a brain, cardiac muscle, or lower limb skeletal muscle.

10. The method according to claim 1, wherein the administration is intravenous administration.

11. The method according to claim 1, wherein the modulation of expression of a target transcriptional product is reduction of the amount of the target transcriptional product.

12. The method according to claim 1, wherein the administration is an acute phase of ischemia.

13. The method according to claim 1 for treating an ischemic disease.

14. The method according to claim 13, wherein the ischemic disease is ischemic stroke, myocardial infarction, or arteriosclerosis obliterans.

15. The method according to claim 13, wherein the ischemic disease is a compressive ischemia, a traumatic ischemia or a thrombosis.

16. The method according to claim 13, wherein the ischemic disease is an acute ischemic disease selected from the group consisting of cerebral venous sinus thrombosis, cerebral vasoconstriction syndrome, cerebral vasculitis, cerebral hemorrhage, subarachnoid hemorrhage, moyamoya disease, cerebral arteriovenous fistula, cerebral arteriovenous malformation, cervical/cerebral artery dissection, head trauma, brain contusion, brain tumor, coagulation disorder, congenital connective tissue disease, pulmonary infarction, splenic infarction, radiation vasculopathy, age-related vasculopathy, and drug-induced vasculopathy.

17. The method according to claim 13, wherein the ischemic disease is a chronic ischemic disease selected from the group consisting of Fabry disease, cerebral amyloid angiopathy, traumatic disease, Buerger's disease, ischemic enteritis, diabetic peripheral neuropathy, and ischemic optic nerve disorder.

* * * * *